(12) United States Patent
Zion et al.

(10) Patent No.: US 8,940,690 B2
(45) Date of Patent: Jan. 27, 2015

(54) SYNTHETIC CONJUGATES AND USES THEREOF

(75) Inventors: Todd C. Zion, Marblehead, MA (US); Thomas M. Lancaster, Stoneham, MA (US)

(73) Assignees: National Institutes of Health (NIH), Bethesda, MD (US); The United States of America Dept. of Health and Human Services (DHHS), Washington, DC (US); The United States of America as represented by NIH Division of Extramural Inventions and Technology Resources (DEITR), Washington, DC (US)

( * ) Notice: Subject to any disclaimer, the term of this patent is extended or adjusted under 35 U.S.C. 154(b) by 701 days.

(21) Appl. No.: 13/145,534

(22) PCT Filed: Jan. 27, 2010

(86) PCT No.: PCT/US2010/022256
§ 371 (c)(1),
(2), (4) Date: Jul. 20, 2011

(87) PCT Pub. No.: WO2010/088286
PCT Pub. Date: Aug. 5, 2010

(65) Prior Publication Data
US 2011/0275560 A1  Nov. 10, 2011

Related U.S. Application Data

(60) Provisional application No. 61/147,878, filed on Jan. 28, 2009, provisional application No. 61/159,643, filed on Mar. 12, 2009, provisional application No. 61/162,053, filed on Mar. 20, 2009, provisional application No. 61/162,092, filed on Mar. 20, 2009, provisional application No. 61/162,058, filed on Mar. 20, 2009, provisional application No. 61/162,107, filed on Mar. 20, 2009, provisional application No. 61/163,084, filed on Mar. 25, 2009, provisional application No. 61/219,897, filed on Jun. 24, 2009, provisional application No. 61/223,572, filed on Jul. 7, 2009, provisional application No. 61/252,857, filed on Oct. 19, 2009.

(51) Int. Cl.
*A61K 38/28* (2006.01)
*C07K 14/62* (2006.01)

(52) U.S. Cl.
USPC .............................. 514/5.9; 530/345

(58) Field of Classification Search
USPC .............. 514/5.9; 530/396, 345; 424/488
IPC ............... A61K 47/36,38/1732, 38/28
See application file for complete search history.

(56) References Cited

U.S. PATENT DOCUMENTS

| | | | |
|---|---|---|---|
| 3,591,574 A | 7/1971 | Fenichel | |
| 3,684,791 A | 8/1972 | Geiger et al. | |
| 3,847,890 A | 11/1974 | Green et al. | |
| 4,348,387 A | 9/1982 | Brownlee et al. | |
| 4,372,948 A | 2/1983 | Yoshikumi et al. | |
| 4,377,567 A | 3/1983 | Geho | |
| 4,444,683 A | 4/1984 | Kim et al. | |
| 4,603,044 A | 7/1986 | Geho et al. | |
| 4,863,896 A | 9/1989 | Geho et al. | |
| 5,239,062 A | 8/1993 | Blattler et al. | |
| 5,395,924 A | 3/1995 | Blattler et al. | |
| 5,478,575 A | 12/1995 | Miyazaki et al. | |
| 5,527,524 A | 6/1996 | Tomalia et al. | |
| 5,563,056 A | 10/1996 | Swan et al. | |
| 5,723,589 A | 3/1998 | Miljkovic et al. | |
| 5,830,506 A | 11/1998 | Taylor | |
| 5,854,208 A | 12/1998 | Jones et al. | |
| 5,866,538 A | 2/1999 | Norup et al. | |
| 5,902,607 A | 5/1999 | Taylor | |
| 5,905,140 A | 5/1999 | Hansen | |
| 5,922,675 A | 7/1999 | Baker et al. | |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

Darbre, Current Topics in Medicinal Chemistry (UAE), 8(14), 1286-1293.*

(Continued)

*Primary Examiner* — David Lukton
(74) *Attorney, Agent, or Firm* — John David Reilly; Immac J. Thampoe

(57) ABSTRACT

The present disclosure provides a cross-linked material comprising conjugates which include two or more separate affinity ligands bound to a non-polymeric framework, wherein the molecular weight of the non-polymeric framework is less than 10,000 Da; and multivalent cross-linking agents that non-covalently bind the affinity ligands of the conjugates and thereby cross-link the conjugates to form a cross-linked material, wherein the non-covalent bonds between the multivalent cross-linking agents and the affinity ligands are competitively dissociated in the presence of excess amounts of a target molecule. The present disclosure also provides methods of making and methods of using these materials. In other aspects, the present disclosure provides exemplary conjugates including conjugates for use in glucose responsive cross-linked materials.

18 Claims, 30 Drawing Sheets

(56) References Cited

U.S. PATENT DOCUMENTS

| | | |
|---|---|---|
| 5,948,751 A | 9/1999 | Kimer et al. |
| 5,994,517 A | 11/1999 | Tso et al. |
| 6,034,054 A | 3/2000 | DeFelippis et al. |
| 6,180,757 B1 | 1/2001 | Bogsnes |
| 6,214,547 B1 | 4/2001 | Kjeldsen et al. |
| 6,323,311 B1 | 11/2001 | Liu et al. |
| 6,342,225 B1 | 1/2002 | Jones et al. |
| 6,410,053 B1 | 6/2002 | Taylor |
| 6,500,645 B1 | 12/2002 | Kjeldsen et al. |
| 6,521,738 B2 | 2/2003 | Kjeldsen et al. |
| 6,525,031 B2 | 2/2003 | Manoharan |
| 6,551,992 B1 | 4/2003 | DeFelippis et al. |
| 6,777,207 B2 | 8/2004 | Kjeldsen et al. |
| 6,844,166 B1 | 1/2005 | Wolf |
| 6,869,930 B1 | 3/2005 | Havelund et al. |
| RE39,055 E | 4/2006 | Jones et al. |
| 7,063,863 B2 | 6/2006 | Taylor |
| 7,087,408 B2 | 8/2006 | Kjeldsen et al. |
| 7,105,314 B2 | 9/2006 | Kjeldsen |
| 7,316,999 B2 | 1/2008 | Hoeg-Jensen et al. |
| 7,317,000 B2 | 1/2008 | Hoeg-Jensen et al. |
| 7,423,014 B2 | 9/2008 | Ekwuribe et al. |
| 7,531,191 B2 | 5/2009 | Zion et al. |
| 7,687,608 B2 | 3/2010 | Lancaster et al. |
| 8,062,668 B2 | 11/2011 | Ying et al. |
| 2002/0068295 A1 | 6/2002 | Madou et al. |
| 2006/0019874 A1 | 1/2006 | Radhakrishnan et al. |
| 2006/0216265 A1 | 9/2006 | Goodman et al. |
| 2006/0247154 A1 | 11/2006 | Palmieri et al. |
| 2007/0099820 A1 | 5/2007 | Lancaster et al. |
| 2007/0207498 A1 | 9/2007 | Palmieri et al. |
| 2009/0053167 A1 | 2/2009 | DeFrees |
| 2009/0137454 A1 | 5/2009 | Fynbo et al. |
| 2010/0130726 A1 | 5/2010 | Lancaster et al. |
| 2011/0275560 A1 | 11/2011 | Zion et al. |
| 2011/0281791 A1 | 11/2011 | Zion et al. |
| 2011/0281792 A1 | 11/2011 | Zion et al. |
| 2011/0281939 A1 | 11/2011 | Zion et al. |
| 2011/0301083 A1 | 12/2011 | Zion et al. |
| 2012/0046223 A1 | 2/2012 | Zion et al. |

FOREIGN PATENT DOCUMENTS

| | | |
|---|---|---|
| EP | 0119650 | 9/1984 |
| EP | 0725648 | 8/1996 |
| WO | WO81/00354 | 2/1981 |
| WO | WO84/01896 | 5/1984 |
| WO | WO99/10645 | 9/1990 |
| WO | WO99/52934 | 10/1999 |
| WO | WO01/92334 | 12/2001 |
| WO | WO03/035011 | 5/2003 |
| WO | WO03/047462 | 6/2003 |
| WO | WO03/048915 | 6/2003 |
| WO | WO03/074087 | 9/2003 |
| WO | WO2004/057002 | 7/2004 |
| WO | WO2006/008238 | 1/2006 |
| WO | 2006/062685 | 6/2006 |
| WO | WO2006/082184 | 8/2006 |
| WO | WO2006/088473 | 8/2006 |
| WO | WO2006/102762 | 10/2006 |
| WO | WO2007/042470 | 4/2007 |
| WO | WO2007/043050 | 4/2007 |
| WO | WO2008/012440 | 1/2008 |
| WO | WO2008/012528 | 1/2008 |
| WO | WO2008/036147 | 3/2008 |
| WO | WO2009/033588 | 3/2009 |
| WO | WO2009/059450 | 5/2009 |
| WO | WO2009/089396 | 7/2009 |
| WO | WO2009/104199 | 8/2009 |
| WO | WO2011/000823 | 1/2011 |

OTHER PUBLICATIONS

Hamelryck, Journal of Molecular Biology 299(4), 875-883, 2000.*

International Search Report and Written Opinion for PCT/US10/22225, mailed on Mar. 9, 2010.

Lindhorst et al. Trivalent alpha-D-mannoside clusters as inhibitors of type-1 fimbriae-mediated adhesion of *Escherichia coli*: structural variation and biotinylation. J. Chem. Soc. Perkin Trans 1:823-831 (2001).

Baudys, et al., "Physical Stabilization of Insulin by Glycosylation" *J Pharma Sci* (1995) 64: 28-33.

Brownlee & Cerami, "A Glucose-Controlled-Insulin-Delivery-System: Semisynthetic Insulin Bound to Lectin" *Diabetes* (1983) 32: 499-504.

Brownlee & Cerami, "Glycosylated Insulin Complexed to Concanavalin A" *Science* (1979) 206: 1190-1191.

Dea, et al., "Albumin Binding of Acylated Insulin (NN304) Does Not Deter Action to Stimulate Glucose Uptake" *Diabetes* (2002) 51: 762-769.

Eggert, et al., "A New Glucose Selective Fluorescent Bisboronic Acid" *J Org Chem* (1999) 64: 3846-3852.

Heinnemann, et al., "Time-action profile of the soluble, fatty acid acylated, long acting insulin analogue NN304" *Diabetic Med* (1999) 16: 332-338.

Jeong, et al., "Self Regulating Insulin Delivery Systems I. Synthesis and Characterization of Glycosylated Insulin" *J of Controlled Release* (1984) 1: 57-66.

Lee et al., "Biochemistry of crbohydrate-protein interaction" *FASEB J* (1992) 3193-3200.

Monsigny, et al., "Endogenous Lectins and Drug Targeting" *Annals NY Acad Sci* (1988) 551: 399-414.

Ruziak, et al., "Basal activity profiles of NPH and [Ne-palmitoyl Lys (B29) human insulins in subjects with IDDM" *Diabetologia* (1998) 41: 116-120.

Shojaee-Moradie, "Novel Hepatoselective Insulin Analog" *Diabetes Care* (2000) 23: 1124-1129.

Yamazaki, et al., "Endogenous lectins as targets for drug delivery" *Adv Drug Delivery Rev* (2000) 43: 225-244.

* cited by examiner (a) IPC Peak Retention Times, %Free Insulin, and %Desamido Insulin

| Sample | Peak 1 RT[1] (min) | Peak 2 RT (min) | Peak 3 RT (min) | % Purity IPC | % Free Insulin | % Desamido Insulin |
|---|---|---|---|---|---|---|
| HS-1-60-1 (fresh) | 20.62 | - | - | >99 | <0.1 | <0.1 |
| HS-1-60-1 (AST, PBS) | 20.61 | 19.19 | - | 85 | <0.1 | <0.1 |
| HS-1-60-1 (AST, HEPES) | 20.65 | - | - | >99 | <0.1 | <0.1 |
| TL-13-85 (fresh) | 20.46 | - | - | >99 | <0.1 | <0.1 |
| TL-13-85 (AST, PBS) | 20.40 | 19.84 | 18.91 | 30 | <0.1 | <0.1 |
| TL-13-85 (AST, HEPES) | 20.46 | - | - | >99 | <0.1 | <0.1 |

[1] C8 reverse phase column, water:acetonitrile (0.1% TFA) elution gradient, RT = Retention Time

Figure 3(a)

(b) Mass Spectroscopy Data on IPC's and IPC Breakdown Products

| Sample | Peak 1 MW (Da) | Peak 2 MW (Da) | Peak 3 MW (Da) |
|---|---|---|---|
| HS-1-60-1 (fresh) | 6730 [2] | - | - |
| HS-1-60-1 (AST, PBS) | 6730 | 5947 | - |
| HS-1-60-1 (AST, HEPES) | 6730 | - | - |
| TL-13-85 (fresh) | 6829 [2] | - | - |
| TL-13-85 (AST, PBS) | 6829 | 5944 | 7928 |
| TL-13-85 (AST, HEPES) | 6829 | - | - |

[2] The two IPC's shown here have different structures and, therefore, different MW's

SYNTHETIC CONJUGATES AND USES THEREOF

RELATED APPLICATIONS

This application is a national phase application of International Application No. PCT/US2010/22256, filed Jan. 27, 2010, which claims priority to U.S. Provisional Application No. 61/147,878 filed Jan. 28, 2009, U.S. Provisional Application No. 61/159,643 filed Mar. 12, 2009, U.S. Provisional Application No. 61/162,107 filed Mar. 20, 2009, U.S. Provisional Application No. 61/162,053 filed Mar. 20, 2009, U.S. Provisional Application No. 61/162,058 filed Mar. 20, 2009, U.S. Provisional Application No. 61/162,092 filed Mar. 20, 2009, U.S. Provisional Application No. 61/163,084 filed Mar. 25, 2009, U.S. Provisional Application No. 61/219,897 filed Jun. 24, 2009, U.S. Provisional Application No. 61/223,572 filed Jul. 7, 2009, and U.S. Provisional Application No. 61/252,857 filed Oct. 19, 2009, the content of each of which is hereby incorporated by reference in its entirety.

In accordance with 37 CFR 1.52(e)(5), a Sequence Listing in the form of a text file (entitled "Sequence listing_0042.txt," created on Jan. 25, 2010, and 1 kilobyte) is incorporated herein by reference in its entirety.

STATEMENT REGARDING FEDERALLY SPONSORED RESEARCH OR DEVELOPMENT

This invention was made with government support under Grant Numbers DK079482 and DK080565, awarded by the National Institutes of Health ("NIH"). The U.S. government has certain rights in the invention.

BACKGROUND

The majority of "controlled-release" drug delivery systems known in the prior art (e.g., U.S. Pat. No. 4,145,410 to Sears which describes drug release from capsules which are enzymatically labile) are incapable of releasing drugs at intervals and concentrations which are in direct proportion to the amount of a molecular indicator (e.g., a metabolite) present in the human body. The delivery or release of drug in these prior art systems is thus not literally "controlled," but simply a slow release which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

In certain embodiments of the Zion system, multivalent glucose-binding molecules (e.g., lectins) are combined with a glycosylated polymer-insulin conjugate. The glycosylated polymer contains multiple saccharide binding groups and forms insoluble hydrogels or particles in the presence of the glucose-binding molecule. The gel releases the glycosylated polymer-insulin conjugate in response to increases in glucose concentration. As discussed below, the glycosylated polymer-insulin conjugates that are used in existing conjugates present certain difficulties. There is therefore a need in the art for conjugates that can overcome these difficulties and yet function within a Zion system that responds to useful concentrations of glucose (or other triggering target molecule).

SUMMARY

In one aspect, the present disclosure provides a cross-linked material comprising conjugates which include two or more separate affinity ligands bound to a non-polymeric framework, wherein the molecular weight of the non-polymeric framework is less than 10,000 Da; and multivalent cross-linking agents that non-covalently bind the affinity ligands of the conjugates and thereby cross-link the conjugates to form a cross-linked material, wherein the non-covalent bonds between the multivalent cross-linking agents and the affinity ligands are competitively dissociated in the presence of excess amounts of a target molecule. The present disclosure also provides methods of making and methods of using these materials. In other aspects, the present disclosure provides exemplary conjugates including conjugates for use in glucose responsive cross-linked materials.

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987.

Acyl—As used herein, the term "acyl," refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=NR$^{X1}$)$R^{X1}$, C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, isobutyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., $-(CH_2)_z-$, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—N$(R^\circ)_2$; or —$(C_{1-4}$ straight or branched)alkylene)C(O)O—N$(R^\circ)_2$, wherein each $R^\circ$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, —(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —SSR$^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^•$, —(halo$R^•$), —OH, —$OR^•$, —O(halo$R^•$), —CN, —C(O)OH, —C(O)$OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, —(halo$R^•$), —OH, —$OR^•$, —O(halo$R^•$), —CN, —C(O)OH, —C(O)$OR^•$, —$NH_2$, —$NHR^•$, —$NR^•_2$, or —$NO_2$, wherein each $R^•$ is unsubstituted or where preceded by "halo" is substituted only with one or more halogens, and is independently $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3- diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4''-tris(4,5-dichlorophthalimidophenyl) methyl, 4,4',4''-tris(levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benziisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Agglutinated—When two or more cells are "agglutinated" by a cross-linking agent as described herein, they are each physically associated with the cross-linking agent in a cell-agent-cell complex. Typically, agglutination only occurs once the cross-linking agent concentration reaches a threshold concentration. This concentration is referred to as the minimum agglutination concentration (MAC). The MAC for a given cross-linking agent is commonly measured using a spectrophotometric plate reader that can quantify changes in solution absorbance.

Aptamer—As used herein, the term "aptamer" refers to a polynucleotide or polypeptide that binds specifically to a target molecule. In general, an aptamer is said to "bind specifically" to its target molecule if it associates at a detectable level with the target molecule and does not associate detectably with unrelated molecular entities (e.g., molecules which share no common structural features with the target molecule) under similar conditions. Specific association between a target molecule and an aptamer will typically be dependent upon the presence of a particular structural feature of the target molecule such as an epitope recognized by the aptamer. Generally, if an aptamer is specific for epitope A, the presence of a molecule containing epitope A or the presence of free unlabeled epitope A in a reaction containing both free labeled epitope A and the aptamer thereto, will reduce the amount of labeled epitope A that binds to the aptamer. In general, it is to be understood that specificity need not be absolute. Indeed, it is well known in the art that aptamers may cross-react with other epitopes in addition to the target epitope. Such cross-reactivity may be acceptable depending upon the application for which the aptamer is to be used. Thus the degree of specificity of an aptamer will depend on the context in which it is being used. It is also to be understood that specificity may be evaluated in the context of additional factors such as the affinity of the aptamer for the target molecule versus the affinity of the aptamer for non-target molecules.

Associated—As used herein, two entities are physically "associated" with one another when they are bound by direct non-covalent interactions. Desirable non-covalent interactions include those of the type which occur between an immunoglobulin molecule and an antigen for which the immunoglobulin is specific, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. For example, the association properties of a selected cross-linking agent and target molecule can be quantified using methods well known in the art.

Biodegradable—As used herein, the term "biodegradable" refers to molecules that degrade (i.e., lose at least some of their covalent structure) under physiological or endosomal conditions. Biodegradable molecules are not necessarily hydrolytically degradable and may require enzymatic action to degrade.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Exogenous—As used herein, an "exogenous" molecule is one which is not present at significant levels in a patient unless administered to the patient. In certain embodiments the patient is a mammal, e.g., a human, a dog, a cat, a rat, etc. As used herein, a molecule is not present at significant levels in a patient if normal serum for that type of patient includes less than 0.1 mM of the molecule. In certain embodiments normal serum for the patient may include less than 0.08 mM, less than 0.06 mM, or less than 0.04 mM of the molecule.

Hyperbranched—As used herein, a "hyperbranched" structure is a covalent structure that includes at least one branched branch (e.g., a dendrimeric structure). A hyperbranched structure may include polymeric and/or non-polymeric substructures.

Normal serum—As used herein, "normal serum" is serum obtained by pooling approximately equal amounts of the liquid portion of coagulated whole blood from five or more non-diabetic patients. A non-diabetic human patient is a randomly selected 18-30 year old who presents with no diabetic symptoms at the time blood is drawn.

Lectin—As used herein, a "lectin" is a protein that binds with specificity to saccharides and polysaccharides. A lectin can be of any origin (e.g., plant, animal or other). In certain embodiments a lectin can be isolated from a natural source. In other embodiments a lectin can be produced synthetically or recombinantly. A lectin can be composed of one or more subunits under physiological conditions. In preferred embodiments a lectin is composed of two or more subunits under physiological conditions (e.g., four subunits). The subunits may be the same or different.

Mitogenic lectin—A "mitogenic lectin" is a lectin that stimulates the proliferation of T-cells as measured by a thymidine uptake assay using peripheral blood mononuclear cells (PBMC) from one or more healthy patients. Generally a mitogenic lectin will produce a detectable level of thymidine uptake at concentrations of 1 ug/ml. Exemplary mitogenic lectins include, but are not limited to, artocarpus integrifolia agglutinin (Jacalin), bauhinia purpurea agglutinin (BPA), concanavalin A (Con A), succinyl-concanavalin A (s-Con A), erythrina corallodendron agglutinin (ECorA), euonymus europaeus agglutinin (EEA), glycine max agglutinin (SBA), Lens culinaris agglutinin (LcH), maackia amurensis agglutinin (MAA), phaseolus vulgaris agglutinin (PHA), pokeweed mitogen (PWM), wheat germ agglutinin (WGA), and vicia faba agglutinin (VFA) all of which are available from Sigma-Aldrich of St. Louis, Mo. It is to be understood that the terms "mitogenic lectin" include derivatives of native lectins that retain the ability to stimulate the proliferation of T-cells (e.g., derivatives that include amino acid substitutions, deletions or additions). Exemplary derivatives are those into which amino acid residues have been introduced by site-directed mutagenesis (e.g., in order to provide additional reactive groups for chemical modification). Generally, suitable derivatives will have at least 90% sequence homology with a native lectin as determined using standard methods known in the art (e.g., using Blast with default settings). Preferably the derivatives will have at least 95% sequence homology, more preferably 99% sequence homology with a native lectin. Without limitation, exemplary derivatives may induce a level of T-cell proliferation that is at least 90% that of their native counterparts. More preferably, the level is at least 95%, even more preferably at least 99%.

Native lectin—As used herein, a "native lectin" is a protein with the chemical composition of a lectin that is found in nature.

Percentage homology—As used herein, the terms "percentage homology" refer to the percentage of sequence identity between two sequences after optimal alignment as defined in the present disclosure. For example, two nucleotide sequences are said to be "identical" if the sequence of nucleotides in the two sequences is the same when aligned for maximum correspondence as described below. Sequence comparisons between two nucleotide sequences are typically performed by comparing sequences of two optimally aligned sequences over a region or "comparison window" to identify and compare regions of sequence similarity. Optimal alignment of sequences for comparison may be conducted by the local homology algorithm of Smith and Waterman, Ad. App. Math. 2:482 (1981), by the homology alignment algorithm of Neddleman and Wunsch, J. Mol. Biol. 48:443 (1970), by the search for similarity method of Pearson and Lipman, Proc. Natl. Acad. Sci. USA 85:2444 (1988), by computerized implementation of these algorithms, or by visual inspection.

Percentage of sequence identity—"Percentage of sequence identity" is determined by comparing two optimally aligned sequences over a comparison window, where the portion of the nucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide residue occurs in both sequences to yield the number of matched positions, dividing the number of matched positions by the total number of positions in the window of comparison and multiplying the result by 100 to yield the percentage of sequence identity. This definition of sequence identity given above is the definition that would be used by one of ordinary skill in the art. The definition by itself does not need the help of any algorithm. The algorithms are only helpful to facilitate the optimal alignments of sequences, rather than calculate sequence identity. From this definition, it follows that there is a well defined and only one value for the sequence identity between two compared sequences which value corresponds to the value obtained for the optimal alignment.

Physiological conditions—As used herein, "physiological conditions" are those conditions that are found in the arterial blood of a typical patient. Generally, the patient is a mammal, e.g., a human, dog, cat, mouse, etc. In human patients, the pH under physiological conditions is typically between about 7.35 and about 7.45 (preferably about 7.40). Human physiological temperatures range from about 36.4 to about 37.4 C (preferably about 36.9 C).

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Treat—As used herein, the term "treat" (or "treating", "treated", "treatment", etc.) refers to the administration of a material of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

BRIEF DESCRIPTION OF THE DRAWINGS

FIG. 3(a): Accelerated stability testing (AST) chemical stability results (a) RP-HPLC AST conjugate stability.

FIG. 3(b): Accelerated stability testing (AST) chemical stability results (b) LC/MS data on AST conjugates.

Figure 22:
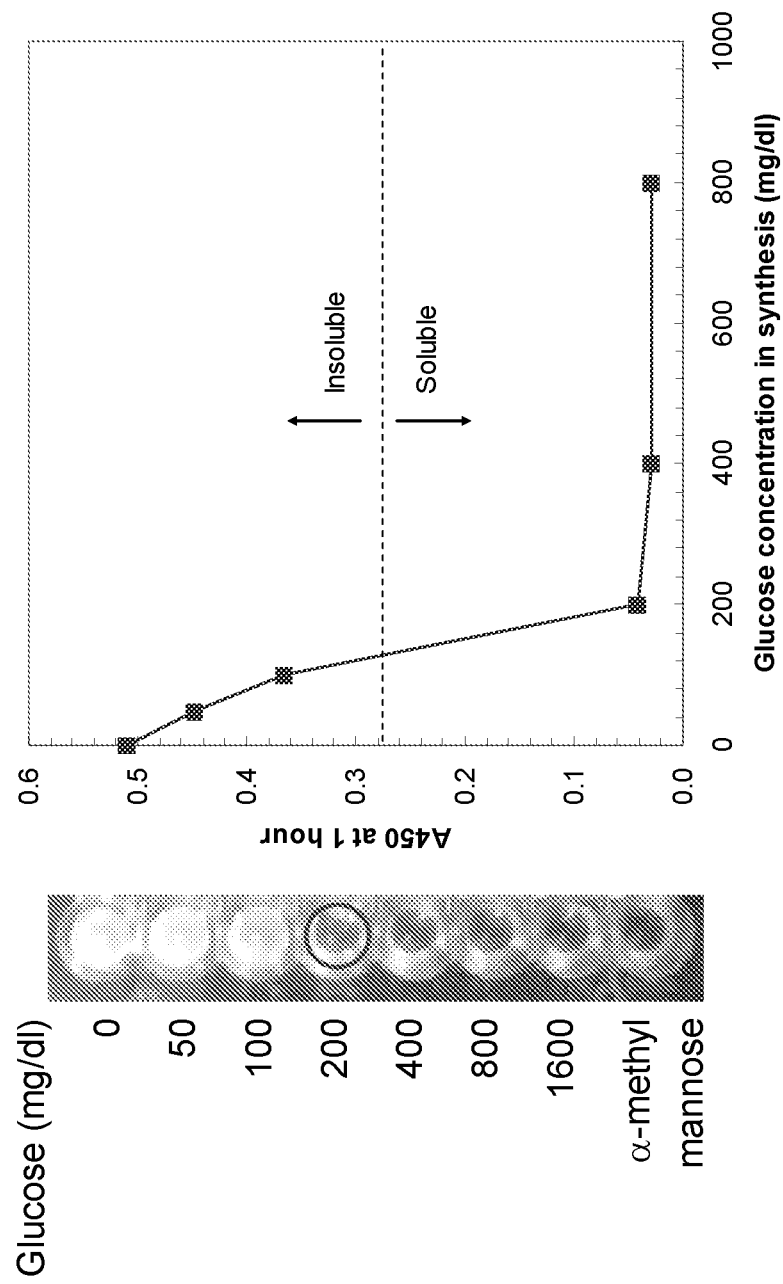

FIG. 22: Left: image taken after one hour of precipitation as a function of glucose concentration. Right: Plot of the amount of light blocked by each of the wells as measured by the absorbance at 450 nm (A450) as a function of glucose concentration after one hour of mixing the conjugate and modified lectin.

Figure 23:
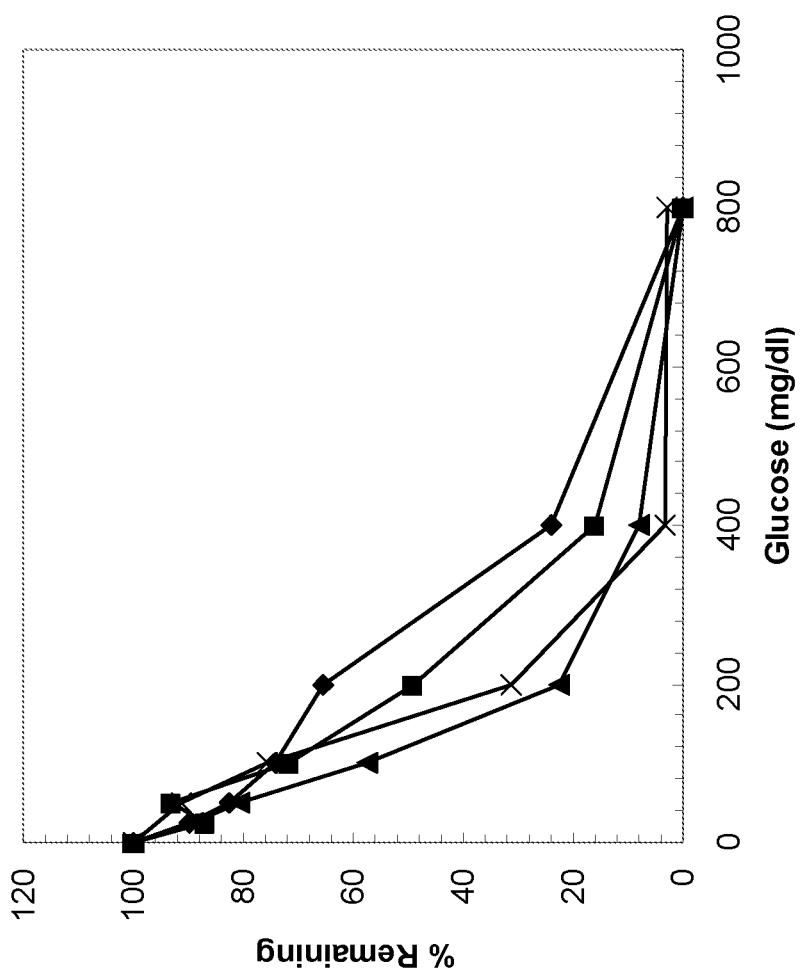

FIG. 23: Amount of glucose-responsive material constructed (using an exemplary insulin conjugate) remaining insoluble as a remaining insoluble as a function of glucose concentration after six hours of incubation at 37° C. in the presence of (♦) porcine serum, (■) human serum, (▲) rat serum, and (x) 1×PBS buffer.

Figure 24:
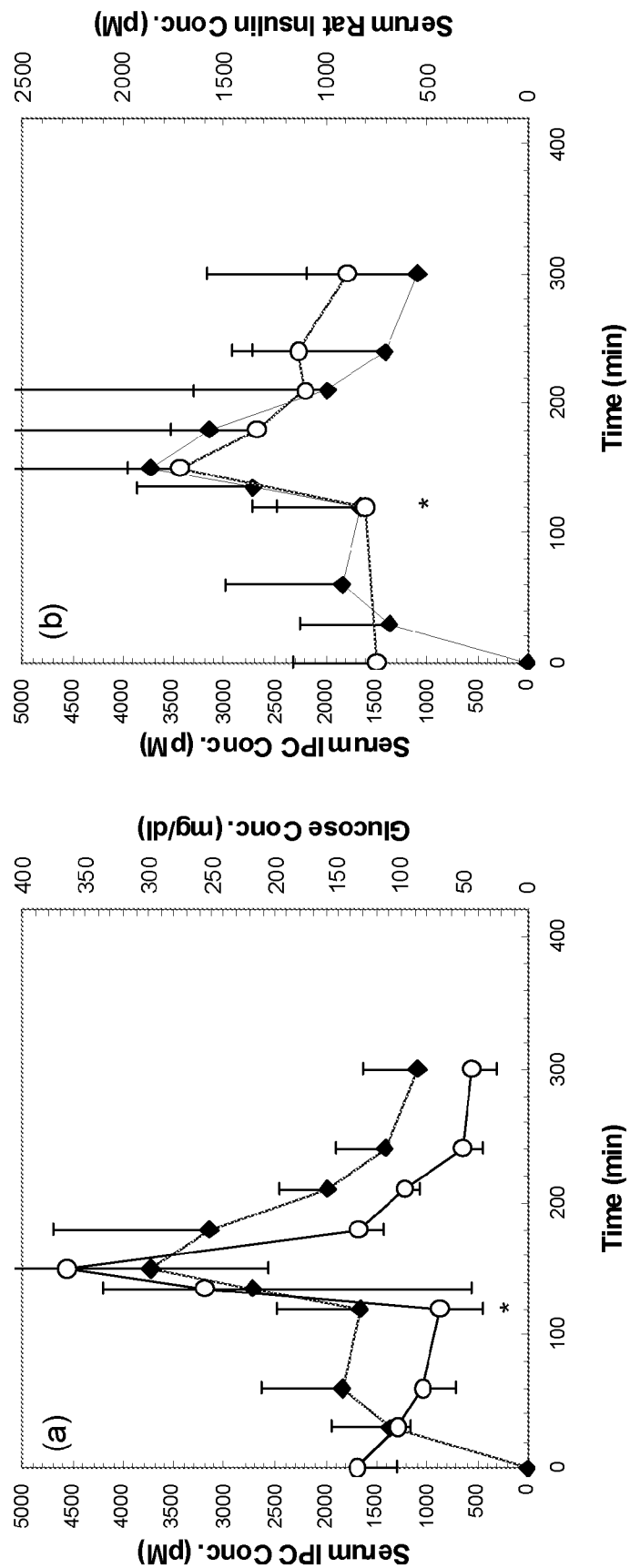

FIG. 24: (a) Plot of (♦) serum insulin and (○) blood glucose levels following subcutaneous injection in non-diabetic SD rats at time 0 with glucose-responsive materials constructed from exemplary conjugate X and ACA. An i.p. injection of glucose was administered at 120 min as indicated by the *. (b) Serum insulin plots of (♦) glucose-responsive materials constructed from exemplary conjugate X and ACA and (○) endogenous rat pancreatic insulin as a function of time in response to an i.p. injection of glucose administered at 120 min as indicated by the *. Each set of data represents the average and standard deviation for n=3 rats.

Figure 25:
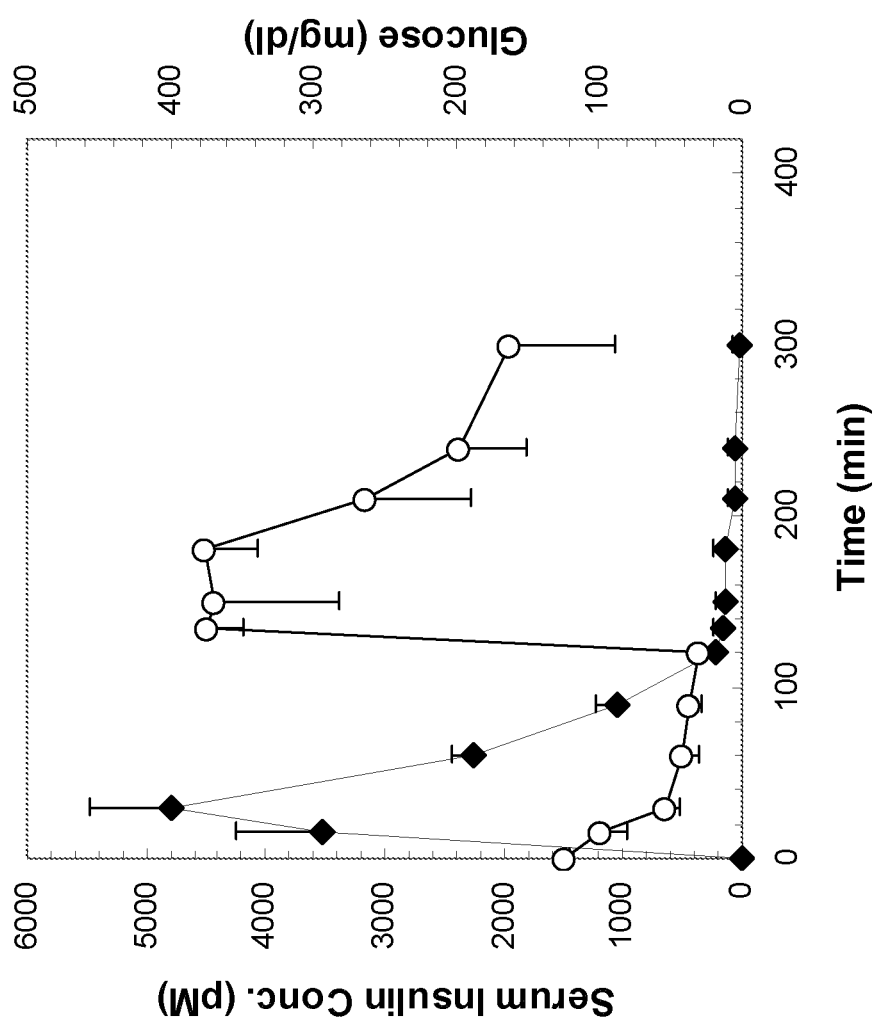

FIG. 25: Plot of (♦) serum insulin and (○) blood glucose levels following subcutaneous injection in non-diabetic SD rats at time 0 with recombinant human insulin (RHI). An i.p. injection of glucose was administered at 120 min as indicated by the *.

Figure 26:
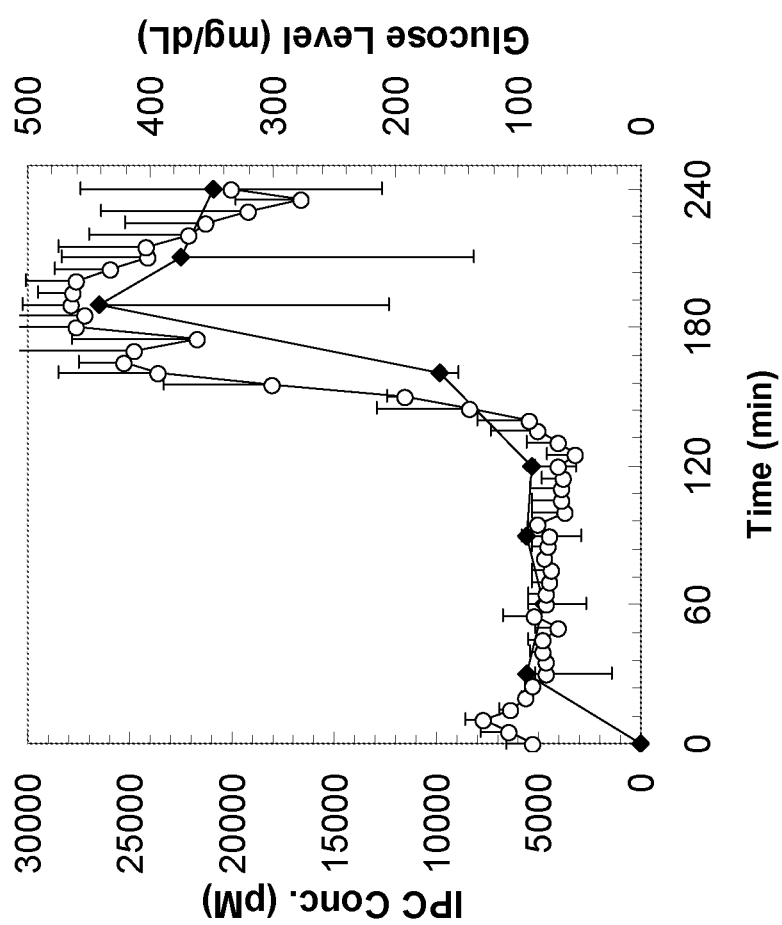

FIG. 26: Plot of (υ) serum insulin and (□) blood glucose concentration from glucose clamp studies following the subcutaneous injection of an exemplary glucose-responsive material (TSAT-C6-AEM-2-insulin/ACA) in n=4 non-diabetic rats. Following injection, the glucose levels were maintained at 100 mg/dl for 120 min using an i.v. glucose infusion after which the glucose levels were ramped up to and maintained at 400 mg/dl for the last 120 min. The data represent the average and standard deviation for n=4 rats.

Figure 27:
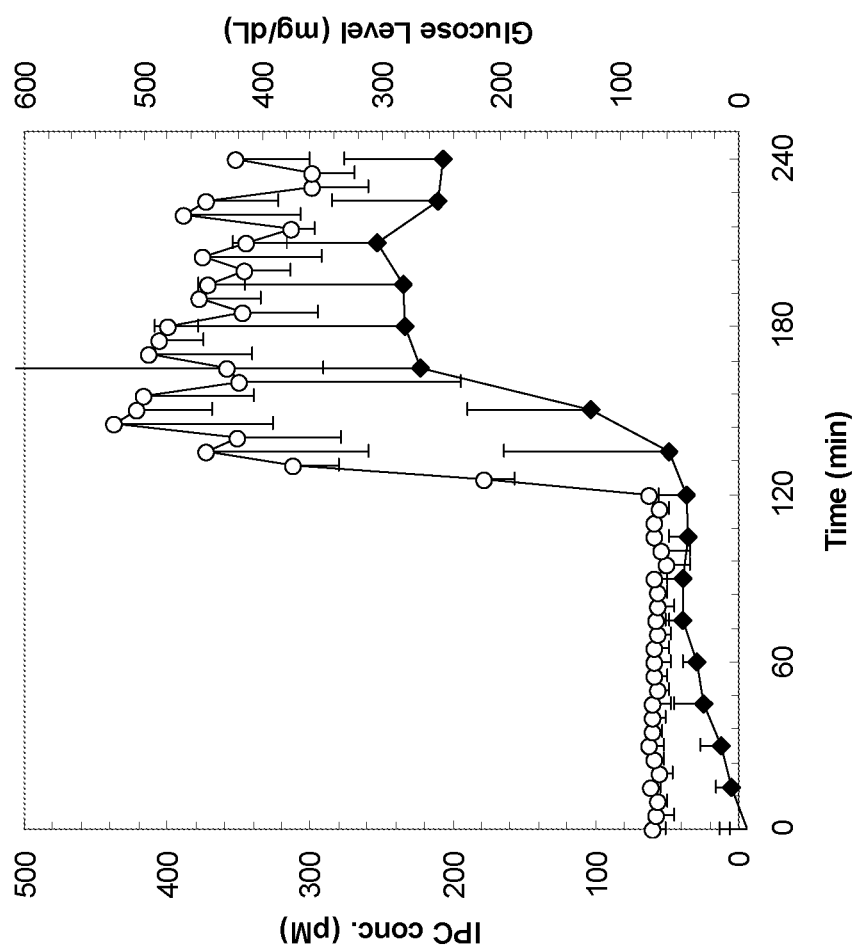

FIG. 27: Plot of (♦) serum insulin and (○) blood glucose concentration from glucose clamp studies following the subcutaneous injection of an exemplary glucose-responsive material (TSAT-C6-AEM-2-insulin/ACA) in n=4 non-diabetic pigs. Following injection, the glucose levels were maintained at 65 mg/dl for 120 min using an i.v. glucose infusion after which the glucose levels were ramped up to and maintained at 400 mg/dl for the last 120 min. The data represent the average and standard deviation for n=4 pigs.

Figure 28:
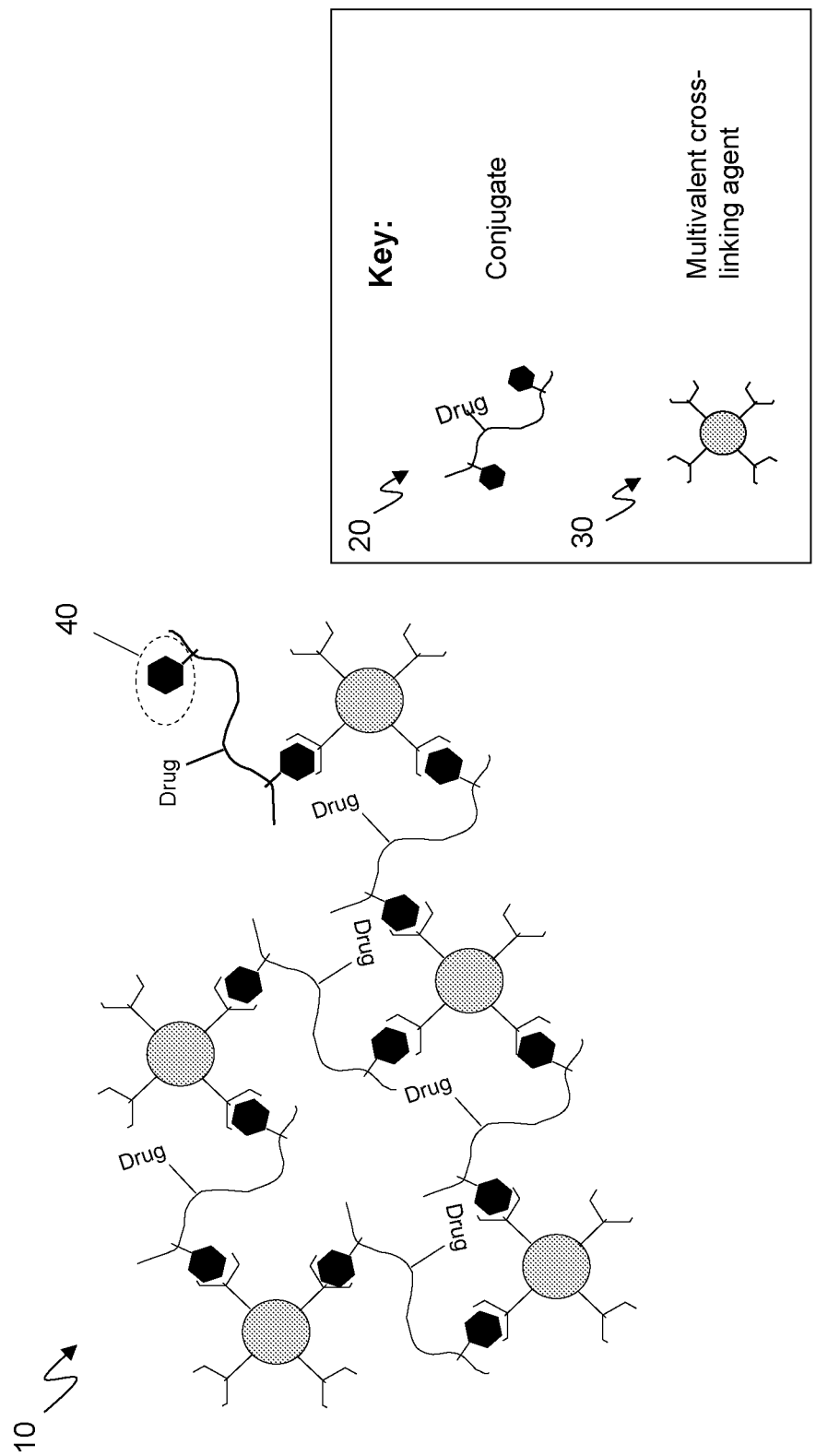

FIG. 28: Schematic of a cross-linked material 10 which is capable of controllably releasing conjugates 20 in response to a target molecule (e.g., glucose). The materials are prepared by combining the conjugates 20 with multivalent cross-linking agents 30 that non-covalently bind the affinity ligands 40 of the conjugates 20 and thereby cross-link the conjugates 20 to form the cross-linked material 10. The non-covalent bonds between the multivalent cross-linking agents 30 and the affinity ligands 40 are competitively dissociated in the presence of excess amounts of the target molecule (e.g., glucose).

Figure 29:
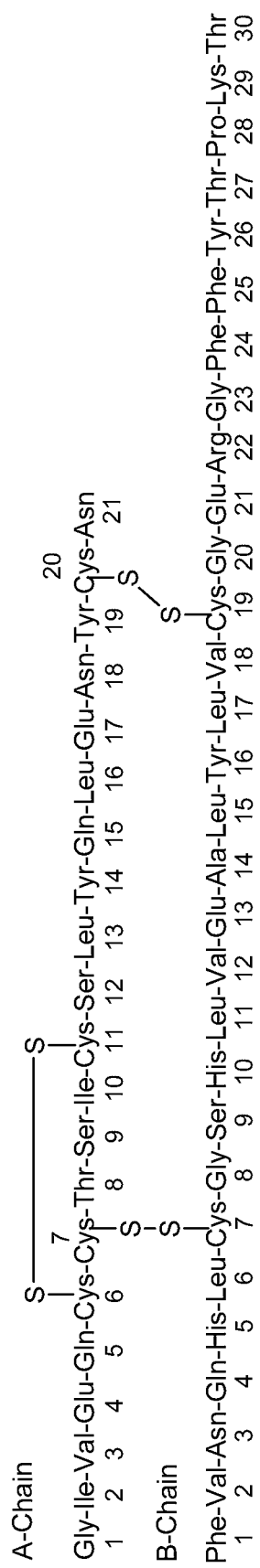

FIG. 29: Structure of wild-type human insulin.

DETAILED DESCRIPTION OF VARIOUS EMBODIMENTS

This application refers to a number of documents including patent and non-patent documents. The entirety of each of these documents is incorporated herein by reference.

Whether used to deliver insulin or other drugs, the glycosylated polymer conjugates used in existing Zion conjugates present certain difficulties. Indeed, as a result of the high molecular weight (MW) of the glycosylated polymers, the conjugates have a much higher MW than the native drug. The conjugate is therefore absorbed into the systemic circulation more slowly. In addition, once in the circulation, the intrinsic bioactivity of the conjugate may be reduced and the rate of elimination may be slower. In US 2007-0099820 to Lancaster et al. we described one solution to this problem which involved attaching the drug to a polymer which is enzymatically degraded at the site of administration. While these enzymatically degradable conjugates behaved more like unconjugated insulin once released from the Zion system, they suffered from two main disadvantages, namely: an inherent difficulty in manufacturing large quantities of pharmaceutical grade material and unwanted degradation due to enzyme activity even in the absence of target molecule.

For example, the exemplary glycogen-based conjugates of Lancaster were derived from animal and plant sources with broad and variable MW distributions and residual foreign protein content that required removal prior to insulin conjugation. Each separate lot and type of glycogen had to be subjected to MW fractionation to center and reduce the polydispersity of the distribution leading to substantially increased production costs and corresponding yield losses. Furthermore, each glycogen chain was modified with a variable number of sugar affinity ligands leading to not only a distribution of chain lengths but also a distribution of affinity ligands across those different chain lengths.

As described in the Examples, we also discovered rather unexpectedly that different animal species can possess unique levels of conjugate-degrading enzyme activity. In the case of rats, for example, the amylase activity was enough to render free glycogen conjugates bioactive but low enough to cause only marginal degradation of cross-linked conjugate. In pigs, however, the activity was high enough to cause rapid degradation of cross-linked conjugates thereby leading to large amounts of insulin release even in the absence of glucose. These results meant that the degradability of conjugates would likely need to be designed specifically for each animal species in order to balance conjugate bioactivity with unwanted degradation of cross-linked conjugates. From a pharmaceutical development perspective, regulatory agencies usually require safety data on the same formulation in two animal species prior to initiating human clinical trials. However, due to species differences in enzyme degradability the pharmacokinetics would likely differ in each of the two species.

There is therefore a need in the art for conjugates which can function within a Zion system without being susceptible to enzymatic degradation. Ideally such conjugates would also be single, synthetic, well-characterized molecular entities that do not suffer from the production challenges encountered with polymeric natural products. We hypothesized that suitable non-biodegradable conjugates would need to be of low molecular weight in order to exhibit similar pharmacokinetic (PK) and pharmacodynamic (PD) properties to the unconjugated drug. However, we were also aware that previous studies with the Zion system (U.S. Patent Application Publication No. 2004-0202719 and "Glucose-responsive materials for self-regulated insulin delivery", Thesis, Massachusetts Institute of Technology, Dept. of Chemical Engineering, 2004) had shown that the ability of conjugates to self-assemble into insoluble cross-linked materials is eliminated as the molecular weight of conjugates is decreased. In order to overcome this problem we therefore had to develop new families of higher affinity ligands than previously used for these types of applications. In parallel, we developed low molecular weight frameworks to which we chemically attached these ligands in a multivalent fashion with a range of linker arm lengths and chemistries. Unexpectedly, we have found that certain high affinity ligands when conjugated to appropriate frameworks that are low enough in molecular weight to preserve conjugate bioactivity are also capable of forming insoluble cross-linked materials when combined with suitable multivalent cross-linking agents. As discussed in more detail below, we have also shown that the resulting materials can be designed to release conjugates in the presence of varying concentrations of target molecule.

Conjugates

In one aspect, the present disclosure provides conjugates which include two or more separate affinity ligands bound to a non-polymeric framework. In general, the affinity ligands are capable of competing with a target molecule for binding with a multivalent cross-linking agent. Since the conjugates include a synthetic non-polymeric framework they have defined chemical structures and a unique MW (i.e., zero polydispersity). Depending on the end application, the conjugates may also include a therapeutic agent and/or a detectable label. As discussed in more detail below, the affinity ligands, drug, and/or detectable label may be covalently or non-covalently attached to the conjugate framework. In certain embodiments the conjugate framework (i.e., without including the affinity ligands, drug or detectable label) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

General Description of Conjugates

In various embodiments, a conjugate of the present disclosure may have the general formula (I):

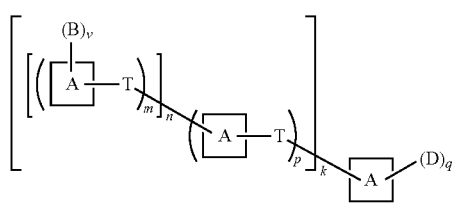

wherein:
each occurrence of

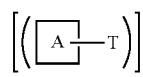

represents a potential branch within the conjugate;

each occurrence of

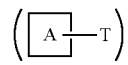

represents a potential repeat within a branch of the conjugate;
each occurrence of

is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently an affinity ligand;
each occurrence of $L^B$ is independently a covalent bond or a group derived from the covalent conjugation of a T with an X;

-D is -T-$L^D$-W;

each occurrence of W is independently a drug or a detectable label;

each occurrence of $L^D$ is independently a covalent bond or a group derived from the covalent conjugation of a T with a W;

k is an integer from 2 to 11, inclusive, defining at least two k-branches within the conjugate;

q is an integer from 1 to 4, inclusive;

k+q is an integer from 3 to 12, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1.

It is to be understood that general formula (I) (and other formulas herein) does not expressly list every hydrogen. For example, if the central

is a $C_6$ aryl group and k+q<6 it will be appreciated that the open position(s) on the $C_6$ aryl ring include a hydrogen.

In general, it will be appreciated that each occurrence of

represents a potential branching node and that the number of branches at each node are determined by the values of k for the central

and n for non-central occurrences of

.

Since $k \geq 2$ the conjugate will always include at least two k-branches. One of ordinary skill will appreciate that because each occurrence of n may be an integer from 0 to 5, the present disclosure contemplates both branched and hyperbranched (e.g., dendrimer-like) embodiments of these conjugates. The proviso which requires that within each k-branch at least one occurrence of n is $\geq 1$ and at least one occurrence of v is $\geq 1$ ensures that every conjugate includes at least two separate k-branches with an occurrence of B (i.e., an affinity ligand).

In certain embodiments, each occurrence of

in a p-bracketed moiety is substituted by a number of n-bracketed moieties corresponding to a value of $n \geq 1$. For example, when $k=2$ and $p=2$ in both k-branches, the conjugate may be of the formula (Ia):

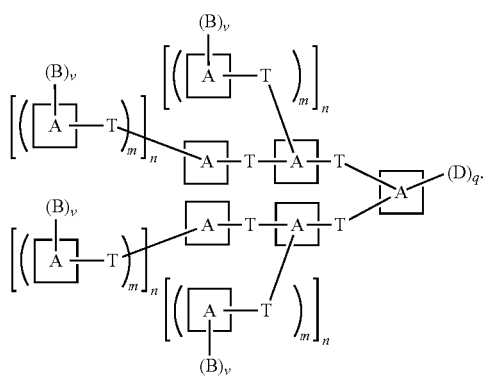

In other embodiments, only terminal occurrences of

in a p-bracketed moiety are substituted by a number of n-bracketed moieties corresponding to a value of $n \geq 1$. For example, when $k=2$ and $p=2$ in both k-branches (and $n=0$ for the first p-bracketed moiety in both k-branches), the conjugate may be of the formula (Ib):

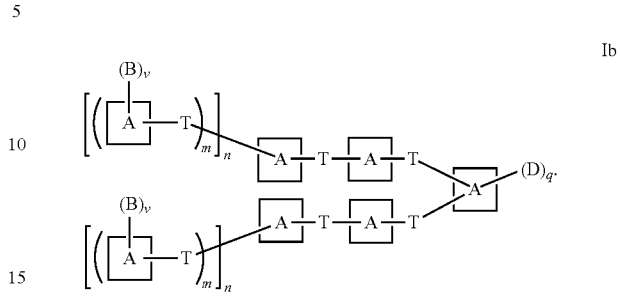

In certain embodiments, each occurrence of

in an m-bracketed moiety is substituted by a number of B moieties corresponding to the value of $v \geq 1$. For example, when $k=2$, each occurrence of $p=1$, and each occurrence of $m=2$, the conjugate may be of the formula (Ic):

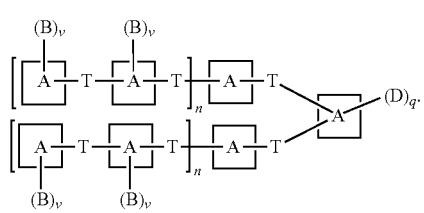

In other embodiments, only terminal occurrences of

in an m-bracketed moiety are substituted by a number of B moieties corresponding to a value of $v \geq 1$. For example, when $k=2$, each occurrence of $p=1$, and each occurrence of $m=2$ (and $v=0$ for the first m-bracketed moiety in each n-branch), the conjugate may be of the formula (Id):

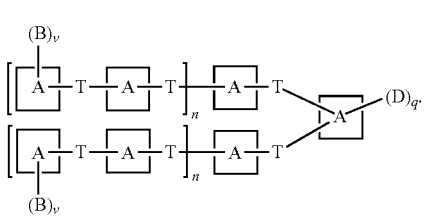

By way of further example, when $q=1$ and $n=1$ in both k-branches of the previous formula, the conjugate may be of the formula (Ie):

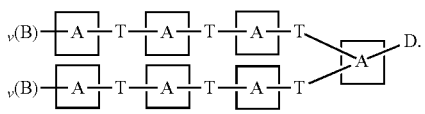

Alternatively, when q=1 and n=2 in both k-branches of the previous formula, the conjugate may be of the formula (If):

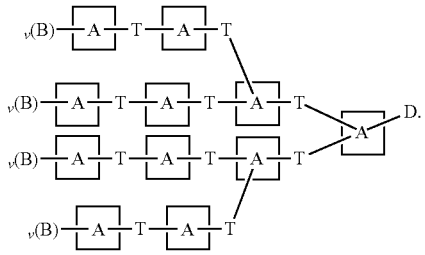

In various embodiments, the present disclosure also provides conjugates which include affinity ligands and/or a drug or detectable label which are non-covalently bound the conjugate framework.

For example, in some embodiments, the present disclosure provides conjugates of any of the foregoing formulas, wherein:

each of

,

T, D, k, q, k+q, p, n, m and v is defined as described above and herein;

—B is -T-$LRP^B$—X;

each occurrence of X is independently an affinity ligand; and each occurrence of $LRP^B$ is independently a ligand-receptor pair which forms a non-covalent bond between T and X with a dissociation constant in human serum of less than 1 pmol/L.

In yet other embodiments, the present disclosure provides conjugates of any of the foregoing formulas, wherein:

each of

,

T, B, k, q, k+q, p, n, m and v is defined as described above and herein;

-D is -T-$LRP^D$—W;

each occurrence of W is independently a drug or a detectable label; and each occurrence of $LRP^D$ is independently a ligand-receptor pair which forms a non-covalent bond between T and W with a dissociation constant in human serum of less than 1 pmol/L.

In other embodiments, the present disclosure provides conjugates of any of the foregoing formulas wherein:

each of

,

T, k, q, k+q, p, n, m and v is defined as described above and herein;

—B is -T-$LRP^B$—X;

each occurrence of X is independently an affinity ligand; each occurrence of $LRP^B$ is independently a ligand-receptor pair which forms a non-covalent bond between T and X with a dissociation constant in human serum of less than 1 pmol/L.

-D is -T-$LRP^D$—W;

each occurrence of W is independently a drug or a detectable label; and each occurrence of $LRP^D$ is independently a ligand-receptor pair which forms a non-covalent bond between T and W with a dissociation constant in human serum of less than 1 pmol/L.

In various embodiments, a conjugate of the present disclosure may have the general formula (II):

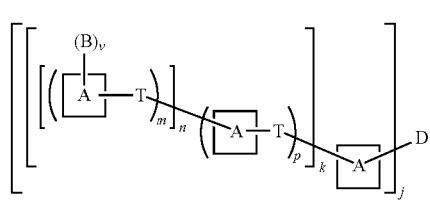

wherein

,

B, T, D, v, m, n, and p are as defined and described herein, k is an integer from 1 to 11, inclusive, and j is an integer from 2 to 4, inclusive. Conjugates of formula (II) may have multiple sites of conjugation of ligand to drug. It will be appreciated that, when q is 1, similar subgenera described to those described above (formulae (Ia) to (If)) can be contemplated by one skilled in the art for conjugates of formula (II) wherein j is 2, 3, or 4.

For purposes of exemplification and for the avoidance of confusion it is to be understood that an occurrence of:

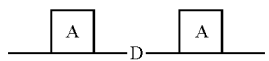

in a conjugate of formula (II) (i.e., when j is 2) could be represented as:

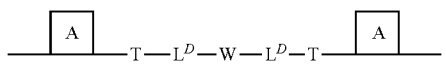

(when the drug is covalently bound to the conjugate framework) or $$\underline{\quad\boxed{A}\quad}\text{—T—LRP}^D\text{—W—LRP}^D\text{—T—}\underline{\quad\boxed{A}\quad}$$

(when the drug is non-covalently bound to the conjugate framework).

Description of Exemplary Groups $$\boxed{A}$$

(node)

In certain embodiments, each occurrence of $$\boxed{A}$$

is independently an optionally substituted group selected from the group consisting of acyl, aliphatic, heteroaliphatic, aryl, heteroaryl, and heterocyclic. In some embodiments, each occurrence of $$\boxed{A}$$

is the same. In some embodiments, the central $$\boxed{A}$$

is different from all other occurrences of $$\boxed{A}.$$

In certain embodiments, all occurrences of $$\boxed{A}$$

are the same except for the central $$\boxed{A}.$$

In some embodiments, $$\boxed{A}$$

is an optionally substituted aryl or heteroaryl group. In some embodiments, $$\boxed{A}$$

is 6-membered aryl. In certain embodiments, $$\boxed{A}$$

is phenyl.

In certain embodiments, $$\boxed{A}$$

is a heteroatom selected from N, O, or S. In some embodiments, $$\boxed{A}$$

is nitrogen atom. In some embodiments, $$\boxed{A}$$

is an oxygen atom. In some embodiments, $$\boxed{A}$$

is sulfur atom. In some embodiments, $$\boxed{A}$$

is a carbon atom.

T (Spacer)

In certain embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In certain embodiments, one, two, three, four, or five methylene units of T are optionally and independently replaced. In certain embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In certain embodiments, one or more methylene units of T is replaced by —C(O)—. In certain embodiments, one or more methylene units of T is replaced by —C(O)N(R)—. In certain embodiments, one or more methylene units of T is replaced by —O—.

In some embodiments, T is

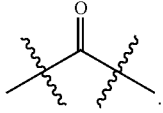 [SMILES: *C(*)=O]

In some embodiments, T is

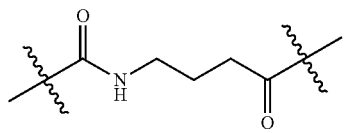

In some embodiments, T is

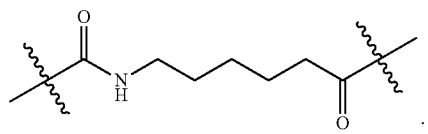 [SMILES: *C(=O)CCCCCNC(*)=O]

In some embodiments, T is

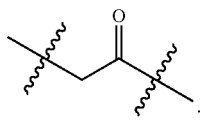 [SMILES: *CC(*)=O]

In some embodiments, T is

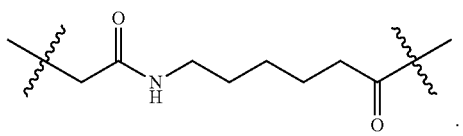 [SMILES: *CC(=O)NCCCCCC(*)=O]

In some embodiments, T is

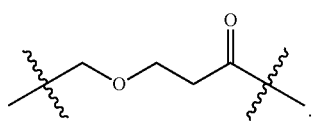 [SMILES: *COCCC(*)=O]

In certain embodiments, each occurrence of T is the same.

In certain embodiments, each occurrence of T (outside groups B and D) is a covalent bond and the conjugate is of the general formula (IV) or (V):

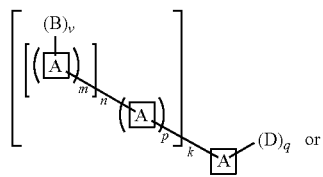  IV

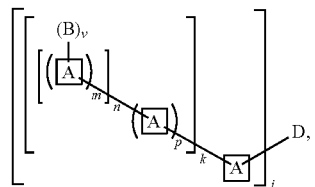  V wherein

,

B, D, v, m, n, p, k, and j are as defined and described for formula (I) or (II), respectively.

In certain embodiments of general formulae (IV) and (V), each occurrence of

except for the central

is a covalent bond, each occurrence of v=1, and the conjugate is of the formula (VI) or (VII):

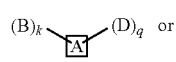  VI

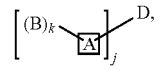  VII wherein

,

B, D, q, k, and j are as defined and described for formula (I) or (II), respectively.

In certain such embodiments for formula (VI), k=2 and q=1.
In other embodiments, k=3 and q=1.
In other embodiments, k=2 and q=2.
In certain such embodiments for formula (VII), k=1 and j=2.
In other embodiments, k=2 and j=2.
In other embodiments, k=3 and j=2.
In other embodiments, k=1 and j=3.
In other embodiments, k=2 and j=3.
In other embodiments, k=3 and j=3.

In some embodiments, the present disclosure provides conjugates of general formula (VIa):

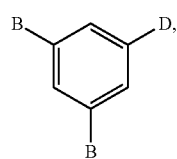
VIa wherein B and D are as defined and described herein.

For example, in some embodiments, the present disclosure provides conjugates of formula:

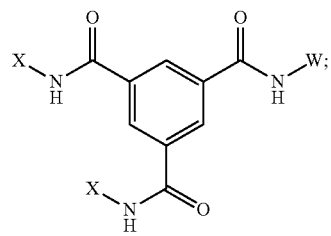

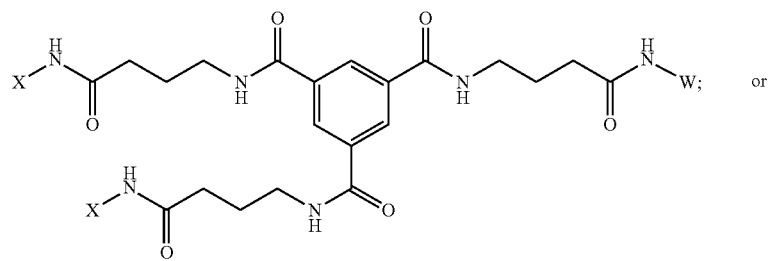  or

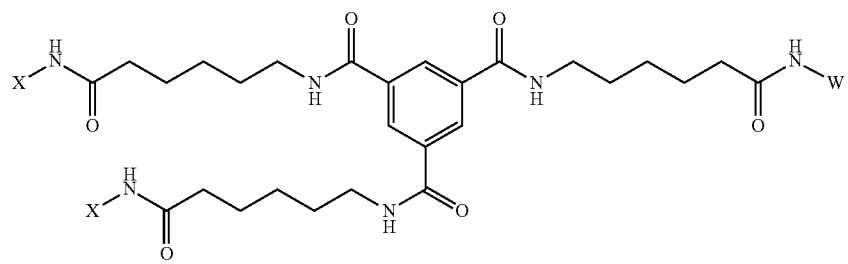

wherein W and X is as defined and described herein.

In some embodiments, the present disclosure provides conjugates of general formula (VIb):

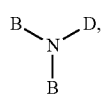
VIb wherein B and D are as defined and described herein.

For example, in some embodiments, the present disclosure provides conjugates of formula:

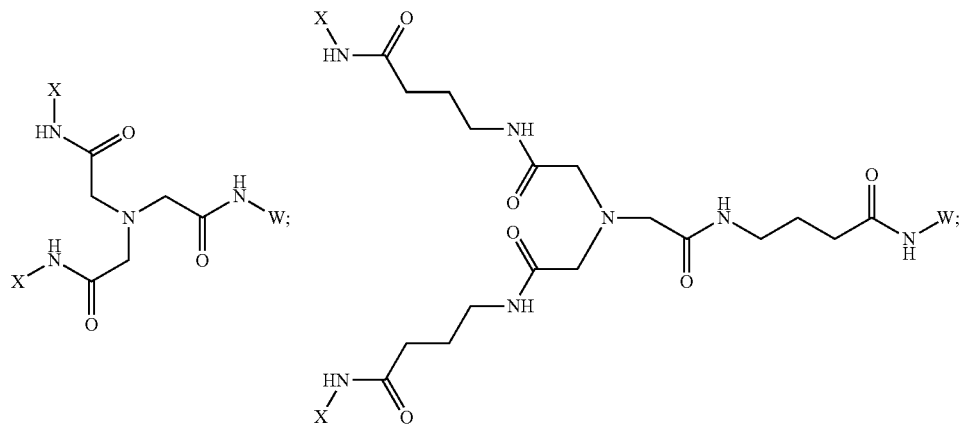
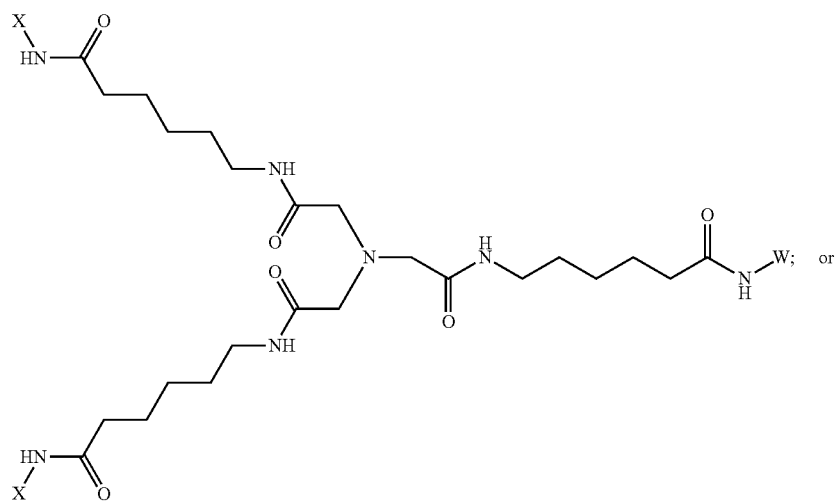
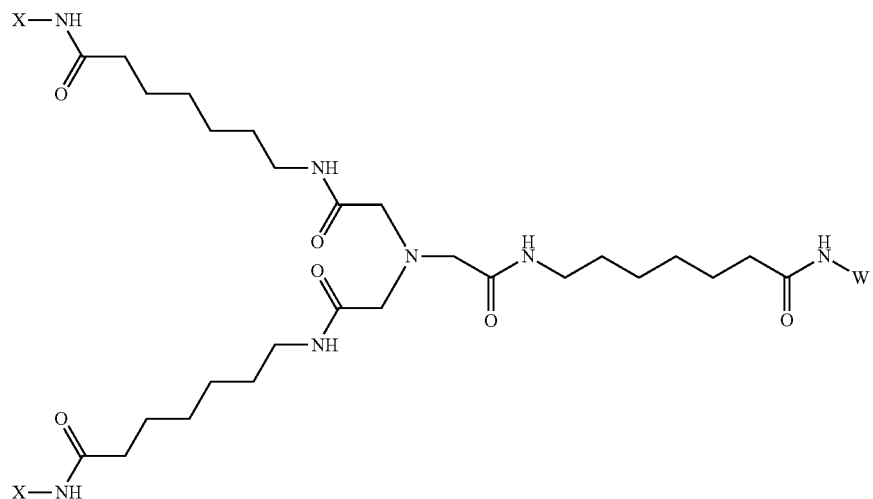
wherein W and X are as defined and described herein.

In some embodiments, the present disclosure provides conjugates of general formula (VIc):

wherein B and D are as defined and described herein.

For example, in some embodiments, the present disclosure provides conjugates of formula:

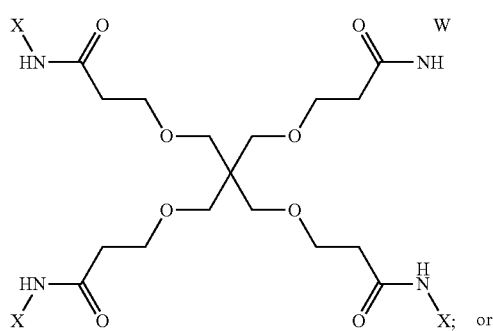

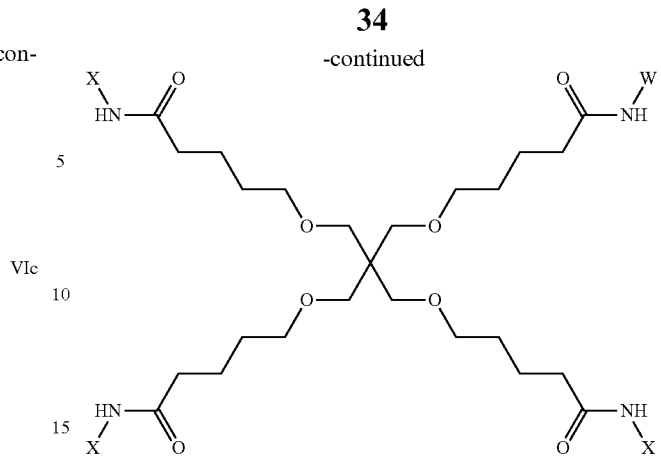

wherein W and X are as defined and described herein.

It will be appreciated that similar subgenera to those of formulae (VIa), (VIb), and (VIc), and species thereof, can be contemplated by one skilled in the art for conjugates of formula (VII) wherein j is 2, 3, or 4. For example, when j is 2, in certain embodiments, the present disclosure provides conjugates of formula:

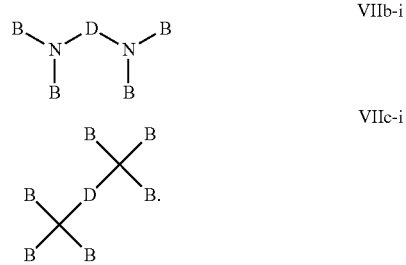

wherein B and D are as defined and described herein.

In certain embodiments, the present disclosure provides conjugates of formula:

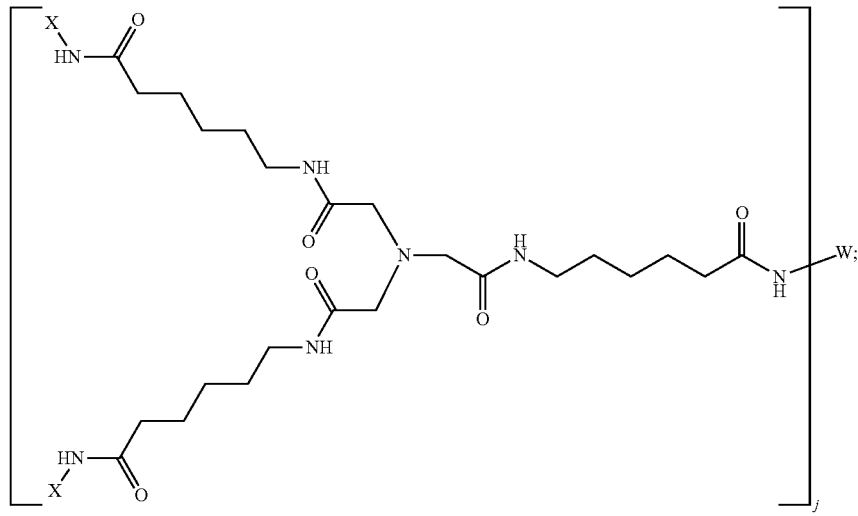

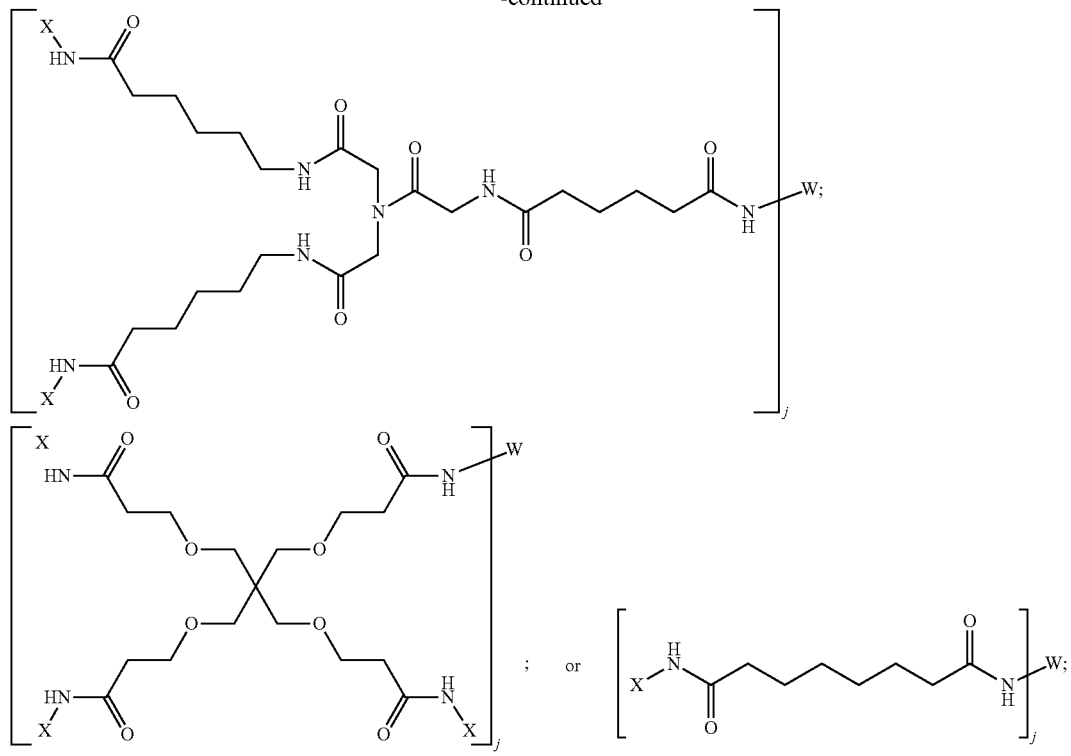

wherein W, X, and j are as defined and described herein.

B (Affinity Ligand)

In various embodiments, —B is -T-$L^B$-X where X is an affinity ligand; and $L^B$ is a covalent bond or a group derived from the covalent conjugation of an X with a T. In general, the affinity ligand is capable of competing with the target molecule for binding with the multivalent cross-linking agent. In certain embodiments, the relative affinity of the conjugate and target molecule for the cross-linking agent is in the range of 1:1 to 100:1 (where a relative affinity of 100:1 means that, in an equilibrium mixture of conjugate, target molecule and cross-linking agent (in pH 7 HEPES buffered saline at 37 C), the cross-linking agent will bind about equal molar amounts of conjugate and target molecule if the concentration of target molecule is 100× the concentration of conjugate). In certain embodiments, the relative affinity is in the range of 1:1 to 50:1, 1:1 to 10:1, 1:1 to 5:1 or 1:1 to 2:1. The two or more separate affinity ligands may have the same or different chemical structures. For example, the two or more separate affinity ligands may have the same chemical structure as the target molecule (e.g., glucose) or may be a chemically related species of the target molecule. For example, when the target molecule is glucose the affinity ligands may include a saccharide. Thus, in certain embodiments, the affinity ligands are capable of competing with glucose for binding to a multivalent glucose binding molecule (e.g., without limitation Con A, mannan-binding lectin or MBL, etc.).

In certain embodiments, the affinity ligand is of formula (IIIa) or (IIIb):

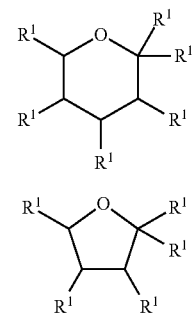

wherein:

each $R^1$ is independently hydrogen, —$OR^y$, —$N(R^y)_2$, —$SR^y$, —O—Y, -G-Z, or —$CH_2R^x$;

each $R^x$ is independently hydrogen, —$OR^y$, —$N(R^y)_2$, —$SR^y$, or —O—$^y$;

each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$;

each Y is independently a monosaccharide, disaccharide, or trisaccharide;

each G is independently a covalent bond or an optionally substituted $C_{1-9}$ alkylene, wherein one or more methylene units of G is optionally replaced by —O—, —S—, —$N(R^2)$—, —C(O)—, —OC(O)—, —C(O)O—, —C(O)N($R^2$)—, —N($R^2$)C(O)—, —N($R^2$)C(O)N($R^2$)—, —$SO_2$—, —$SO_2N(R^2)$—, —N($R^2$)$SO_2$—, or —N($R^2$)$SO_2N(R^2)$—;

each Z is independently halogen, —$N(R^2)_2$, —$OR^2$, —$SR^2$, —$N_3$, —C≡$CR^2$, —$CO_2R^2$, —C(O)$R^2$, or —$OSO_2R^2$; and each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the affinity ligand of formula (IIIa) or (IIIb) is a monosaccharide. In certain embodiments, the affinity ligand is a disaccharide. In certain embodiments, the affinity ligand is a trisaccharide. In certain embodiments, the affinity ligand is a tetrasaccharide. In certain embodiments, the affinity ligand comprises no more than four saccharide moieties.

As defined generally above, each $R^1$ is independently hydrogen, $-OR^y$, $-N(R^y)_2$, $-SR^y$, $-O-Y$, -G-Z, or $-CH_2R^x$. In certain embodiments, $R^1$ is hydrogen. In certain embodiments, $R^1$ is $-OH$. In other embodiments, $R^1$ is $-NHC(O)CH_3$. In certain embodiments, $R^1$ is $-O-Y$. In certain other embodiments, $R^1$ is -G-Z. In some embodiments, $R^1$ is $-CH_2OH$. In other embodiments, $R^1$ is $-CH_2-O-Y$. In yet other embodiments, $R^1$ is $-NH_2$. One of ordinary skill in the art will appreciate that each $R^1$ substituent in formula (IIIa) or (IIIb) may be of (R) or (S) stereochemistry.

As defined generally above, each $R^x$ is independently hydrogen, $-OR^y$, $-N(R^y)_2$, $-SR^y$, or $-O-Y$. In some embodiments, $R^x$ is hydrogen. In certain embodiments, $R^x$ is $-OH$. In other embodiments, $R^x$ is $-O-Y$.

As defined generally above, each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$. In some embodiments, $R^y$ is hydrogen. In other embodiments, $R^y$ is $-R^2$. In some embodiments, $R^y$ is $-C(O)R^2$. In certain embodiments, $R^y$ is acetyl. In other embodiments, $R^y$ is $-SO_2R^2$, $-S(O)R^2$, $-P(O)(OR^2)_2$, $-CO_2R^2$, or $-C(O)N(R^2)_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of $-O-Y$ through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by $-O-$, $-S-$, $-N(R^2)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$. In some embodiments, G is a covalent bond. In certain embodiments, G is $-O-C_{1-8}$ alkylene. In certain embodiments, G is $-OCH_2CH_2-$.

As defined generally above, each Z is independently halogen, $-N(R^2)_2$, $-OR^2$, $-SR^2$, $-N_3$, $-C\equiv CR^2$, $-CO_2R^2$, $-C(O)R^2$, or $-OSO_2R^2$. In some embodiments, Z is a halogen or $-OSO_2R^2$. In other embodiments, Z is $-N_3$ or $-C\equiv CR^2$. In certain embodiments, Z is $-N(R^2)_2$, $-OR^2$, or $-SR^2$. In certain embodiments, Z is $-SH$. In certain embodiments, Z is $-NH_2$. In certain embodiments, -G-Z is $-OCH_2CH_2NH_2$.

In some embodiments, the $R^1$ substituent on the C1 carbon of formula (IIIa) is -G-Z to give a compound of formula (IIIa-i):

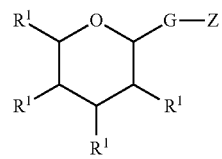

wherein $R^1$, G, and Z are as defined and described herein.

In some embodiments, the ligand is of formula (IIIa-ii):

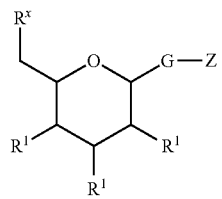

wherein $R^1$, $R^x$, G, and Z are as defined and described herein.

In certain embodiments where the target molecule is glucose, it may be advantageous for the affinity ligands to have a different chemical structure from glucose, e.g., in order to fine tune the response of a glucose-responsive material. For example, in certain embodiments, one might use an affinity ligand that includes one or more of the following: glucose, sucrose, maltose, mannose, derivatives of these (e.g., glucosamine, mannosamine, methylglucose, methylmannose, ethylglucose, ethylmannose, etc.) and/or higher order combinations of these (e.g., a bimannose, a linear and/or branched trimannose, etc.). In certain embodiments, the affinity ligand includes a monosaccharide. In certain embodiments, the affinity ligand includes a disaccharide. In certain embodiments, the affinity ligand includes a trisaccharide. In certain embodiments, the affinity ligand includes a polysaccharide. In some embodiments, the affinity ligand includes a saccharide and one or more amine groups. In some embodiments, the affinity ligand is aminoethylglucose (AEG). In some embodiments, the affinity ligand is aminoethylmannose (AEM). In some embodiments, the affinity ligand is aminoethylbimannose (AEBM). In some embodiments, the affinity ligand is aminoethyltrimannose (AETM). In some embodiments, the affinity ligand is β-aminoethyl-N-acetylglucosamine (AEGA). In some embodiments, the affinity ligand is aminoethylfucose (AEF). In other embodiments, the affinity ligand is D-glucosamine (GA). In certain embodiments, a saccharide ligand is of the "D" configuration. In other embodiments, a saccharide ligand is of the "L" configuration. Below we show the structures of these exemplary ligands. Other exemplary ligands will be recognized by those skilled in the art.

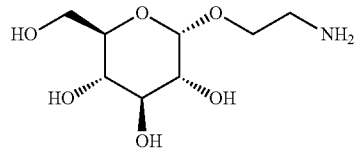

AEG

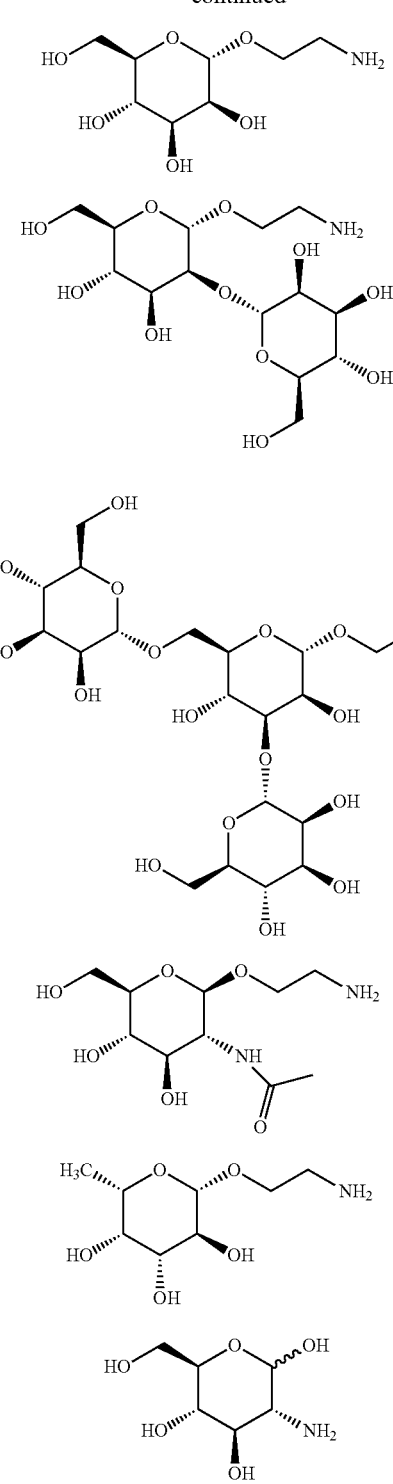

AEM

AEBM

AETM

AEGA

AEF

GA

As discussed in more detail below, the affinity ligands may be naturally present within the framework of the conjugate (e.g., as part of a polymer backbone or as a side group of a monomer). Alternatively (or additionally) affinity ligands may be artificially incorporated into the conjugate framework (e.g., in the form of a chemical group that is synthetically added to a conjugate framework). In certain embodiments, a conjugate may include a framework which comprises 5 or more, 10 or more, 20 or more, 25 or more, 50 or more, or 100 or more affinity ligands. In certain embodiments, a conjugate may include a framework which comprises 2-5, 2-10, 2-20, 2-25, 2-50 or 2-100 affinity ligands. In certain embodiments, a conjugate may include a framework which comprises as few as 2, 3 or 4 separate affinity ligands, e.g., 2, 3 or 4 AEM, AEBM or AETM ligands (including mixtures thereof).

Methods for conjugating affinity ligands to a conjugate framework are discussed in more detail below. In certain embodiments, when the affinity ligands include a saccharide, the conjugation (whether direct or indirect) involves the C1, C2 or C6 position of the saccharide. In certain embodiments, the conjugation involves the C1 position. The C1 position is also referred to as the anomeric carbon and may be connected to the conjugate framework in the alpha or beta conformation. In certain embodiments, the C1 position is configured as the alpha anomer. In other embodiments, the C1 position is configured as the beta anomer.

D (Drug)

In various embodiments, -D is -T-$L^D$-W where W is a drug and $L^D$ is a covalent bond or a group derived from the covalent conjugation of a W with a T.

For example, a drug may be included when the material is to be used for therapeutic purposes, e.g., to controllably deliver a drug in a patient. It is to be understood that a conjugate can comprise any drug. A conjugate can comprise more than one copy of the same drug and/or can comprise more than one type of drug. The conjugates are not limited to any particular drug and may include small molecule drugs or biomolecular drugs. In general, the drug(s) used will depend on the disease or disorder to be treated.

For example, without limitation, in various embodiments a conjugate can comprise any one of the following drugs: diclofenac, nifedipine, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecainide, alprenolol, propoanolol, nadolol, pindolol, oxprenolol, labetalol, tirnolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephydroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metanamine, chloroquin, hydroxichloroquin, tinidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlomethiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenyloine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfuram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, ornidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, calcitonin, etc. It is to be understood that this list is intended to be exemplary and that any drug, whether known or later discovered, may be used in a conjugate of the present disclosure.

In various embodiments, a conjugate may include a hormonal drug which may be peptidic or non-peptidic, e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone, growth hormone-releasing hormone, human chorionic gonadotropin, histamine, human placental lactogen, insulin, insulin-like growth factor, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone (or thyrotropin), thyrotropin-releasing hormone, thyroxine, triiodothyronine, vasopressin, etc. In certain embodiments, the hormone may be selected from glucagon, insulin, insulin-like growth factor, leptin, thyroid-stimulating hormone, thyrotropin-releasing hormone (or thyrotropin), thyrotropin-releasing hormone, thyroxine, and triiodothyronine. It is to be understood that this list is intended to be exemplary and that any hormonal drug, whether known or later discovered, may be used in a conjugate of the present disclosure.

In various embodiments, a conjugate may include a thyroid hormone.

In various embodiments, a conjugate may include an antidiabetic drug (i.e., a drug which has a beneficial effect on patients suffering from diabetes).

In various embodiments, a conjugate may include an insulin molecule. By "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids). In general, a bioactive mutant form of insulin will typically differ from wild-type insulin by 1-10 (e.g., from 1-5 or 1-2) amino acid substitutions, additions or deletions. The wild-type sequence of human insulin (A-chain and B-chain) is shown below and in FIG. 29.

A-Chain
(SEQ ID NO: 1):     GIVEQCCTSICSLYQLENYCN

B-Chain
(SEQ ID NO: 2):     FVNQHLCGSHLVEALYLVCGERGFFYTPKT

Human insulin differs from rabbit, porcine, bovine, and sheep insulin only in amino acids A8, A9, A10, and B30 (see table below).

|  | Amino Acid Position | | | |
| --- | --- | --- | --- | --- |
| Insulin | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}$ $Arg^{B32}$-human insulin, $Arg^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des (B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($His^{B10} \rightarrow Asp^{B10}$); replacement of the phenylalanine residue at position B1 with aspartic acid ($Phe^{B1} \rightarrow Asp^{B1}$); replacement of the threonine residue at position B30 with alanine ($Thr^{B30} \rightarrow Ala^{B30}$); replacement of the tyrosine residue at position B26 with alanine ($Tyr^{B26} \rightarrow Ala^{B26}$); and replacement of the serine residue at position B9 with aspartic acid ($Ser^{B9} \rightarrow Asp^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $Thr^{B30}$ has been deleted, and a C14 fatty acid chain (myristic acid) has been attached to $Lys^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

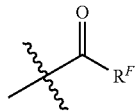

where $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of Lys$^{B28}$ is conjugated to the fatty acid moiety. In certain embodiments, position B3 of the insulin molecule is Lys and the epsilon-amino group of Lys$^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20). For example, insulin detemir (LEVEMIR®) is a long acting insulin mutant in which Thr$^{B30}$ has been deleted, and a C14 fatty acid chain (myristic acid) is attached to Lys$^{B29}$.

In certain embodiments, an insulin molecule of the present disclosure comprises the mutations and/or chemical modifications of one of the following insulin molecules: Lys$^{B28}$Pro$^{B29}$-human insulin (insulin lispro), Asp$^{B28}$-human insulin (insulin aspart), Lys$^{B3}$Glu$^{B29}$-human insulin (insulin glulisine), Arg$^{B31}$Arg$^{B32}$-human insulin (insulin glargine), N$^{\epsilon B29}$-myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg$^{B31}$Arg$^{B32}$-human insulin, Arg$^{A0}$Arg$^{B31}$Arg$^{B32}$-human insulin, Arg$^{A0}$Gly$^{A21}$Arg$^{B31}$Arg$^{B32}$-human insulin, des(B30)-human insulin, des(B27)-human insulin, des (B28-B30)-human insulin, des(B1)-human insulin, des (B1-B3)-human insulin.

In certain embodiments, an insulin molecule of the present disclosure comprises the mutations and/or chemical modifications of one of the following insulin molecules: N$^{\epsilon B29}$-palmitoyl-human insulin, N$^{\epsilon B29}$-myrisotyl-human insulin, N$^{\epsilon B28}$-palmitoyl-Lys$^{B28}$Pro$^{B29}$-human insulin, N$^{\epsilon B28}$-myristoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-palmitoyl-des(B30)-human insulin, N$^{\epsilon B30}$-myristoyl-Thr$^{B29}$Lys$^{B30}$-human insulin, N$^{\epsilon B30}$-palmitoyl-Thr$^{B29}$Lys$^{B30}$-human insulin, N$^{\epsilon B29}$-(N-palmitoyl-γ-glutamyl)-des(B30)-human insulin, N$^{\epsilon B29}$-(N-lithocolyl-γ-glutamyl)-des(B30)-human insulin, N$^{\epsilon B29}$-(ω-carboxyheptadecanoyl)-des(B30)-human insulin, N$^{\epsilon B29}$-(ω-carboxyheptadecanoyl)-human insulin.

In certain embodiments, an insulin molecule of the present disclosure comprises the mutations and/or chemical modifications of one of the following insulin molecules: N$^{\epsilon B29}$-octanoyl-human insulin, N$^{\epsilon B29}$-myristoyl-Gly$^{A21}$Arg$^{B31}$Arg$^{B31}$-human insulin, N$^{\epsilon B29}$-myristoyl-Gly$^{A21}$Gln$^{B3}$Arg$^{B31}$Arg$^{B32}$-human insulin, N$^{\epsilon B29}$-myristoyl-Arg$^{A0}$Gly$^{A21}$Arg$^{B31}$Arg$^{B32}$-human insulin, N$^{\epsilon B29}$, Arg$^{A0}$Gly$^{A21}$Gln$^{B3}$Arg$^{B31}$Arg$^{B32}$-human insulin, N$^{\epsilon B29}$-myristoyl-Arg$^{A0}$Gly$^{A21}$Asp$^{B3}$Arg$^{B31}$Arg$^{B32}$-human insulin, N$^{\epsilon B29}$-myristoyl-Arg$^{B31}$Arg$^{B32}$-human insulin, N$^{\epsilon B29}$-myristoyl-Arg$^{A0}$Arg$^{B31}$Arg$^{B32}$-human insulin, N$^{\epsilon B29}$-octanoyl-Gly$^{A21}$Arg$^{B31}$Arg$^{B32}$-human insulin, N$^{\epsilon B29}$-octanoyl-Gly$^{A21}$Gln$^{B3}$Arg$^{B31}$Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B3}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B32}$-human insulin.

In certain embodiments, an insulin molecule of the present disclosure comprises the mutations and/or chemical modifications of one of the following insulin polypeptides: N$^{\epsilon B28}$-myristoyl-Gly$^{A21}$Lys$^{B28}$Pro$^{B29}$Arg$^{B31}$Arg$^{B32}$-human insulin, N$^{\epsilon B28}$-myristoyl-Gly$^{A21}$Gln$^{B3}$Lys$^{B28}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B31}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B31}$Arg$^{B32}$-human insulin, N$^{\epsilon B28}$-Octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-octanoyl-Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Lys$^{B28}$Pro$^{B29}$Arg$^{B31}$Arg$^{B32}$-human insulin, N$^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-octanoyl-Lys$^{B28}$Pro$^{B29}$Arg$^{B31}$Arg$^{B32}$-human insulin, N$^{\epsilon B28}$-octanoyl-Arg$^{A0}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B29}$-tridecanoyl-des(B30)-human insulin, N$^{\epsilon B29}$-tetradecanoyl-des(B30)-human insulin, N$^{\epsilon B29}$-decanoyl-des (B30)-human insulin, N$^{\epsilon B29}$-dodecanoyl-des(B30)-human insulin, N$^{\epsilon B29}$-tridecanoyl-Gly$^{A21}$-des(B30)-human insulin, N$^{\epsilon B29}$-tetradecanoyl-Gly$^{A21}$-des(B30)-human insulin, N$^{\epsilon B29}$-decanoyl-Gly$^{A21}$-des(B30)-human insulin, N$^{\epsilon B29}$-dodecanoyl-Gly$^{A21}$-des(B30)-human insulin, N$^{\epsilon B29}$-tridecanoyl-Gly$^{A21}$Gln$^{B3}$-des(B30)-human insulin, N$^{\epsilon B29}$-tetradecanoyl-Gly$^{A21}$Gln$^{B3}$-des(B30)-human insulin, N$^{\epsilon B29}$-decanoyl-Gly$^{A21}$-Gln$^{B3}$-des(B30)-human insulin, N$^{\epsilon B29}$-dodecanoyl-Gly$^{A21}$-Gln$^{B3}$-des(B30)-human insulin, N$^{\epsilon B29}$-tridecanoyl-Ala$^{A21}$-des(B30)-human insulin, N$^{\epsilon B29}$-tetradecanoyl-Ala$^{A21}$-des(B30)-human insulin, N$^{\epsilon B29}$-decanoyl-Ala$^{A21}$-des(B30)-human insulin, N$^{\epsilon B29}$-dodecanoyl-Ala$^{A21}$-des(B30)-human insulin, N$^{\epsilon B29}$-tridecanoyl-Ala$^{A21}$-Gln$^{B3}$-des(B30)-human insulin, N$^{\epsilon B29}$-tetradecanoyl-Ala$^{A21}$Gln$^{B3}$-des(B30)-human insulin, N$^{\epsilon B29}$-decanoyl-Ala$^{A21}$Gln$^{B3}$-des(B30)-human insulin, N$^{\epsilon B29}$-dodecanoyl-Ala$^{A21}$Gln$^{B3}$-des (B30)-human insulin, N$^{\epsilon B29}$-tridecanoyl-Gln$^{B3}$-des(B30)-human insulin, N$^{\epsilon B29}$-tetradecanoyl-Gln$^{B3}$-des(B30)-human insulin, N$^{\epsilon B29}$-decanoyl-Gln$^{B3}$-des(B30)-human insulin, N$^{\epsilon B29}$-dodecanoyl-Gln$^{B3}$-des(B30)-human insulin.

In certain embodiments, an insulin molecule of the present disclosure comprises the mutations and/or chemical modifications of one of the following insulin molecules: N$^{\epsilon B29}$-tridecanoyl-Gly$^{A21}$-human insulin, N$^{\epsilon B29}$-tetradecanoyl-Gly$^{A21}$-human insulin, N$^{\epsilon B29}$-decanoyl-Gly$^{A21}$-human insulin, N$^{\epsilon B29}$-dodecanoyl-Gly$^{A21}$-human insulin, N$^{\epsilon B29}$-tridecanoyl-Ala$^{A21}$-human insulin, N$^{\epsilon B29}$-tetradecanoyl-Ala$^{A21}$-human insulin, N$^{\epsilon B29}$-decanoyl-Ala$^{A21}$-human insulin, N$^{\epsilon B29}$-dodecanoyl-Ala$^{A21}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$-human insulin, N$^{\epsilon B29}$-tetradecanoyl-Gly$^{A21}$Gln$^{B3}$-human insulin, N$^{\epsilon B29}$-decanoyl-Gly$^{A21}$Gln$^{B3}$-human insulin, N$^{\epsilon B29}$-dodecanoyl-Gly$^{A21}$Gln$^{B3}$-human insulin, N$^{\epsilon B29}$-tridecanoyl-Ala$^{A21}$Gln$^{B3}$-human insulin, N$^{\epsilon B29}$-tetradecanoyl- Ala$^{A21}$Gln$^{B3}$-human insulin, N$^{\epsilon B29}$-decanoyl-Ala$^{A21}$Gln$^{B3}$-human insulin, N$^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$-human insulin, N$^{\epsilon B29}$-tetradecanoyl-Gln$^{B3}$-human insulin, N$^{\epsilon B29}$-decanoyl-Gln$^{B3}$-human insulin, N$^{\epsilon B29}$-dodecanoyl-Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Glu$^{B30}$-human insulin, N$^{\epsilon B29}$-tetradecanoyl-Glu$^{B30}$-human insulin, N$^{\epsilon B29}$-decanoyl-Glu$^{B30}$-human insulin, N$^{\epsilon B29}$-dodecanoyl-Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Glu$^{B30}$-human insulin, N$^{\epsilon B29}$-tetradecanoyl-Gly$^{A21}$Glu$^{B30}$-human insulin, N$^{\epsilon B29}$-decanoyl-Gly$^{A21}$Glu$^{B30}$-human insulin, N$^{\epsilon B29}$-dodecanoyl-Gly$^{A21}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$Glu$^{B30}$-human insulin, N$^{\epsilon B29}$-tetradecanoyl-Gly$^{A21}$Gln$^{B3}$Glu$^{B30}$-human insulin, N$^{\epsilon B29}$-decanoyl-Gly$^{A21}$Gln$^{B3}$Glu$^{B30}$-human insulin, N$^{\epsilon B29}$-dodecanoyl-Gly$^{A21}$Gln$^{B3}$Glu$^{B30}$-human insulin, N$^{\epsilon B29}$-tridecanoyl-Ala$^{A21}$Glu$^{B30}$-human insulin, N$^{\epsilon B29}$-tetradecanoyl-Ala$^{A21}$Glu$^{B30}$-human insulin, N$^{\epsilon B29}$-decanoyl-Ala$^{A21}$Glu$^{B30}$-human insulin, N$^{\epsilon B29}$-dodecanoyl-Ala$^{A21}$Glu$^{B30}$-human insulin, N$^{\epsilon B29}$-tridecanoyl-Ala$^{A21}$Gln$^{B3}$Glu$^{B30}$-human insulin, N$^{\epsilon B29}$-tetradecanoyl-Ala$^{A21}$Gln$^{B3}$Glu$^{B30}$-human insulin, N$^{\epsilon B29}$-decanoyl-Ala$^{A21}$Gln$^{B3}$Glu$^{B30}$-human insulin, N$^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$Glu$^{B30}$-human insulin, N$^{\epsilon B29}$-tetradecanoyl-Gln$^{B3}$Glu$^{B30}$-human insulin, N$^{\epsilon B29}$-decanoyl-Gln$^{B3}$Glu$^{B30}$-human insulin, N$^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-formyl-human insulin, N$^{\alpha B1}$-formyl-human insulin, N$^{\alpha A1}$-formyl-human insulin, N$^{\epsilon B29}$-formyl-N$^{\alpha B1}$-formyl-human insulin, N$^{\epsilon B29}$-formyl-N$^{\alpha A1}$-formyl-human insulin, N$^{\alpha A1}$-formyl-N$^{\alpha B1}$-formyl-human insulin, N$^{\epsilon B29}$-formyl-N$^{\alpha A1}$-formyl-N$^{\alpha B1}$-formyl-human insulin.

In certain embodiments, an insulin molecule of the present disclosure comprises the mutations and/or chemical modifications of one of the following insulin molecules: N$^{\epsilon B29}$-acetyl-human insulin, N$^{\alpha B1}$-acetyl-human insulin, N$^{\alpha A1}$-acetyl-human insulin, N$^{\epsilon B29}$-acetyl-N$^{\alpha B1}$-acetyl-human insulin, N$^{\epsilon B29}$-acetyl-N$^{\alpha A1}$-acetyl-human insulin, N$^{\alpha A1}$-acetyl-N$^{\alpha B1}$-acetyl-human insulin, N$^{\epsilon B29}$-acetyl-N$^{\alpha A1}$-acetyl-N$^{\alpha B1}$-acetyl-human insulin.

In certain embodiments, an insulin molecule of the present disclosure comprises the mutations and/or chemical modifications of one of the following insulin molecules: N$^{\epsilon B29}$-propionyl-human insulin, N$^{\alpha B1}$-propionyl-human insulin, N$^{\alpha A1}$-propionyl-human insulin, N$^{\epsilon B29}$-acetyl-N$^{\alpha B1}$-propionyl-human insulin, N$^{\epsilon B29}$-propionyl-N$^{\alpha A1}$-propionyl-human insulin, N$^{\alpha A1}$-propionyl-N$^{\alpha B1}$-propionyl-human insulin, N$^{\epsilon B29}$-propionyl-N$^{\alpha A1}$-propionyl-N$^{\alpha B1}$-propionyl-human insulin.

In certain embodiments, an insulin molecule of the present disclosure comprises the mutations and/or chemical modifications of one of the following insulin molecules: N$^{\epsilon B29}$-butyryl-human insulin, N$^{\alpha B1}$-butyryl-human insulin, N$^{\alpha A1}$-butyryl-human insulin, N$^{\epsilon B29}$-butyryl-N$^{\alpha B1}$-butyryl-human insulin, N$^{\epsilon B29}$-butyryl-N$^{\alpha A1}$-butyryl-human insulin, N$^{\alpha A1}$-butyryl-N$^{\alpha B1}$-butyryl-human insulin, N$^{\epsilon B29}$-butyryl-N$^{\alpha A1}$-butyryl-N$^{\alpha B1}$-butyryl-human insulin.

In certain embodiments, an insulin molecule of the present disclosure comprises the mutations and/or chemical modifications of one of the following insulin molecules: N$^{\epsilon B29}$-pentanoyl-human insulin, N$^{\alpha B1}$-pentanoyl-human insulin, N$^{\alpha A1}$-pentanoyl-human insulin, N$^{\epsilon B29}$-pentanoyl-N$^{\alpha B1}$-pentanoyl-human insulin, N$^{\epsilon B29}$-pentanoyl-N$^{\alpha A1}$-pentanoyl-human insulin, N$^{\alpha A1}$-pentanoyl-N$^{\alpha B1}$-pentanoyl-human insulin, N$^{\epsilon B29}$-pentanoyl-N$^{\alpha A1}$-pentanoyl-N$^{\alpha B1}$-pentanoyl-human insulin.

In certain embodiments, an insulin molecule of the present disclosure comprises the mutations and/or chemical modifications of one of the following insulin molecules: N$^{\epsilon B29}$-hexanoyl-human insulin, N$^{\alpha B1}$-hexanoyl-human insulin, N$^{\alpha A1}$-hexanoyl-human insulin, N$^{\epsilon B29}$-hexanoyl-N$^{\alpha B1}$-hexanoyl-human insulin, N$^{\epsilon B29}$-hexanoyl-N$^{\alpha A1}$-hexanoyl-human insulin, N$^{\alpha A1}$-hexanoyl-N$^{\alpha B1}$-hexanoyl-human insulin, N$^{\epsilon B29}$-hexanoyl-N$^{\alpha A1}$-hexanoyl-N$^{\alpha B1}$-hexanoyl-human insulin.

In certain embodiments, an insulin molecule of the present disclosure comprises the mutations and/or chemical modifications of one of the following insulin molecules: N$^{\epsilon B29}$-heptanoyl-human insulin, N$^{\alpha B1}$-heptanoyl-human insulin, N$^{\alpha A1}$-heptanoyl-human insulin, N$^{\epsilon B29}$-heptanoyl-N$^{\alpha B1}$-heptanoyl-human insulin, N$^{\epsilon B29}$-heptanoyl-N$^{\alpha A1}$-heptanoyl-human insulin, N$^{\alpha A1}$-heptanoyl-N$^{\alpha B1}$-heptanoyl-human insulin, N$^{\epsilon B29}$-heptanoyl-N$^{\alpha A1}$-heptanoyl-N$^{\alpha B1}$-heptanoyl-human insulin.

In certain embodiments, an insulin molecule of the present disclosure comprises the mutations and/or chemical modifications of one of the following insulin molecules: N$^{\alpha B1}$-octanoyl-human insulin, N$^{\alpha A1}$-octanoyl-human insulin, N$^{\epsilon B29}$-octanoyl-N$^{\alpha B1}$-octanoyl-human insulin, N$^{\epsilon B29}$-octanoyl-N$^{\alpha A1}$-octanoyl-human insulin, N$^{\alpha A1}$-octanoyl-N$^{\alpha B1}$-octanoyl-human insulin, N$^{\epsilon B29}$-octanoyl-N$^{\alpha A1}$-octanoyl-N$^{\alpha B1}$-octanoyl-human insulin.

In certain embodiments, an insulin molecule of the present disclosure comprises the mutations and/or chemical modifications of one of the following insulin molecules: N$^{\epsilon B29}$-nonanoyl-human insulin, N$^{\alpha B1}$-nonanoyl-human insulin, N$^{\alpha A1}$-nonanoyl-human insulin, N$^{\epsilon B29}$-nonanoyl-N$^{\alpha B1}$-nonanoyl-human insulin, N$^{\epsilon B29}$-nonanoyl-N$^{\alpha A1}$-nonanoyl-human insulin, N$^{\alpha A1}$-nonanoyl-N$^{\alpha B1}$-nonanoyl-human insulin, N$^{\epsilon B29}$-nonanoyl-N$^{\alpha A1}$-nonanoyl-N$^{\alpha B1}$-nonanoyl-human insulin.

In certain embodiments, an insulin molecule of the present disclosure comprises the mutations and/or chemical modifications of one of the following insulin molecules: N$^{\epsilon B29}$-decanoyl-human insulin, N$^{\alpha B1}$-decanoyl-human insulin, N$^{\alpha A1}$-decanoyl-human insulin, N$^{\epsilon B29}$-decanoyl-N$^{\alpha B1}$-decanoyl-human insulin, N$^{\epsilon B29}$-decanoyl-N$^{\alpha A1}$-decanoyl-human insulin, N$^{\alpha A1}$-decanoyl-N$^{\alpha B1}$-decanoyl-human insulin, N$^{\epsilon B29}$-decanoyl-N$^{\alpha A1}$-decanoyl-N$^{\alpha B1}$-decanoyl-human insulin.

In certain embodiments, an insulin molecule of the present disclosure comprises the mutations and/or chemical modifications of one of the following insulin molecules: N$^{\epsilon B28}$- formyl-Lys$^{B28}$Pro$^{B29}$-human insulin, N$^{\alpha B1}$-formyl-Lys$^{B28}$Pro$^{B29}$-human insulin, N$^{\alpha A1}$-formyl-Lys$^{B28}$Pro$^{B29}$-human insulin, N$^{\epsilon B28}$-formyl-N$^{\alpha B1}$-formyl-Lys$^{B28}$Pro$^{B29}$-human insulin, N$^{\epsilon B28}$-formyl-N$^{\alpha A1}$-formyl-Lys$^{B28}$Pro$^{B29}$-human insulin, N$^{\alpha A1}$-formyl-N$^{\alpha B1}$-formyl-Lys$^{B28}$Pro$^{B29}$-human insulin, N$^{\epsilon B28}$-formyl-N$^{\alpha A1}$-formyl-N$^{\alpha B1}$-formyl-Lys$^{B28}$Pro$^{B29}$-human insulin, N$^{\epsilon B29}$-acetyl-Lys$^{B28}$Pro$^{B29}$-human insulin, N$^{\alpha B1}$-acetyl-Lys$^{B28}$Pro$^{B29}$-human insulin, N$^{\alpha A1}$-acetyl-Lys$^{B28}$Pro$^{B29}$-human insulin, N$^{\epsilon B28}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-acetyl-N$^{\alpha A1}$-acetyl-Lys$^{B28}$Pro$^{B29}$-human insulin, N$^{\alpha A1}$-acetyl-N$^{\alpha B1}$-acetyl-Lys$^{B28}$Pro$^{B29}$-human insulin, N$^{\epsilon B28}$-acetyl-N$^{\alpha A1}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-propionyl-Lys$^{B28}$Pro$^{B29}$-human insulin, N$^{\alpha B1}$-propionyl-Lys$^{B28}$Pro$^{B29}$-human insulin, N$^{\alpha A1}$-propionyl-Lys$^{B28}$Pro$^{B29}$-human insulin, N$^{\epsilon B28}$-propionyl-N$^{\alpha B1}$-propionyl-Lys$^{B28}$Pro$^{B29}$-human insulin, N$^{\epsilon B28}$-propionyl-N$^{\alpha A1}$-propionyl-Lys$^{B28}$Pro$^{B29}$-human insulin, N$^{\alpha A1}$-propionyl-N$^{\alpha B1}$-propionyl-Lys$^{B28}$Pro$^{B29}$-human insulin, N$^{\epsilon B28}$-propionyl-N$^{\alpha A1}$-propionyl-N$^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-butyryl-Lys$^{B28}$Pro$^{B29}$-human insulin, N$^{\alpha B1}$-butyryl-Lys$^{B28}$Pro$^{B29}$-human insulin, N$^{\alpha A1}$-butyryl-Lys$^{B28}$Pro$^{B29}$-human insulin, N$^{\epsilon B28}$-butyryl-N$^{\alpha B1}$-butyryl-Lys$^{B28}$Pro$^{B29}$-human insulin, N$^{\epsilon B28}$-butyryl-N$^{\alpha A1}$-butyryl-Lys$^{B28}$Pro$^{B29}$-human insulin, N$^{\alpha A1}$-butyryl-N$^{\alpha B1}$-butyryl-Lys$^{B28}$Pro$^{B29}$-human insulin, N$^{\epsilon B28}$-butyryl-N$^{\alpha A1}$-butyryl-N$^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-pentanoyl-Lys$^{B28}$Pro$^{B29}$-human insulin, N$^{\alpha B1}$-pentanoyl-Lys$^{B28}$Pro$^{B29}$-human insulin, N$^{\alpha A1}$-pentanoyl-Lys$^{B28}$Pro$^{B29}$-human insulin, N$^{\epsilon B28}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-Lys$^{B28}$Pro$^{B29}$-human insulin, N$^{\alpha A1}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-N$^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-hexanoyl-Lys$^{B28}$Pro$^{B29}$-human insulin, N$^{\alpha B1}$-hexanoyl-Lys$^{B28}$Pro$^{B29}$-human insulin, N$^{\alpha A1}$-hexanoyl-Lys$^{B28}$Pro$^{B29}$-human insulin, N$^{\epsilon B28}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-Lys$^{B28}$Pro$^{B29}$-human insulin, N$^{\alpha A1}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-N$^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-heptanoyl-Lys$^{B28}$Pro$^{B29}$-human insulin, N$^{\alpha B1}$-heptanoyl-Lys$^{B28}$Pro$^{B29}$-human insulin, N$^{\alpha A1}$-heptanoyl-Lys$^{B28}$Pro$^{B29}$-human insulin, N$^{\epsilon B28}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-Lys$^{B28}$Pro$^{B29}$-human insulin, N$^{\alpha A1}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-N$^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-octanoyl-Lys$^{B28}$Pro$^{B29}$-human insulin, N$^{\alpha B1}$-octanoyl-Lys$^{B28}$Pro$^{B29}$-human insulin, N$^{\alpha A1}$-octanoyl-Lys$^{B28}$Pro$^{B29}$-human insulin, N$^{\epsilon B28}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-Lys$^{B28}$Pro$^{B29}$-human insulin, N$^{\alpha A1}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-N$^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-nonanoyl-Lys$^{B28}$Pro$^{B29}$-human insulin, N$^{\alpha B1}$-nonanoyl-Lys$^{B28}$Pro$^{B29}$-human insulin, N$^{\alpha A1}$-nonanoyl-Lys$^{B28}$Pro$^{B29}$-human insulin, N$^{\epsilon B28}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-Lys$^{B28}$Pro$^{B29}$-human insulin, N$^{\alpha A1}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-N$^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-decanoyl-Lys$^{B28}$Pro$^{B29}$-human insulin, N$^{\alpha B1}$-decanoyl-Lys$^{B28}$Pro$^{B29}$-human insulin, N$^{\alpha A1}$-decanoyl-Lys$^{B28}$Pro$^{B29}$-human insulin, N$^{\epsilon B28}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\alpha A1}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-N$^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-pentanoyl-Gly$^{A21}$Arg$^{B31}$Arg$^{B32}$-human insulin, N$^{\alpha B1}$-hexanoyl-Gly$^{A21}$Arg$^{B31}$Arg$^{B32}$-human insulin, N$^{\alpha A1}$-heptanoyl-Gly$^{A21}$Arg$^{B31}$Arg$^{B32}$-human insulin, N$^{\epsilon B29}$-octanoyl-N$^{\alpha B1}$-octanoyl-Gly$^{A21}$Arg$^{B31}$Arg$^{B32}$-N$^{\alpha A1}$-human insulin, N$^{\epsilon B29}$-propionyl-N$^{\alpha A1}$-propionyl-Gly$^{A21}$Arg$^{B31}$Arg$^{B32}$-human insulin, N$^{\alpha A1}$-acetyl-N$^{\alpha B1}$-acetyl-Gly$^{A21}$Arg$^{B31}$Arg$^{B32}$-human insulin, N$^{\epsilon B29}$-formyl-N$^{\alpha A1}$-formyl-N$^{\alpha B1}$-formyl-Gly$^{A21}$Arg$^{B31}$Arg$^{B32}$-human insulin, N$^{\epsilon B29}$-formyl-des (B26)-human insulin, N$^{\alpha B1}$-acetyl-Asp$^{B28}$-human insulin, N$^{\epsilon B29}$-propionyl-N$^{\alpha A1}$-propionyl-N$^{\alpha B1}$-propionyl-Asp$^{B1}$Asp$^{B3}$AspB$^{21}$-human insulin, N$^{\epsilon B29}$-pentanoyl-Gly$^{A21}$-human insulin, N$^{\alpha B1}$-hexanoyl-Gly$^{A21}$-human insulin, N$^{\alpha A1}$-heptanoyl-Gly$^{A21}$-human insulin, N$^{\epsilon B29}$-octanoyl-N$^{\alpha B1}$-octanoyl-Gly$^{A21}$-human insulin, N$^{\epsilon B29}$-propionyl-N$^{\alpha A1}$-propionyl-Gly$^{A21}$-human insulin, N$^{\alpha A1}$-acetyl-N$^{\alpha B1}$-acetyl-Gly$^{A21}$-human insulin, N$^{\epsilon B29}$-formyl-N$^{\alpha A1}$-formyl-N$^{\alpha B1}$-formyl-Gly$^{A21}$-human insulin, N$^{\epsilon B29}$-butyryl-des(B30)-human insulin, N$^{\alpha B1}$-butyryl-des(B30)-human insulin, N$^{\alpha A1}$-butyryl-des(B30)-human insulin, N$^{\epsilon B29}$-butyryl-N$^{\alpha B1}$-butyryl-des(B30)-human insulin, N$^{\epsilon B29}$-butyryl-N$^{\alpha A1}$-butyryl-des(B30)-human insulin, N$^{\alpha A1}$-butyryl-N$^{\alpha B1}$-butyryl-des(B30)-human insulin, N$^{\epsilon B29}$-butyryl-N$^{\alpha A1}$-butyryl-N$^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

Methods for conjugating drugs including insulin molecules are described below. In certain embodiments, an insulin molecule is conjugated to the conjugate framework via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated to the conjugate framework via the B1 amino acid residue. In certain embodiments the B1 amino acid residue is phenylalanine. It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. It will be appreciated that different conjugation positions on the B-chain may lead to different reductions in insulin activity.

In certain embodiments, the ligands are conjugated to more than one conjugation point on a drug such as an insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{43}$.

In various embodiments, a conjugate may include an insulin sensitizer (i.e., a drug which potentiates the action of insulin). Drugs which potentiate the effects of insulin include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

In various embodiments, a conjugate may include an insulin secretagogue (i.e., a drug which stimulates insulin secretion by beta cells of the pancreas). For example, in various embodiments, a conjugate may include a sulfonylurea. Sulfonylureas stimulate insulin secretion by beta cells of the pancreas by sensitizing them to the action of glucose. Sulfonylureas can, moreover, inhibit glucagon secretion and sensitize target tissues to the action of insulin. First generation sulfonylureas include tolbutamide, chlorpropamide and carbutamide. Second generation sulfonylureas which are active at lower doses include glipizide, glibenclamide, gliclazide, glibornuride and glimepiride. In various embodiments, a conjugate may include a meglitinide. Suitable meglitinides include nateglinide, mitiglinide and repaglinide. Their hypoglycemic action is faster and shorter than that of sulfonylureas. Other insulin secretagogues include glucagon-like peptide 1 (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, a conjugate may include amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

In various embodiments, a pre-conjugated drug may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic drugs bearing alpha-terminal amine and/or epsilon-amine lysine groups. It will be appreciated that any of these reactive moieties may be artificially added to a known drug if not already present. For example, in the case of peptidic drugs a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

As discussed above, the present disclosure is not limited to any particular combination of drug and target molecule.

In various embodiments, a material of the present disclosure may be exploited to manipulate a natural feedback mechanism. For example, there are many natural feedback mechanisms (including most hormonal control mechanisms) in which the level of two endogenous substances are interrelated (e.g., glucose and insulin where the level of insulin increases as the level of glucose increases and the level of glucose decreases as the level of insulin increases). In such embodiments one of the endogenous substances can become the target molecule (e.g., glucose) while the other becomes the drug (e.g., insulin). Alternatively, in various embodiments, the drug can be a molecule that (a) has the same function as the other endogenous substance (e.g., reduces glucose levels), (b) stimulates the production of the other endogenous substance and/or (c) potentiates the effect(s) of the other endogenous substance. For example, when glucose is the target molecule one could use an insulin secretagogue or an insulin sensitizer instead of insulin as the drug.

Other non-limiting examples of artificial feedback systems, include, a material which releases glucagon conjugates in response to high levels of insulin, a material which releases anticoagulant conjugates (e.g., coumarines such as warfarin, acenocoumarol, phenprocoumon and phenindione, heparin, direct thrombin inhibitors such as argatroban, lepirudin, bivalirudin, and dabigatran, etc.) in response to thrombosis indicators; a material which releases lactate-lowering drug conjugates (e.g., dichloroacetate) in response to increased lactate levels; etc.

In various embodiments, a material can be designed to release conjugates which include a drug with a function that is not directly related to the target molecule. Without limitation, a material which responds to a target molecule which increases in concentration after a meal (e.g., glucose) may be used to provide long-term, mealtime dosing of a drug. Any drug which needs to be dosed periodically and/or with food would benefit from such a delivery system. As is well known in the art, many traditional drugs need to be administered with food or at mealtimes. For example, drugs which inhibit the absorption of fats (e.g., orlistat) are advantageously present during mealtime. Similarly, drugs which lower lipid levels, e.g., lovastatin, atorvastatin, or simvastatin, or triglyceride levels, e.g., gemfibrozil, may also be advantageously released at mealtimes.

D (Detectable Label)

As noted above, in various embodiments, the W in D is a detectable label. For example, a detectable label may be included in order to detect the location of conjugates within an organism, tissue or cell; when the conjugates are used in a sensor; etc. It is to be understood that a conjugate can comprise any detectable label known in the art. A conjugate can comprise more than one copy of the same label and/or can comprise more than one type of label. In general, the label(s) used will depend on the end application and the method used for detection.

The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Fluorescein isothiocyanate, rhodamine, phycoerythrin phycocyanin, allophycocyanin, γ-phthalaldehyde, fluorescamine, etc. are all exemplary fluorescent labels. Chemiluminescent labels, i.e., labels that are capable of converting a secondary substrate to a chromogenic product are examples of indirectly detectable labels. For example, horseradish peroxidase, alkaline phosphatase, glucose-6-phosphate dehydrogenase, malate dehydrogenase, staphylococcal nuclease, delta-V-steroid isomerase, yeast alcohol dehydrogenate, α-glycerophosphate dehydrogenase, triose phosphate isomerase, asparaginase, glucose oxidase, β-galactosidase, ribonuclease, urease, catalase, glucoamylase, acetylcholinesterase, luciferin, luciferase, aequorin and the like are all exemplary protein based chemiluminescent labels. Luminol, isoluminol, theromatic acridinium ester, imidazole, acridinium salt, oxalate ester, etc. are exemplary non-protein based chemiluminescent labels. Another non-limiting and commonly used example of an indirectly detectable label is an affinity ligand, i.e., a label with strong affinity for a secondary binding partner (e.g., an antibody or aptamer) which may itself be directly or indirectly detectable.

In general, a detectable label may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In various embodiments, a pre-conjugated label may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic labels bearing alpha-terminal amine and/or epsilon-amine lysine groups. It will be appreciated that any of these reactive moieties may be artificially added to a known label if not already present. For example, in the case of peptidic labels a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

$L^B$ and $L^D$ (Covalent Conjugation)

One of ordinary skill will appreciate that a variety of conjugation chemistries may be used to covalently conjugate an X with a T and/or a W with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the conjugate framework). It is to be understood that components may be covalently bound to a conjugate framework through any number of chemical bonds, including but not limited to amide, amine, ester, ether, thioether, isourea, imine, etc. bonds. In certain embodiments, $L^B$ and/or $L^D$ (generally "L" for the purposes of this section) is a covalent bond. In some embodiments, L is an optionally substituted moiety derived from conjugating an optionally substituted carbonyl-reactive, thiol-reactive, amine-reactive, or hydroxyl-reactive moiety of T with a carboxyl, thiol, amine, or hydroxyl group of X or W. In some embodiments, L is an optionally substituted moiety derived from conjugating an optionally substituted carboxyl-reactive, thiol-reactive, amine-reactive, or hydroxyl-reactive moiety of X or W with a carboxyl, thiol, amine, or hydroxyl group of T. In some embodiments, L is

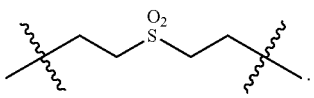 [SMILES: *CCS(=O)(=O)CC*]

In some embodiments, L is a succinimide moiety.

In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to a conjugate framework via natural or chemically added pendant groups. In general, it will be appreciated that the first and second members of a pair of reactive groups (e.g., a carboxyl group and an amine group which react to produce an amide bond) can be present on either one of the component and framework (i.e., the relative location of the two members is irrelevant as long as they react to produce a conjugate). Exemplary linkages are discussed in more detail below.

In various embodiments, carboxyl (or reactive ester) bearing components can be conjugated to —OH bearing frameworks (OBFs) using the procedure outlined by Kim et al., *Biomaterials* 24:4843-4851 (2003). Briefly, the OBF is dissolved in DMSO along with the carboxyl bearing component and reacted by means of N',N'-dicyclohexylcarbodiimide (DCC) and 4-dimethylaminopyridine (DMAP) as catalysts under a dry atmosphere. Carboxyl bearing components can be conjugated to —NH$_2$ bearing frameworks (NBFs) using a carbodiimide (EDAC) coupling procedure. Using this procedure, the carboxyl bearing component is functionalized by reaction with EDAC in a pH 5 buffer followed by the addition of the NBF. In either of these cases (and in any of the following cases), the resulting products may be purified by any number of means available to those skilled in the art including, but not limited to, size exclusion chromatography, reversed phase chromatography, silica gel chromatography, ion exchange chromatography, ultrafiltration, and selective precipitation.

In various embodiments, amine bearing components can be coupled to —COOH bearing frameworks (CBFs). CBFs using activated ester moieties (e.g., see Hermanson in *Bioconjugate Techniques*, 2$^{nd}$ edition, Academic Press, 2008 and references cited therein). Briefly, a CBF with terminal activated carboxylic acid esters such as —NHS, —SSC, —NPC, etc. is dissolved in an anhydrous organic solvent such as DMSO or DMF. The desired number of equivalents of amine bearing component are then added and mixed for several hours at room temperature. Amine bearing components can also be conjugated to CBFs to produce a stable amide bond as described by Baudys et al., *Bioconj. Chem.* 9:176-183, 1998. This reaction can be achieved by adding tributylamine (TBA) and isobutylchloroformate to a solution of the CBF and an amine bearing component in dimethylsulfoxide (DMSO) under anhydrous conditions. Amine bearing components can alternatively be coupled to OBFs through cyanalation using reagents including, but not limited to, cyanogen bromide (CNBr), N-cyanotriethylammonium tetrafluoroborate (CTEA), 1-Cyano-4-(Dimethylamino)-pyridinium tetrafluoroborate (CDAP), and p-nitrophenylcyanate (pNPC). CNBr reactions can be carried out at mildly basic pH in aqueous solution. CDAP reactions are carried out in a mixture of DMSO and water at mildly basic pH using triethylamine (TEA) as a catalyst. In certain embodiments, amine bearing components can be conjugated to NBFs, e.g., through glutaraldehyde coupling in aqueous buffered solutions containing pyridine followed by quenching with glycine. In certain embodiments, amine bearing components can be conjugated to aldehyde bearing frameworks using a Schiff Base coupling procedure followed by reduction (e.g., see Hermanson in *Bioconjugate Techniques*, 2$^{nd}$ edition, Academic Press, 2008 and references cited therein as well as Mei et al. in *Pharm. Res.* 16: 1680-1686, 1999 and references cited therein). Briefly, a framework with terminal activated aldehydes (e.g., acetaldehyde, propionaldehyde, butyraldehyde, etc.) is dissolved in an aqueous buffer with the pH at or below neutral to prevent unwanted aldehyde hydrolysis. The desired number of equivalents of an amine bearing component are then added and mixed at room temperature followed by addition of an excess of suitable reducing agent (e.g., sodium borohydride, sodium cyanobrohydride, sodium triacetoxyborohydride pyridine borane, triethylamine borane, etc.).

In various embodiments, hydroxyl bearing components can be conjugated to OBFs according to the divinylsulfone (DVS) procedure. Using this procedure, the OBF is added to a pH 11.4 bicarbonate buffer and activated with DVS followed by addition of a hydroxyl bearing component after which glycine is added to neutralize and quench the reaction. Hydroxyl bearing components may also be coupled to OBFs using activated ester moieties as described above to produce ester bonds.

In various embodiments, sulfhydryl bearing components can be coupled to maleimide bearing frameworks (MBFs) using a relatively mild procedure to produce thioether bonds (e.g., see Hermanson in *Bioconjugate Techniques*, 2$^{nd}$ edition, Academic Press, 2008 and references cited therein). Because the maleimide group is much less susceptible to hydrolysis than activated esters, the reaction can be carried out under aqueous conditions. Briefly, an MBF is dissolved in a buffered aqueous solution at pH 6.5-7.5 followed by the desired number of equivalents of sulfhydryl bearing component. After mixing at room temperature for several hours, the thioether coupled conjugate may be purified. Sulfhydryl bearing components can also be conjugated to NBFs according to a method described by Thoma et al., *J. Am. Chem. Soc.* 121:5919-5929, 1999. This reaction involves suspending the NBF in anhydrous dimethylformamide (DMF) followed by the addition of 2,6-lutidine and acid anhydride and subsequent purification of the reactive intermediate. A sulfhydryl bearing component is then added to a solution of the intermediate in DMF with triethylamine.

In various embodiments, azide bearing components can be coupled to an alkyne bearing framework (ABF) using the copper(I)-catalyzed modern version of the Huisgen-type azide-alkyne cycloaddition to give a 1,4-di-substituted 1,2,3-triazole (e.g., see Dondoni, *Chem. Asian J.* 2:700-708, 2007 and references cited therein as well as Dedola et al., *Org. Biomol. Chem.* 5: 1006-1017, 2007). This reaction, commonly referred to as a "click" reaction, may be carried out for example in neat THF using N,N-diisopropylethylamine and Cu(PPh$_3$)$_3$Br as the catalyst system (e.g., see Wu et al., *Chem. Commun.* 5775-5777, 2005). The reaction may also be carried out in a 3:1 (THF:water) mixture using sodium ascorbate and CuSO$_4$.5H$_2$O as the catalyst system (e.g., see Wu et al., supra). In either case, the azide bearing component is added to the ABF at the desired number of equivalents followed by mixing for 12-48 hours at room temperature. Alternatively, alkyne bearing components may be conjugated to an azide bearing framework using exactly the same conditions described above.

Certain components may naturally possess more than one of the same chemically reactive moiety. In some examples, it is possible to choose the chemical reaction type and conditions to selectively react the component at only one of those sites. For example, in the case where insulin is conjugated through reactive amines, in certain embodiments, the N-terminal α-Phe-B1 is a preferred site of attachment over the N-terminal α-Gly-A1 and ε-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in certain embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J.* 109: 312-314, 1968; and Schuettler et al., *D. Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF is added slowly and the solution allowed to mix for 30-60 minutes. After reaction, the crude solution is poured in an excess of acetone followed by dropwise addition of dilute HCl to precipitate the reacted insulin. The precipitated material is centrifuged, washed with acetone and dried completely under vacuum. The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, rotovapped to remove acetonitrile, and lyophilized to obtain the pure product.

LRP$^B$ and LRP$^D$ (Non-Covalent Conjugation)

One of ordinary skill will appreciate that a variety of conjugation chemistries may be used to non-covalently conjugate an X with a T and/or W with a T (generally "components"). Such techniques are widely known in the art, and exemplary techniques are discussed below. In certain embodiments, the dissociation constant (K$_d$) of the non-covalent linkage in human serum is less than 1 pmol/L. For example, a component may be non-covalently bound to a conjugate framework via a non-covalent ligand-receptor pair as is well known in the art (e.g., without limitation a biotin-avidin based pair). In such an embodiment, one member of the ligand receptor-pair is covalently bound to the component while the other member of the pair is covalently bound to the conjugate framework. When the component and conjugate framework are combined, the strong non-covalent interaction between the ligand and its receptor causes the component to become non-covalently bound to the conjugate framework. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., Academic Press, 1992.

k and q

For conjugates of general formula (I), k is an integer from 2 to 11, inclusive, defining at least two k-branches within the conjugate. In certain embodiments, k=2 or 3. q is an integer from 1 to 4, inclusive, and defines the number of D groups which are bound to the central $$\boxed{A}$$

group. In certain embodiments, q=1. In some embodiments, q=2. k+q is an integer from 3 to 6, inclusive. In certain embodiments, k+q=3 or 4.

For conjugates of general formula (II), when j is 2, 3, or 4, k is an integer from 1 to 11, inclusive. In certain embodiments, k is 1, 2, or 3. q is an integer from 1 to 4, inclusive, and defines the number of D groups which are bound to the central $$\boxed{A}$$

group. In certain embodiments, q=1. In some embodiments, q=2. k+q is an integer from 3 to 6, inclusive. In certain embodiments, k+q=3 or 4.

p and m

Each occurrence of p is independently an integer from 1 to 5, inclusive. In certain embodiments, each occurrence of p is the same. In certain embodiments, p=1, 2 or 3. In certain embodiments, p=1.

Each occurrence of m is independently an integer from 1 to 5, inclusive. In certain embodiments, each occurrence of m is the same. In certain embodiments, m=1, 2 or 3. In certain embodiments, m=1.

n and v

Each occurrence of n is independently an integer from 0 to 5, inclusive, with the proviso that within each k-branch at least one occurrence of n is ≥1. Branches within a given k-branch are referred to herein as n-branches.

In certain embodiments, each occurrence of $$\boxed{A}$$

in a p-bracketed moiety is substituted by a number of n-bracketed moieties corresponding to a value of n≥1, e.g., see formula (Ia) above. In some such embodiments, each occurrence of n in the conjugate is the same. In some of these embodiments, n=1 or 2.

In other embodiments, only terminal occurrences of $$\boxed{A}$$

in a p-bracketed moiety are substituted by a number of n-bracketed moieties corresponding to a value of n≥1, e.g., see formula (Ib) above. In certain embodiments, each k-branch includes just one occurrence of n≥1 (i.e., all other occurrences of n=0). In some such embodiments, each occurrence of n in the conjugate is the same. In some of these embodiments, n=1 or 2.

Each occurrence of v is independently an integer from 0 to 5, inclusive, with the proviso that within each k-branch at least one occurrence of v is ≥1.

In certain embodiments, each occurrence of $$\boxed{A}$$

in an m-bracketed moiety is substituted by a number of B moieties corresponding to the value of v≥1, e.g., see formula (Ic) above. In some such embodiments, each occurrence of v in the conjugate is the same. In some of these embodiments, v=1 or 2.

In other embodiments, only terminal occurrences of $$\boxed{A}$$

in an m-bracketed moiety are substituted by a number of B moieties corresponding to a value of v≥1, e.g., see formula (Id) above. In certain embodiments, each k-branch includes just one occurrence of v≥1 (i.e., all other occurrences of v=0). In some such embodiments, each occurrence of v in the conjugate is the same. In some of these embodiments, v=1 or 2. In certain embodiments, each n-branch includes at least one occurrence of v≥1. In certain embodiment, each n-branch includes just one occurrence of v≥1 (i.e., all other occurrences of v=0). In some such embodiments, each occurrence of v in the conjugate is the same. In some of these embodiments, v=1 or 2.

j j of formula (II) is an integer from 2 to 4, inclusive, and defines the number of conjugations to the D group. In certain embodiments, j=2. In some embodiments, j=3. In other embodiments, j=4.

Loading Levels

In general, the amount of drug (or detectable label) that is loaded onto a conjugate will depend on the molecular weight of the drug and can be controlled by adjusting the molecular weight of the conjugate framework and/or the level of chemical activation (i.e., when pendant groups are added to the framework). In various embodiments, the drug loading level may be in the range of 5 to 99% w/w of drug to conjugate (i.e., including drug). In various embodiments, loading levels within the narrower range of 50 to 99% may be used, e.g., in the range of 80 to 99%.

Intermediates for Preparing Conjugates

In one aspect, the invention provides reagents for preparing conjugates of the present disclosure. Thus, in various embodiments, a compound of general formula (I) is provided wherein:

each of $$\boxed{A},$$

T, D, k, q, k+q, p, n, m and v is defined as described above and herein;

B is -T-$L^{B'}$; and each occurrence of $L^{B'}$ is independently hydrogen, an alkyne-containing moiety, an azide-containing moiety, or an optionally substituted carbonyl-reactive, thiol-reactive, amine-reactive, or hydroxyl-reactive moiety.

In other embodiments, a compound of general formula (I) is provided wherein:

each of $$\boxed{A},$$

T, B, k, q, k+q, p, n, m and v is defined as described above and herein;

D is -T-$L^{D'}$; and each occurrence of $L^{D'}$ is independently hydrogen, an alkyne-containing moiety, an azide-containing moiety, or an optionally substituted carbonyl-reactive, thiol-reactive, amine-reactive, or hydroxyl-reactive moiety.

Methods for Preparing Conjugates

As described in the Examples, we have exemplified methods for preparing the aforementioned conjugates using insulin as an exemplary drug and aminoethylglucose (AEG), aminoethylmannose (AEM), aminoethylbimannose (AEBM), and/or aminoethyltrimannose (AETM) as exemplary affinity ligands. Without limitation, conjugates with two affinity ligands and one drug molecule and with short distances between all framework components may be prepared using tris(hydroxymethyl)aminomethane (Tris), Tris-succinimidyl aminotriacetate (TSAT), tris-Succinimidyl-1,3,5-benzenetricarboxylate (TSB), and Benzene-1,3,5-tricarboxy-(N-4-butyric-NHS-ester)amide (TSB-C4) as conjugate frameworks. If more space between framework components is desired then Succinimidyl (6-aminocaproyl)aminotriacetate (TSAT-C6), Succinimidyl (6-amino(PEO-6))aminotriacetate (TSAT-PEO-6), Benzene-1,3,5-tricarboxy-(N-6-aminocaproic-NHS ester)amide (TSB-C6), and Benzene-1,3,5-tricarboxy-(N-10-aminodecanoic-NHS ester)amide (TSB-C10) may be used. The TSAT-C6 spacer arm chemistry imparts more hydrophobic character to the conjugate as compared to TSAT-PEO-6.

For example, for purposes of illustration, in one embodiment, both the affinity ligand (e.g., AEG, AEM, AEMB and AETM) and insulin may be reacted to a TSAT-C6 framework through the terminal activated esters to produce insulin-TSAT-C6-AEG-2, insulin-TSAT-C6-AEM-2, insulin-TSAT-C6-AEMB-2, and insulin-TSAT-C6-AETM-2 conjugates. The various affinity ligands are synthesized ahead of time as discussed in the Examples. In addition, the A1 and B29 amino groups of insulin are BOC-protected as described in the Examples so that each insulin can only react at the Phe-B1 α-amino group. Approximately one equivalent of BOC-insulin as a 40-50 mg/ml solution in DMSO is added at room temperature to a 50 mg/ml solution of TSAT-C6 in DMSO containing excess triethylamine and allowed to react for approximately one hour. Next, an excess of AEG, AEM, AEBM, and/or AETM (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted BOC2-insulin. The desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 10× superdilution in HEPES pH 8.2 buffer containing 0.150M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

It will be appreciated that this exemplary procedure may be used to produce other conjugates with different affinity ligands and drugs, different conjugation chemistries, different separations between framework components, and/or different valencies by substituting the TSAT-C6 framework with a different framework as described below.

For example, if yet more distance is required between framework components and/or a preserved charge is required at the site of conjugation, then an appropriately-sized amine-bearing diethyl acetal (e.g., aminopropionaldehyde diethyl acetal (APDA) or aminobutyraldehyde diethyl acetal (ABDA)) may be conjugated to one of the reactive groups on the frameworks listed here followed by complete reaction of the remaining reactive groups with the affinity ligand of interest (e.g. AEM, AEBM, or AETM). A reactive aldehyde group can then be revealed from the diethyl acetal under acidic conditions followed by a reductive amination with insulin to complete the drug conjugation step then ABDA-TSAT, ABDA-LCTSAT, etc. may be employed.

In yet another example, tetrakis-(N-succinimidyl carboxypropyl)pentaerythritol (TSPE), may be used to attach three affinity ligands and one drug molecule for increased multivalency. It will also be appreciated by those skilled in the art that any of the above teachings may be used to produce hyperbranched (e.g., dendrimer-like) conjugates with even higher order valencies. For example, Röckendorf and Lindhorst provide a comprehensive review of current approaches for producing hyperbranched structures in *Topics in Current Chemistry.* 217: 202-238, 2001.

Furthermore, ligands already containing a predetermined degree of multivalency may again be reacted according to the procedures described above to produce even higher orders of ligand multiplicity. For example, a divalent AEM-2, AEBM-2, or AETM-2 molecule containing a terminal reactive amine may be prepared by conjugating two of each affinity ligand to a suitable framework to which a reactive amine is also conjugated. A trivalent AEM-3, AEBM-3, or AETM-3 molecule containing a terminal reactive amine may be prepared by conjugating three of each affinity ligand to a suitable framework to which a reactive amine is also conjugated. The $NH_2$-divalent sugars may be reacted with the same frameworks described above to produce drug conjugates with 4 and 6 ligands per drug molecule. The $NH_2$-trivalent sugars may be reacted with the same frameworks described above to produce drug conjugates with 6 and 9 ligands per drug molecule.

In all cases, it should be recognized that a mixture of different ligands may be conjugated to the same drug via a multivalent framework by adjusting the framework chemistry, valency, and the ligand:framework stoichiometry. For example, Insulin-AEM-1-AEBM-1, Insulin-AEBM-1-AETM-1, Insulin AEM-2-AETM-2, and Insulin AEM-1-AETM-2 may all be synthesized according to this mixed ligand method.

Finally, in some cases, it may be desirable to conjugate the affinity ligand to the framework through a different means than the drug. For example, a divalent maleimide/monovalent activate ester functionalized framework (e.g., succinimidyl-3,5-dimaleimidophenyl benzoate (SDMB)) may be used to conjugate two sulfhydryl functionalized affinity ligands and one amine-functionalized drug in separate steps. For example, insulin or another amine-containing drug may be conjugated to the activated ester portion of the framework using methods described herein. In a separate step, the aminoethylsugar (AEM, AEBM, AETM) may be converted to a terminal sulfhydryl-bearing ligand by reaction with 4-iminothiolane. Finally, the framework-di-maleimide-insulin conjugate may be mixed with an excess of sulfhydryl-functionalized sugar to produce the resulting divalent-sugar-insulin conjugate.

Multivalent Cross-Linking Agents

In certain embodiments, the conjugates of the present disclosure may be combined with multivalent cross-linking agents to form cross-linked materials. The following sections describe exemplary cross-linking agents that can be used.

As discussed in more detail below and as illustrated in FIG. 28, the cross-linked material 10 is capable of controllably releasing the conjugates 20 in response to a target molecule (e.g., glucose). The materials are prepared by combining the conjugates 20 with multivalent cross-linking agents 30 that non-covalently bind the affinity ligands 40 of the conjugates 20 and thereby cross-link the conjugates 20 to form the cross-linked material 10. The non-covalent bonds between the multivalent cross-linking agents 30 and the affinity ligands 40 are competitively dissociated in the presence of excess amounts of the target molecule (e.g., glucose).

1. Polypeptide Cross-Linking Agents

In various embodiments, the multivalent cross-linking agents may include a polypeptide. As discussed in more detail below, suitable multivalent polypeptides exist in nature (e.g., various lectins) but can also be constructed by linking multiple monovalent binding proteins, e.g., monovalent lectins, peptide aptamers, antibodies, cell membrane receptors, etc. Still other multivalent polypeptides may be constructed by chemically linking binding fragments of these proteins.

A variety of mono- and multivalent ligand-binding proteins are available commercially (e.g., from Sigma-Aldrich), including a number of lectins, folate-binding protein, thyroxine-binding globulin, lactoferrin, etc. DeWolf and Best provide a review of ligand-binding proteins including biotin-binding proteins, lipid-binding proteins/transporters of hydrophobic molecules, bacterial periplasmic binding proteins, lectins, serum albumins, immunoglobulins, inactivated enzymes, odorant-binding proteins, immunosuppressant-binding proteins, and phosphate- and sulfate-binding proteins (see De Wolfe and Best, *Pharm. Rev.* 52: 207-236, 2000 and references cited therein). The cell membrane receptors for a variety of hormones have also been described in the art. In certain embodiments, mono- or multivalent binding proteins can be synthesized by rational computational design followed by site directed mutagenesis of existing ligand-binding proteins as described in Looger et al., *Nature* 423:185-190, 2003. Exemplary protein fragments include truncated MBP (Eda et al., *Biosci. Biotechnol. Biochem.*, 62:1326-1331, 1998), truncated conglutinin (Eda et al., *Biochem. J.* 316:43, 1996), truncated SP-D (Eda et al., *Biochem. J.* 323:393, 1997), and the glucose/galactose binding protein of *E. Coli* (Salins et al., *Analytical Biochemistry* 294:19-26, 2001).

a. Lectins

In certain embodiments, mono- or multivalent lectins may be included in a multivalent cross-linking agent. As discussed in more detail below, in certain embodiments, it may be advantageous to chemically modify the lectins. Lectins are particularly suitable for use in materials which are designed to respond to a saccharide (e.g., glucose). Lectins have been isolated from a variety of natural sources including seeds, roots, bark, fungi, bacteria, seaweed, sponges, mollusks, fish eggs, body fluids of invertebrates and lower vertebrates, and mammalian cell membranes (e.g., see *The Lectins: Properties, Functions, and Applications in Biology and Medicine*, Edited by Liener et al., Academic Press, 1986). A number of lectins have also been produced recombinantly (e.g., see Streicher and Sharon, *Methods Enzymol.* 363:47-77, 2003 and U.S. Patent Publication No. 20060247154). As noted above, lectins bind saccharides and polysaccharides with a high degree of specificity. For example, some lectins will bind only to mannose or glucose residues, while others only recognize galactose residues. Some lectins require that the particular residue be in a terminal position, while others bind to residues within a polysaccharide chain. Some lectins require specific anomeric structures and yet others recognize specific sugar sequences. The structures and properties of lectins have been extensively described in the literature. For recent reviews see Lectins, Edited by Sharon and L is, Kluwer Academic Publishers, 2003; *Handbook of Animal Lectins: Properties and Biomedical Applications*, Edited by Kilpatrick, Wiley, 2000; and *Handbook of Plant Lectins: Properties and Biomedical Applications*, Edited by Van Damme et al., Wiley, 1998. Exemplary lectins include calnexin, calreticulin, CD22, CD33, galectin (galactose-binding lectin), myelin-associated glycoprotein, N-acetylglucosamine receptor, selectin, sialoadhesin, aggrecan, asialoglycoprotein receptor, CD94, collectin (mannose-binding lectin), mannose receptor, versican, abrin, ricin, concanavalin A, phytohaemagglutinin, and pokeweed mitogen. In various embodiments, human analogs of plant lectins may be used. These include, without limitation, human mannan binding protein (MBP, also called mannan binding lectin, Sheriff et al., *Structural Biology*, 1:789-794 (1994); Dumestre-Perard et al., *Molecular Immunology*, 39:465-473 (2002)), human pulmonary surfactant protein A (SP-A, Allen, et al., *Infection and Immunity*, 67:4563-4569 (1999)), human pulmonary surfactant protein D (SP-D, Persson et al., *The Journal of Biological Chemistry*, 265:5755-5760 (1990)), CL-43 (a human serum protein), and conglutinin.

b. Peptide Aptamers

In certain embodiments monovalent peptide aptamers may be included in a multivalent cross-linking agent. As is well known in the art, peptide aptamers consist of a variable ligand-binding peptide loop fused within a protein scaffold (e.g., see Hoppe-Seyler and Butz, *J. Mol. Med.* 78:426-430, 2000 and Crawford et al., *Briefings in Functional Genomics and Proteomics* 2:72-79, 2003). The variable loop typically includes between about 10 and 20 amino acids. A variety of scaffold proteins may be used. In general, the site of insertion is chosen such that the peptide loop disrupts a region of the scaffold that would otherwise mediate some wild-type function, e.g., the bacterial protein thioredoxin-A in which the variable loop is inserted within the reducing active site (a -Cys-Gly-Pro-Cys-loop in the wild-type protein). Peptide aptamers with suitable affinity for the target molecule can be prepared and selected using any known method. For example, yeast two-hybrid libraries, yeast expression libraries, bacterial expression libraries and/or retroviral libraries for expression in mammalian cells may be used.

In various embodiments, peptide aptamers may be selected by affinity chromatography. According to such embodiments, peptide aptamers in a library are exposed to the target molecule and those that do not bind the target are removed. The bound peptide aptamers are then eluted and cloned for subsequent rounds of selection. A new library is then generated from one or more of these peptide aptamers (e.g., the peptide aptamer with the highest affinity for the target molecule in the first round of selection) and the stringency of the elution conditions is increased or modified to identify peptide aptamers with the desired binding affinity and/or specificity. In various embodiments, the selection process may involve steps in which the stringency of the elution conditions are gradually increased in order to select peptide aptamers with high affinity for the target molecule. In various embodiments, the selection process may involve steps in which the elution conditions are modified (e.g., by using a different affinity column) in order to select peptide aptamers with desired specificity for the target molecule. In various embodiments the selection process may generate a collection of sublibraries (or "pools") each of which comprises peptide aptamers with similar affinities and/or specificities for the target molecule. In various embodiments the selection process may generate a single peptide aptamer sequence (or "monoclonal"). It will be appreciated that any of these peptide aptamer sequences may be cloned for future recombinant expression.

c. Generating Multivalent Cross-Linking Agents

Multivalent cross-linking agents can be generated by covalently or non-covalently linking two or more monovalent binding proteins into a single construct. Typically, two or more proteins (which may have the same or different sequences) may be linked directly to one another (e.g., via a coupling agent) or indirectly through a framework. In various embodiments 2, 3, 4, 5, 6, 7 or 8 or more proteins may be combined into a single construct. In various embodiments the 2, 3, 4, 5, 6, 7 or 8 or more proteins may have the same sequence. It will be appreciated that either one of these approaches may require the proteins to be chemically modified (e.g., to include pendant reactive groups) prior to coupling. It will also be appreciated that the multivalent cross-linking agents of the present disclosure are not limited to a particular coupling reaction or framework (e.g., they can be prepared using frameworks that include polymeric and/or non-polymeric structures). It will further be appreciated that the frameworks may be linear, branched, dendrimeric and/or a combination of these. Exemplary frameworks and coupling chemistries are described below in the context of the conjugates.

In various embodiments the monovalent binding proteins are covalently linked to each other or a framework. In such embodiments, the proteins can be directly linked (i.e., with no intervening chemical groups) or indirectly linked through a spacer (e.g., a coupling agent or covalent chain that provides some physical separation between the protein or between the proteins and framework). As discussed below in the context of the conjugates it is to be understood that proteins may be covalently linked to each other or a framework through any number of chemical linkages, including but not limited to amide, ester, ether, isourea, and imine bonds.

In various embodiments, two or more monovalent binding proteins can be non-covalently linked to each other or to a framework. In certain embodiments, the dissociation constant ($K_d$) of the non-covalent linkage in human serum is less than 1 pmol/L. For example, proteins may be non-covalently linked to each other or a framework via a non-covalent ligand-receptor pair as is well known in the art (e.g., without limitation a biotin-avidin based pair). In such an embodiment, one member of the ligand receptor-pair is covalently linked to one protein while the other member of the pair is covalently linked to the other protein or framework. When the proteins (or proteins and framework) are combined, the strong non-covalent interaction between the ligand and its receptor causes the proteins to become non-covalently linked to each other (or the framework). Typical ligand/receptor pairs include protein/cofactor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; *"Affinity Chromatography: Methods and Protocols (Methods in Molecular Biology)*" Ed. by Pascal Baillon, Humana Press, 2000; and *"Immobilized Affinity Ligand Techniques*" by Hermanson et al., Academic Press, 1992.

2. Polynucleotide Cross-Linking Agents

In various embodiments, the multivalent cross-linking agents may include a polynucleotide aptamer. The polynucleotide aptamers bind the target molecule and are multivalent (i.e., capable of binding more than one target molecule). In general, monovalent aptamers will first be generated based on their binding properties for the target molecule. As is well known in the art, aptamers to a variety of target molecules can be generated through a process of in vitro selection. See Ellington and Szostak (1990) *Nature* 346:818; Tuerk and Gold (1990) *Science* 249:505; and U.S. Pat. No. 5,582,981. See also the glucose binding polynucleotide aptamers that are described in U.S. Provisional Application No. 61/162,092 filed Mar. 20, 2009, and corresponding PCT application filed Jan. 27, 2010, each of which is incorporated herein by reference.

Typically, the process begins with the synthesis of a library consisting of randomly generated polynucleotide sequences of fixed length flanked by constant 5' and 3' ends that serve as primers. In certain embodiments (e.g., when optimizing an aptamer) one might start with a sequence which is known to bind the target molecule and generate a library which includes a collection of polynucleotides which exhibit a limited range of changes from the starting sequence (e.g., a random set of single mutations). The sequences in the library are then exposed to the target molecule and those that do not bind the target are removed (e.g., by affinity chromatography). The bound sequences are then eluted and amplified (e.g., by cloning and subsequent transcription or by PCR) to prepare for subsequent rounds of selection in which the stringency of the elution conditions is increased or modified to identify sequences with the desired binding affinity and/or specificity. Jarosch et al. (2006) *Nucleic Acids Res.* 34:86 have described methods that allow the process to be performed without the constant primer regions.

In various embodiments, the selection process may involve steps in which the stringency of the elution conditions are gradually increased in order to select aptamers with high affinity for the target molecule.

In various embodiments, the selection process may involve steps in which the elution conditions are modified (e.g., by using a different affinity column) in order to select aptamers with desired specificity for the target molecule.

In various embodiments the selection process may generate a collection of sublibraries (or "pools") each of which comprises aptamers with similar affinities and/or specificities for the target molecule. In various embodiments the selection process may generate a single aptamer sequence (or "monoclonal"). In various embodiments the aptamers are DNA based. In various embodiments the aptamers are RNA based. In various embodiments the aptamers are mixed RNA/DNA aptamers.

Multivalent aptamers can be generated by covalently or non-covalently linking two or more of these monovalent aptamers into a single construct. An exemplary method is described in Example 4 below. Typically, two or more aptamers (which may have the same or different sequences) may be bound directly to one another (e.g., via a coupling agent) or indirectly through an independent framework. In various embodiments 2, 3, 4, 5, 6, 7 or 8 aptamers may be combined into a single construct. In various embodiments the 2, 3, 4, 5, 6, 7 or 8 aptamers may have the same sequence. It will be appreciated that either one of these approaches may require the aptamers to be chemically modified (e.g., to include pendant reactive groups) prior to coupling. It will also be appreciated that the aptamers of the present disclosure are not limited to a particular coupling reaction or framework (e.g., they can be prepared using frameworks that include polymeric and/or non-polymeric structures). It will further be appreciated that the frameworks may be linear, branched, hyperbranched and/or a combination of these. Exemplary frameworks and coupling chemistries are described below in the context of the conjugates.

In various embodiments the aptamers are covalently bound to each other or a framework. In such embodiments, the aptamers can be directly bound (i.e., with no intervening chemical groups) or indirectly bound through a spacer (e.g., a coupling agent or covalent chain that provides some physical separation between the aptamers or between the aptamers and framework). As discussed below in the context of the conjugates it is to be understood that aptamers may be covalently bound to each other or a framework through any number of chemical linkages, including but not limited to amide, ester, ether, isourea, and imine bonds.

In various embodiments, the two or more aptamers are non-covalently bound to each other or to a framework. In certain embodiments, the dissociation constant ($K_d$) of the non-covalent linkage in human serum is less than 1 pmol/L. For example, aptamers may be non-covalently bound to each other or a framework via a non-covalent ligand-receptor pair as is well known in the art (e.g., without limitation a biotin-avidin based pair). In such an embodiment, one member of the ligand receptor-pair is covalently bound to one aptamer while the other member of the pair is covalently bound to the other aptamer or framework. When the aptamers (or aptamers and framework) are combined, the strong non-covalent interaction between the ligand and its receptor causes the aptamers to become non-covalently bound to each other (or the framework). Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; *"Affinity Chromatography: Methods and Protocols (Methods in Molecular Biology)*" Ed. by Pascal Baillon, Humana Press, 2000; and *"Immobilized Affinity Ligand Techniques"* by Hermanson et al., Academic Press, 1992.

3. Chemical Modification of Cross-Linking Agents

In general, it is to be understood that any of the aforementioned multivalent cross-linking agents may be chemically modified, e.g., in order to mitigate undesirable properties.

i. Non-Specific Modifications

In US 2007-0110811 we described the benefits of pegylating lectins in order to reduce their in vivo mitogenicity. Thus, in certain embodiments, a multivalent cross-linking agent may be covalently modified with one or more compounds. Without limitation this might involve reaction with an activated pegylation (PEG) agent (e.g., without limitation N-hydroxysuccinimide activated PEG, succinimidyl ester of PEG propionic acid, succinimidyl ester of PEG butanoic acid, succinimidyl ester of PEG alpha-methylbutanoate, etc.), another water soluble but non-PEG-containing polymer such as poly(vinyl alcohol), a reagent that can be easily coupled to lysines, e.g., through the use of carbodiimide reagents, a perfluorinated compound, etc. The skilled artisan will readily recognize other suitable compounds, e.g., by referring to the comprehensive review that can be found in *"Chemical Reagents for Protein Modification"* by Lundblad, CRC Press, $3^{rd}$ Edition, 2004.

In general, the compound(s) may be attached to a multivalent cross-linking agent (e.g., a mitogenic lectin) via any of a number of attachment methods known to those skilled in the art (e.g., via amine, carboxyl, hydroxyl or sulfhydryl groups). The potential covalent linkages are similarly diverse (e.g., including amide bonds, carbamate bonds, ester bonds, thioether bonds, ether bonds, disulfide bonds, etc.). In certain embodiments suitable reactive groups can be grafted onto a multivalent cross-linking agent (e.g., a mitogenic lectin) by introducing an appropriate amino acid by site-directed mutagenesis as is known in the art. For example, PEGs are conveniently attached through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues may also be used as a reactive group for attaching the PEGs (or other compounds). In preferred embodiments PEGs are covalently attached to an amino group, especially the free amino group found in lysine residues.

Numerous methods for directly attaching PEGs to proteins are described in Delgado et al., *Crit. Rev. Thera. Drug Carrier Sys.* 9:249-304, 1992; Francis et al., *Intern. J. of Hematol.* 68:1-18, 1998; U.S. Pat. No. 4,002,531; U.S. Pat. No. 5,349,052; WO 95/06058; and WO 98/32466. One such method uses tresylated monomethoxy poly(ethylene glycol) (MPEG), which is produced by reacting MPEG with tresylchloride ($ClSO_2CH_2CF_3$). Tresylated MPEG reacts with exposed amine groups on lectins. A skilled person will recognize that the invention is not limited to any specific pegylation agent (or compound) and will be able to identify other suitable compounds that are known in the art.

In certain embodiments PEGs (or other compounds) may be attached to a multivalent cross-linking agent via an intervening linker. For example, U.S. Pat. No. 5,612,460, discloses urethane linkers for connecting PEG to proteins. PEGs can be attached to a protein via a linker by reaction with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional PEG derivatives and reaction chemistries for attaching PEG to proteins are described in WO 98/32466 and other patents, e.g., those that are assigned to Shearwater of Huntsville, Ala.; Nektar Therapeutics of San Carlos, Calif.; and/or Enzon Pharmaceuticals of Bridgewater, N.J. Catalogues can be obtained from these commercial PEG suppliers that describe a range of suitable PEG compounds and chemistries (e.g., see the Nektar Advanced PEGylation CATALOG 2004).

In various embodiments, N-terminal alpha-amine and/or epsilon-amino lysine groups of polypeptide based cross-linking agents may be succinylated and/or acetylated to change the charge distribution as well as any tertiary and quaternary effects associated with such changes. For example, polypeptides may be succinylated by reaction in a saturated sodium acetate buffer with an excess of succinic anhydride. Acetylation may be performed using the same procedure but with acetic anhydride as the modifying agent. For example, when the protein is concanavalin A, both acetylation and succinylation not only increase the density of negative charge within the polypeptide but also forces it to assemble as dimers instead of tetramers at physiological pH (e.g., see Agrawal et al., *Biochemistry.* 7:4211-4218, 1968 and Gunther et al., *Proc. Natl. Acad. Sci. (USA)* 70:1012-1016, 1973). In addition, the in vivo safety profile of these resulting materials is greatly improved as a result.

ii. Binding-Site Modifications

In certain embodiments, it may be advantageous to use an alternative and more specific method for modifying the multivalent cross-linking agents. In particular, we have found that certain low molecular weight conjugates of the present disclosure do not form insoluble drug delivery systems when combined with highly pegylated lectins made using high molecular weight PEG reagents (>5 kDa). This poses a challenge since we have previously found that lower molecular weight PEGs (<5 kDa) are much less effective in reducing lectin mitogenicity. Without wishing to be limited to any particular theory, it may be that the larger PEG groups are capable of sterically preventing binding and network formation with smaller low-valency conjugates, but not larger high-valency conjugates. In view of this, we devised an alternative non-PEG based solution for improving the safety profile of lectin-based cross-linking agents. We achieved this by specifically targeting and modifying the sugar binding site of lectins. For example, by reacting a mannose ligand directly into the concanavalin A binding site and purifying the unreacted material by high affinity ligand chromatography, we have been able to synthesize cross-linking agents with safety profiles that rival those of the best pegylated lectins. Without wishing to be limited to any particular theory, the functional concept appears to be that cell surfaces have a defined sugar affinity, valency, and ligand density, whereas the conjugates can have all of these properties adjusted by design. Thus, while incorporation of mannose into the lectin binding site completely abolishes the cross-linking agents ability to bind and thereby agglutinate or stimulate cells, incorporation of a higher density of higher affinity ligands on the conjugates still allows gel formation. In certain embodiments, incorporation of a small degree of pegylation with low MW, discrete PEG chains may be used to stabilize the multivalent lectins in solution under a variety of extreme storage conditions, yielding manufacturable, safe, functional cross-linking agents which complement the newly engineered conjugates.

In general, binding-site modified lectins will include at least one covalently linked affinity ligand which is capable of associating with one of the lectin binding sites. In various embodiments, the modified lectins may include just one covalently linked affinity ligand. In various embodiments, the lectins may include one covalently linked affinity ligand per binding site. Typically a multivalent lectin will include 2 or 4 binding sites (e.g., a dimer or tetramer of a monovalent lectin) but the present disclosure also encompasses lectins with 3, 5 or more binding sites. The present disclosure also encompasses lectins with more than one covalently linked affinity ligand per binding site. The present disclosure further encompasses materials which include a mixture of lectins that include different numbers of covalently linked affinity ligands and/or that include unmodified lectins.

Any affinity ligand can be used for this purpose as long as it can associate with a binding site of the lectin once covalently linked to the lectin. Typically an affinity ligand will include a recognition element which interacts with the lectin binding site and a reactive linker which enables the affinity ligand to become covalently attached to the lectin once the recognition element is bound within the binding site.

Recognition Element

Any recognition element that can compete for binding with the lectin's cognate ligand (e.g., glucose or mannose in the case of Con A) could be used in an affinity ligand of the present disclosure. In various embodiments, the recognition element includes a saccharide. In certain embodiments the saccharide is a natural saccharide (e.g., glucose, fructose, galactose, mannose, arabinose, ribose, xylose, etc.). In certain embodiments the saccharide is a modified saccharide (e.g., 2'-fluororibose, 2'-deoxyribose, hexose, etc.). In certain embodiments the recognition element is glucose, sucrose, maltose, mannose, derivatives of these (e.g., glucosamine, mannosamine, methylglucose, methylmannose, ethylglucose, ethylmannose, etc.) and/or higher order combinations of these (e.g., linear and/or branched bimannose, linear and/or branched trimannose, etc.).

Other exemplary saccharides will be recognized by those skilled in the art. In particular, it is to be understood that depending on the application any one of the saccharides that are described above in the context of the conjugate affinity ligands may be used (e.g., any one of the saccharides of formula IIIa or IIIb). In certain embodiments, the recognition element includes a monosaccharide. In certain embodiments, the recognition element includes a disaccharide. In certain embodiments, the recognition element includes a trisaccharide. In some embodiments, the recognition element includes a saccharide and one or more amine groups. In some embodiments, the recognition element is aminoethylglucose (AEG). In some embodiments, the recognition element is aminoethylmannose (AEM). In some embodiments, the recognition element is aminoethylbimannose (AEBM). In some embodiments, the recognition element is aminoethyltrimannose (AETM). In some embodiments, the recognition element is O-aminoethyl-N-acetylglucosamine (AEGA). In some embodiments, the recognition element is aminoethylfucose (AEF). In other embodiments, the recognition element is D-glucosamine (GA).

In various embodiments, the recognition element includes a polysaccharide, glycopeptide or glycolipid. In certain embodiments, the recognition element includes from 2-10 saccharide moieties, e.g., 2, 3, 4, 5, 6, 7, 8, 9 or 10 moieties. The terminal and/or internal residues of the polysaccharide, glycopeptide or glycolipid may be selected based on the saccharide specificity of the lectin in question (e.g., see Goldstein et al., *Biochem. Biophys. Acta* 317:500-504, 1973 and L is et al., *Ann. Rev. Biochem.* 55:35-67, 1986).

In various embodiments, the recognition element for a particular lectin/glucose combination may be selected empirically. According to such embodiments one or more recognition elements are screened based on their relative binding affinities for the lectin as compared to glucose. In certain embodiments a library of saccharides and/or polysaccharides are screened in this manner. A suitable recognition element will exhibit a detectable level of competition with glucose but will not compete so strongly that it prevents all binding between the lectin and glucose. In certain embodiments, different recognition elements may be screened by testing the effect of different affinity ligands on relevant lectin properties (e.g., based on their ability to inhibit agglutination and/or their material set points as discussed in more detail below and in the Examples). In certain embodiments, the recognition element will be selected in view of the conjugate that the modified lectin is to be combined with (e.g., so that the conjugate is able to displace the recognition element from the binding site and thereby form a cross-linked material).

Reactive Linker

Affinity ligands may be covalently linked to a lectin in any manner. Most methods will involve allowing the recognition element of the ligand to associate with the lectin binding site and then causing the reactive linker to react with the lectin. In certain embodiments, the reactive linker may be attached to the recognition element at a position that does not substantially interfere with the binding properties of the recognition element. For example, when the recognition element is a saccharide or polysaccharide the linker may be attached to the C1, C2 or C6 position of a terminal saccharide. In certain embodiments, the linker may be attached to the C1 position. The C1 position is also referred to as the anomeric carbon and may be connected to the linker in the alpha or beta conformation. In certain embodiments, the linker is attached to the C1 position as the alpha anomer.

In certain embodiments, photoactivatable linkers may be used. For example, Beppu et al., *J. Biochem.* 78:1013-1019, 1975, described a method in which an arylazido linker was activated using ultraviolet light to form a covalent bond between concanavalin A and a sugar derivative within the binding site. Similar results were recorded by Fraser et al., *Proc. Natl. Acad. Sci.* (*USA*) 73:790-794, 1976 using succinylated concanavalin A. A similar procedure has also been employed using ricin and a photoactivatable derivative of galactose as described by Houston, *J. Biol. Chem.* 258:7208-7212, 1983. Photoactivatable derivatives of complex glycopeptide ligands having a higher affinity for lectins than saccharides and disaccharides have also been described by Baenziger et al., *J. Biol. Chem.* 257:4421-4425, 1982. These derivatives were made by covalently linking a photoactivatable group to the peptide portion of the glycopeptide ligand.

In general, any photoactivatable linker may be used such as an aryl, purine, pyrimidine, or alkyl azide, a diazo or diazirine group, a benzophenone, or a nitrobenzene. A more comprehensive list of potentially useful photoactivatable linkers may be found in Fleming, *Tetrahedron* 51:12479-12520, 1995 as well as Brunner, *Annu. Rev. Biochem.* 62:483-514, 1993 and Wong, S. S. "Chemistry of Protein Conjugation and Cross-Linking", (1993), CRC Press, New York, pp. 168-194 which are incorporated herein by reference.

In various embodiments, the photoactivatable linker may include a diazirine group. Photoactivation of diazirine groups with ultraviolet (UV) light creates reactive carbene intermediates that can form covalent bonds through addition reactions with any amino acid side chain or peptide backbone within range of the linker. Long wavelength UV-light (about 320-370 nm, preferably about 345 nm) is typically used to activate diazirines (e.g., see Suchanek et al., *Nat. Methods* 2:261-268, 2005).

In various embodiments, the photoactivatable linker may include an aryl azide group. When aryl azide groups are exposed to UV-light they form nitrene groups that can initiate addition reactions with double bonds, insertion into C—H and N—H sites, or subsequent ring expansion to react as a nucleophile with primary amines. The latter reaction path predominates when primary amines are present in the sample. Without limitation, long wavelength UV-light (about 320-370 nm, preferably about 366 nm) is thought to be most efficient for substituted aryl azides (e.g., with hydroxy or nitro groups) while shorter wavelengths are thought to be most efficient for unsubstituted aryl azides. Suitable UV-light sources are available commercially, e.g., from Pierce, Rockford, Ill.

For example, in various embodiments the affinity ligand may be of the general formula: $R_e$-$L^1$ where $R_e$ is a recognition element and -$L^1$ is a linker. In certain embodiments $R_e$ is a saccharide moiety. In certain embodiments $R_e$ is a glucose or mannose moiety which is covalently bonded to the linker at the C1 position.

In certain embodiments -$L^1$ may be of the general formula (VIIIa):

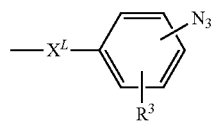

wherein:

$R^3$ is independently selected from the group consisting of hydrogen, —OH, —$NO_2$, and halogen (e.g., —F or —Cl);

$X^L$ is a covalent bond or a bivalent, straight or branched, saturated or unsaturated, optionally substituted $C_{1-20}$ hydrocarbon chain wherein one or more methylene units of $X^L$ are optionally and independently replaced by —O—, —S—, —N(R')—, —C(O)—, —C(O)O—, —OC(O)—, —N(R')C(O)—, —C(O)N(R')—, —S(O)—, —S(O)_2—, —N(R')SO_2—, —SO_2N(R')—, a heterocyclic group, an aryl group, or a heteroaryl group; and each occurrence of R' is independently hydrogen, a suitable protecting group, or an acyl moiety, arylalkyl moiety, aliphatic moiety, aryl moiety, heteroaryl moiety, or heteroaliphatic moiety.

In any case where a chemical variable is shown attached to a bond that crosses a bond of ring (for example as shown for $R^3$ above), this means that one or more such variables are optionally attached to the ring having the crossed bond. Each $R^3$ group on such a ring can be attached at any suitable position, this is generally understood to mean that the group is attached in place of a hydrogen atom on the parent ring. This includes the possibility that two $R^3$ groups can be attached to the same ring atom. Furthermore, when more than one $R^3$ group is present on a ring, each may be the same or different than other $R^3$ groups attached thereto, and each group is defined independently of other groups that may be attached elsewhere on the same molecule, even though they may be represented by the same identifier.

In certain embodiments, the —$N_3$ group is in the meta position. In certain embodiments, the —$N_3$ group is in the ortho position. In certain embodiments, the —$N_3$ group is in the para position.

In certain embodiments, one, two, three, four, or five methylene units of $X^L$ are optionally and independently replaced. In certain embodiments, $X^L$ is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of $X^L$ are optionally and independently replaced by —O—, —S—, —N(R')—, —C(O)—, —C(O)O—, —OC(O)—, —N(R')C(O)—, —C(O)N(R')—, —S(O)—, —S(O)_2—, —N(R')SO_2—, —SO_2N(R')— a heterocyclic group, an aryl group, or a heteroaryl group. In some embodiments, one or more methylene units of $X^L$ is replaced by a heterocyclic group. In some embodiments, one or more methylene units of $X^L$ is replaced by a triazole moiety. In certain embodiments, one or more methylene units of $X^L$ is replaced by —C(O)—. In certain embodiments, one or more methylene units of $X^L$ is replaced by —C(O)N(R')—. In certain embodiments, one or more methylene units of $X^L$ is replaced by —O—.

In some embodiments, $X^L$ is

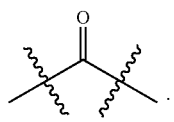 [SMILES: *C(*)=O]

In some embodiments, $X^L$ is

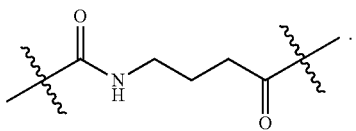 [SMILES: *C(=O)CCCNC(*)=O]

In some embodiments, $X^L$ is

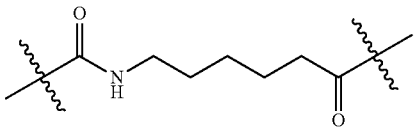

In some embodiments, $X^L$ is

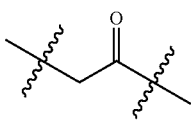

In some embodiments, $X^L$ is

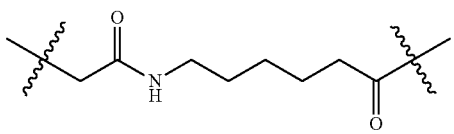

In some embodiments, $X^L$ is

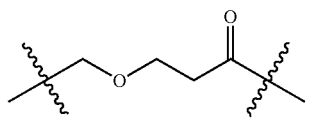

In certain embodiments -$L^1$ may be of the general formula (VIIIb):

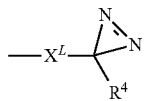

where $X^L$ is as defined above for formula VIIIa; and
$R^4$ is hydrogen, $C_1$-$C_6$ alkyl or —$CF_3$.

In certain embodiments, non-photoactivatable linkers may be used. For example, U.S. Pat. Nos. 5,239,062 and 5,395,924 describe linkers that can be activated by changes in pH or temperature. Exemplary reactive linkers which are discussed include those which can be introduced into an affinity ligand using reagents such as cyanuric chloride (Kay et al., Nature 216:514-515, 1967) or dichloro-S-triazines such as 2-amino-4,6-dichloro-S-triazine (Kay et al., Biochim. Biophys. Acta 198:276-285, 1970) and 2,4-dichloro-6-methoxy-S-triazine (Lang et al., J. Chem. Soc. Perkin 1:2189-2194, 1977). Reactive linkers with NHS-esters or aldehydes that would react primarily with terminal amines such as those found on lysines could also be used.

In various embodiments, the reactive linker for a particular lectin/target molecule combination may be selected empirically. According to such embodiments several affinity ligands with the same recognition element and different linkers (e.g., linkers of different lengths, linkers with different reactive groups, linkers with different hydrophobicity, etc.) are screened based on their effect on relevant lectin properties (e.g., based on their ability to inhibit agglutination and/or their material set points as discussed in more detail below and in the Examples).

iii. Extent of Modification

In general, the number of compounds that are attached to each multivalent cross-linking agent (i.e., the degree of substitution) will vary based on the nature of the cross-linking agent, the nature of the compound(s), the number of reaction sites available and the reaction conditions. For example, the subunits of concanavalin A each include twelve lysine residues. As a result, if concanavalin A is pegylated with a compound that reacts with lysine residues, then each subunit could be covalently linked to 1, 2, 3, 4, 5, 6, 7, 8, 9, 10, 11 or 12 of these compounds. Conversely, each subunit of concanavalin A includes just one glucose binding site. Thus, if concanavalin A is reacted with a compound that reacts at the binding site, then each subunit will be covalently linked to just one such compound. Methods for determining the degree of substitution are discussed in Delgado et al., Crit. Rev. Thera. Drug Carrier Sys. 9:249-304, 1992.

In preferred embodiments, the chemical modification of a multivalent cross-linking agent may be optimized using a plurality of compounds and a plurality of reaction conditions (e.g., that vary the reagent concentrations, pH, temperature, etc.). Preferred compounds and reaction conditions are such that desirable properties (e.g., binding affinity) are not substantially impaired while undesirable properties (e.g., mitogenicity) are reduced as compared to an unmodified cross-linking agent. For example, an automated robotic handling device may be used to prepare a range of modified compositions with different compounds and different reaction conditions. Using routine orthogonal experimentation a skilled person can then screen the properties of the treated compositions. In certain embodiments further rounds of orthogonal optimization are performed around the preferred conditions to further refine the preferred compounds and reaction conditions.

In one embodiment, optimal reaction conditions are identified by separating treated compositions by electrophoresis, preferably by denaturing SDS-PAGE electrophoresis. In various embodiments, compositions which include uniformly modified cross-linking agents are preferred. These preferred compositions will have weaker bands at the molecular weight of the unmodified cross-linking agent as measured by SDS-PAGE.

4. Purification of Cross-Linking Agents

In various embodiments, multivalent cross-linking agents (whether they have been chemically modified or not) can be further processed in order to improve their properties. Thus, in certain embodiments, compositions comprising multivalent cross-linking agents can be purified in order to remove protein fragments, unmodified components, etc. In general, these separations can be achieved on the basis of physical properties (e.g., electrical charge; molecular weight; and/or size) and/or chemical properties (e.g., binding affinity for a target molecule). In certain embodiments optimal removal may be achieved by combining two or more methods that rely on these differential properties. In one embodiment, these separations are performed under denaturing conditions. For example, unmodified or partially modified cross-linking agents can be removed on the basis of their net charge by ion-exchange chromatography. Gel-filtration chromatography may be used to discriminate between differentially modified cross-linking agents on the basis of size. Affinity chromatography is another method that may be used to remove unmodified or partially modified cross-linking agents. This approach takes advantage of the differential binding affinity of modified, partially modified and unmodified cross-linking agents for a specific target molecule.

5. Characterization of Cross-Linking Agents

In various embodiments, multivalent cross-linking agents (whether they have been chemically modified or not) can be screened or further tested in order to confirm or characterize their properties. Representative assays include: affinity assays, agglutination assays, T-cell mitogenicity assays, T-cell viability assays, antigenicity assays, etc.

Affinity assays may involve passing the multivalent cross-linking agent over an affinity column (e.g., a resin with the target molecule) and determining the elution conditions required to remove the cross-linking agent from the column. Equilibrium dialysis can also be used as is known in the art. Set point assays in which the cross-linking agent is combined with one or more conjugates of the present disclosure and then contacted with varying concentrations of the target molecule may also be used. Preferably the binding affinity of a chemically modified cross-linking agents is at least 75% that of the unmodified cross-linking agent. More preferably the binding affinity is at least 85% and yet more preferably at least 95% that of the unmodified cross-linking agent.

In certain embodiments, an agglutination assay may be used to determine the minimum agglutinating concentration (MAC) of a multivalent cross-linking agent. For example, in certain embodiments the MAC may be determined using rabbit erythrocytes as described in US 20070110811. We have found that higher MAC values correlate strongly with reduced mitogenicity in the case of chemically modified lectins. In certain embodiments a modified cross-linking agent may have a MAC that is higher than the unmodified cross-linking agent. Preferably the MAC is 25 times that of the unmodified cross-linking agent. More preferably the MAC is 50 times and yet more preferably more than 100 times that of the unmodified cross-linking agent. In certain embodiments, the modified cross-linking agent exhibits a MAC with a 2% v/v suspension of formaldehyde-stabilized rabbit erythrocytes that is greater than 4 ug/ml. Preferably the MAC is greater than 6 ug/ml, more preferably greater than 10 ug/ml, even more preferably greater than 25 ug/ml.

Mitogenicity assays will typically involve contacting the compositions of interest with a T-cell culture (e.g., PBMC cells) for a period of time and then measuring the level of T-cell proliferation. Various methods for measuring cell proliferation are known. In one embodiment the cell density may be measured spectrophotometrically at 450 nm. In another embodiment an indirect measure can obtained by detecting the reduction of MTT at 570 nm (e.g., see Ohno et al., *J. Immunol. Methods* 145:199-203, 1991). In preferred embodiments, the level of cell proliferation is determined using a tritiated thymidine uptake assay. Those skilled in the art will recognize that other suitable methods may be used and that the invention is in no way limited to a specific proliferation assay. In certain embodiments, the T-cell mitogenicity of a modified cross-linking agent is less than 50% the T-cell mitogenicity of the unmodified cross-linking agent. The reduction in T-cell mitogenicity may be assessed by performing a comparative thymidine uptake assay across a range cross-linking agent concentrations, e.g., 0.01, 0.1, 1, 10, 100 and 1000 ug/ml. In preferred embodiments, the thymidine uptake assay is performed with samples that include approximately 500,000 PBMCs. The mitogenicity of the test composition (e.g., a modified composition) is then expressed as the % maximal unmodified mitogenicity. The % maximal unmodified mitogenicity is obtained by dividing the maximal CPM (counts per minute) value for the test composition over all measured concentrations by the maximal CPM value of the unmodified composition over all measured concentrations. Preferably, the test composition with reduced mitogenicity induces a level of T-cell proliferation that is at least 50% lower than the unmodified composition. More preferably, the level is at least 75% lower, even more preferably at least 90%, 95% or 99% lower.

T-cell viability can be measured using a similar experiment by adding Trypan Blue to the T-cell culture and counting a representative sample of the cells (noting those that either take up the trypan or still exclude the trypan, i.e., those that become blue vs. those that do not). The % viability is then calculated by dividing the number of cells that exclude the trypan (alive, "not blue") by the total number of cells counted (dead, "blue," plus live, "not blue"). Those skilled in the art will recognize that other suitable methods may be used and that the invention is in no way limited to a specific viability assay. In certain embodiments, a modified cross-linking agent exhibits a percentage cell viability at 100 ug/ml that is greater than 10% when assayed using PBMCs at a concentration of 500,000 cells/ml. Preferably the percentage cell viability is greater than 25%, more preferably greater than 50%, even more preferably greater than 90%.

Cross-Linked Materials

When conjugates and cross-linking agents are combined in the absence of the target molecule, a non-covalently cross-linked material is formed. In various embodiments, the material may be prepared in aqueous solution through self-assembly by mixing solutions of the cross-linking agent and conjugate. In various embodiments, particles of the material may be prepared by reverse emulsion. As described in more detail in U.S. Patent Application Publication No. 2004-0202719, this can be achieved by adding the aforementioned aqueous solution to a mixture of a hydrophobic liquid and a surfactant and agitating the mixture.

Once formed, the cross-linked material can be used for a variety of applications. When the material is placed in the presence of free target molecules these compete for the interactions between the cross-linking agents and the conjugates. Above a certain concentration of free target molecule, the level of competition becomes such that the material begins to degrade by releasing conjugates from the surface. In various embodiments, the extent and/or rate of release increases as the concentration of target molecule increases. As a result, conjugates are released from the material in a manner which is directly tied to the local concentration of the target molecule.

In general, the release properties of the material will depend on the nature of the cross-linking agents, conjugates, target molecule and conditions (e.g., pH, temperature, etc.). If the affinity of the cross-linking agents for the conjugates is much greater than for the target molecule then the material will only release conjugates at high concentrations of target molecule. As the relative affinity of the cross-linking agents for the conjugates is decreased, release of conjugates from the material will occur at lower target molecule concentrations. The release properties of the material can also be adjusted by varying the relative amounts of cross-linking agent to conjugate. Higher ratios of cross-linking agent to conjugate will lead to materials that release conjugates at higher target molecule concentrations. Lower ratios of cross-linking agent to conjugate will lead to materials that release conjugates at lower target molecule concentrations. It will be appreciated that, depending on the application, these variables will enable one to produce materials which respond to a wide variety of target molecule concentrations.

In various embodiments, the cross-linked material is insoluble when placed in pH 7 HEPES buffered saline at 37 C (25 mM HEPES containing 150 mM NaCl). In various embodiments, the cross-linked material remains substantially insoluble when target molecule is added to the buffer up to a threshold concentration called the set point. Above the set point, the cross-linked material exhibits an increase in the extent and rate of release of conjugates. It will be appreciated that this transition may occur sharply or may occur gradually over a range of concentrations around the set point. In general, the desired set point and transition will depend on the nature of the target molecule and the intended application for the material. In particular, when the material is designed to respond to an increase in the level of a particular target molecule, the desired set point may be determined based on the normal physiological range of concentrations of the target molecule. It is to be understood that the amount of target molecule present in a patient may fluctuate based on internal and/or external factors. For example, in certain embodiments, the amount of target molecule may fluctuate naturally over time, e.g., in response to changes in hormonal cycles or metabolic pathways (lactate increasing during an endurance event, etc.). In certain embodiments, the fluctuations may result from an external event, e.g., an increase in glucose following a meal. In various embodiments, external factors may be used to artificially trigger the release of conjugates from a material of the present disclosure. For example, if release of conjugate is sensitive to an increase in glucose one could artificially release conjugates for a short period of time by ingesting a high-glucose drink.

In various embodiments, the target molecule is glucose. The normal physiological range of glucose concentrations in humans is 60 to 200 mg/dL. Glucose concentrations below 60 mg/dL are considered hypoglycemic. Glucose concentrations above 200 mg/dL are considered hyperglycemic. In various embodiments, a material of the present disclosure may remain substantially insoluble when placed in pH 7 HEPES buffered saline containing 20, 30, 40, 50, 60, 70, 80, 90, or 100 mg/dL glucose at 37 C for six hours using USP dissolution test method II at 50 rpm. In various embodiments, less than 1, 2, 4, 6, 8, or 10% of the material dissolves when placed in pH 7 HEPES buffered saline with 20, 30, 40, 50, 60, 70, 80, 90, or 100 mg/dL glucose at 37 C for six hours using USP dissolution test method II at 50 rpm. In various embodiments, at least 10, 20, 30, 40, 50, 60, 70, 80, 90 or 100% of a material of the present disclosure dissolves when it is placed in pH 7 HEPES buffered saline with 100, 150, 200, 250, 300, 350 or 400 mg/dL glucose at 37 C for six hours using USP dissolution test method II at 50 rpm.

The following tables provide normal physiological ranges for other exemplary target molecules:

|  | Low | High | Unit |
|---|---|---|---|
| Metabolites |  |  |  |
| Urea | 7 | 18 | mg/dL |
| Creatinine - male | 0.7 | 1.3 | mg/dL |
| Creatinine - female | 0.6 | 1.1 | mg/dL |
| Hormones |  |  |  |
| Thyroid stimulating hormone (TSH) | 0.4 | 4.7 | mIU/L |
| Free thyroxine (FT4) | 9 | 24 | pmol/L |
| Free triiodothyronine (FT3) | 2.5 | 5.3 | pmol/L |
| Adrenocorticotropic hormone (ACTH) | 1.3 | 15 | pmol/L |
| Cortisol (morning) | 250 | 850 | nmol/L |
| Cortisol (afternoon) | 110 | 390 | nmol/L |
| Prolactin (male) | n/a | 450 | mIU/L |
| Prolactin (female) | n/a | 580 | mIU/L |
| Testosterone (male post-puberty) | 8 | 38 | nmol/L |
| Testosterone (male pre-puberty) | 0.1 | 0.5 | nmol/L |
| Testosterone (female) | 0.3 | 2.5 | nmol/L |

It will be appreciated that the desired set point for these and other target molecules can be readily determined for a variety of different applications. It will also be appreciated that the set point may need to be adjusted for certain patients (e.g., based on patient gender, patients with abnormally low or high levels of a target molecule, etc.) or applications (e.g., a drug delivery system designed to release on a more frequent basis may require a lower threshold concentration than a system designed to release less frequently).

It will be appreciated that a material having a desired set point may be generated via routine experimentation using the materials and methods described herein. For example, the same cross-linking agent and conjugate can be combined to produce a series of materials with a gradually increasing ratio of cross-linking agent to conjugate (w/w). These materials will cover a spectrum of set points. Once a lead material with a suitable set point has been identified the process can be repeated with a finer resolution to yield an optimized material. Alternatively (or additionally) the same conjugate can be combined with a plurality of different cross-linking agents that have gradually increasing affinities for the conjugate. This will yield a plurality of materials with a spectrum of set points that can be further refined (e.g., by varying the w/w ratio of cross-linking agent to conjugate). Alternatively one could initiate the process by combining the same cross-linking agent with a plurality of different conjugates. In various embodiments, the conjugates may have varying affinities for the cross-linking agent (e.g., as a result of including different affinity ligands). In various embodiments, the conjugates may include the same affinity ligands but have different molecular weights (e.g., as a result of different conjugate frameworks).

Uses

In another aspect, the present disclosure provides methods of using the materials. In general, the materials can be used to controllably release conjugates in response to a target molecule. As discussed below, the material can be brought into contact with the target molecule in vitro or in vivo.

In various embodiments, a material may be used as a component of an in vitro or in vivo chemical sensor. This aspect is described below in the context of glucose sensors; however, it will be appreciated from the foregoing that other chemical sensors may be prepared by simply using a different target molecule.

For example, in various embodiments, a material of the present disclosure may be used in glucose sensors that are based on fluorescence resonance energy transfer (FRET). FRET is based on the fact that when two different fluorophores are brought closely together this allows for energy transfer between the two fluorophores, resulting in a decrease in the fluorescence of one or both of the fluorophores, which is called fluorescence quenching (Ballerstadt et al., *Anal. Chim. Acta* 345:203-212, 1997). In the absence of glucose, a mixture of a fluorescently labeled cross-linking agent and a fluorescently labeled conjugate will form an insoluble cross-linked material and the neighboring fluorophores will undergo FRET. In the presence of glucose, the average distance between the fluorescently labeled cross-linking agent and the fluorescently labeled conjugate will increase causing the level of FRET to decrease and thereby leading to an increase in the individual fluorescence signals. The level of fluorescence can thereby be directly correlated with the level of glucose.

In other exemplary embodiments, materials of the present disclosure may be used in viscosity-based glucose sensors (e.g., see U.S. Pat. Nos. 6,267,002; 6,477,891; and 6,938,463). Conjugates and cross-linking agents are again combined to form a cross-linked material. Addition of glucose to the material now causes a concentration dependent reduction in viscosity which can be measured (e.g., as a function of shear rate using a microviscometer set up in a cone-and-plate geometry). The viscosity of the sample can thereby be directly correlated with the level of glucose. It will be appreciated that these two exemplary glucose sensors do not require any drug to be present within the conjugates. It will also be appreciated that a viscosity-based sensor does not require a detectable label to be present within the conjugates.

In various embodiments, a material may be used to controllably deliver a drug to a patient. The invention encompasses treating a disease or condition by administering a material of the present disclosure. Although the materials can be used to treat any patient (e.g., dogs, cats, cows, horses, sheep, pigs, mice, etc.), they are most preferably used in the treatment of humans. A material can be administered to a patient by any route. In general the most appropriate route of administration will depend upon a variety of factors including the nature of the disease or condition being treated, the nature of the drug, the nature of the target molecule, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995.

In various embodiments, the material may be administered subcutaneously, e.g., by injection. The material can be dissolved in a carrier for ease of delivery. For example, the carrier can be an aqueous solution including, but not limited to, sterile water, saline or buffered saline. In general, a therapeutically effective amount of a drug in the form of a conjugate will be administered. By a "therapeutically effective amount" of a drug is meant a sufficient amount of the drug to treat (e.g., to ameliorate the symptoms of, delay progression of, prevent recurrence of, delay onset of, etc.) the disease or condition at a reasonable benefit/risk ratio, which involves a balancing of the efficacy and toxicity of the drug. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the drug. Although in general drugs having a large therapeutic index are preferred, as is well known in the art, a smaller therapeutic index may be acceptable in the case of a serious disease or condition, particularly in the absence of alternative therapeutic options. Ultimate selection of an appropriate range of doses for administration to humans is determined in the course of clinical trials.

In various embodiments, the drug is insulin and the average daily dose of insulin is in the range of 10 to 200 U, e.g., 25 to 100 U (where 1 Unit of insulin is ~0.04 mg). In certain embodiments, an amount of material with these insulin doses is administered on a daily basis. In certain embodiments, an amount of material with 5 to 10 times these insulin doses is administered on a weekly basis. In certain embodiments, an amount of material with 10 to 20 times these insulin doses is administered on a bi-weekly basis. In certain embodiments, an amount of material with 20 to 40 times these insulin doses is administered on a monthly basis. Those skilled in the art will be recognize that this same approach may be extrapolated to other approved drugs with known dose ranges, e.g., any of the approved insulin sensitizers and insulin secretagogues described herein.

It will be understood that the total daily usage of a drug for any given patient will be decided by the attending physician within the scope of sound medical judgment. The specific therapeutically effective amount for any particular patient will depend upon a variety of factors including the disease or condition being treated; the activity of the specific drug employed; the specific composition employed; the age, body weight, general health, sex and diet of the patient; the time of administration, route of administration and rate of excretion of the specific drug employed; the duration of the treatment; drugs used in combination or coincidental with the specific drug employed; and like factors well known in the medical arts. In various embodiments, a material of the present disclosure may be administered on more than one occasion. For example, the present disclosure specifically encompasses methods in which a material is administered by subcutaneous injection to a patient on a continuous schedule (e.g., once a day, once every two days, once a week, once every two weeks, once a month, etc.).

In certain embodiments, a material of the present disclosure may be used to treat hyperglycemia in a patient (e.g., a mammalian patient). In certain embodiments, the patient is diabetic. However, the present methods are not limited to treating diabetic patients. For example, in certain embodiments, a material may be used to treat hyperglycemia in a patient with an infection associated with impaired glycemic control. In certain embodiments, a material may be used to treat diabetes.

In various embodiments, a material of the present disclosure may be administered to a patient who is receiving at least one additional therapy. In various embodiments, the at least one additional therapy is intended to treat the same disease or disorder as the administered material. In various embodiments, the at least one additional therapy is intended to treat a side-effect of the primary drug. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, a single material of the present disclosure may include more than one drug for treating the same disease or disorder. In certain embodiments, two or more separate materials of the present disclosure may be administered (as a mixture or separately) that include different drugs for treating the same disease or disorder. In certain embodiments, an unconjugated secondary drug may be included in a material of the present disclosure (i.e., a drug which is simply mixed with the components of the material and not covalently bound to the cross-linked material). For example, in certain embodiments, any of these approaches may be used to administer more than one anti-diabetic drug to a subject. Certain exemplary embodiments of this approach are described in more detail below in the context of insulin-related therapies; however, it will be appreciated from the foregoing that other therapies will benefit from such combination approaches.

Insulin sensitizers (e.g., biguanides such as metformin, glitazones) act by increasing a patient's response to a given amount of insulin. A patient receiving an insulin sensitizer will therefore require a lower dose of an insulin-based material of the present disclosure than an otherwise identical patient would. Thus, in certain embodiments, a material comprising insulin conjugates may be administered to a patient who is also being treated with an insulin sensitizer. In various embodiments, the material of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the materials of the present disclosure are only effective for this subclass of patients when they release high levels of insulin-conjugates in a suitable timeframe. In certain embodiments, the treatment of this subclass of patients may be facilitated by combining the two approaches. Thus in certain embodiments, a traditional insulin-based therapy is used to provide a baseline level of insulin and a material of the present invention is administered to provide a controlled supplement of insulin when needed by the patient. Thus, in certain embodiments, a material comprising insulin conjugates may be administered to a patient who is also being treated with insulin. In various embodiments, the insulin may be administered at up to 75% of the normal dose required in the absence of the material of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Kits

A significant manufacturing advantage of the low molecular weight conjugates described herein was only realized after developing and testing cross-linked materials that had been prepared from these conjugates and affinity ligand modified lectins. Due to the low molecular weight of both the conjugates and affinity ligand modified lectins, the materials were found to form into a dispersion of particles rather than a single large volume gel network. This is significant because while cross-linked materials prepared with high molecular weight polymers and pegylated lectins flow easily through a narrow gauge needle once loaded and pressure is applied with the syringe plunger they cannot be pulled into a syringe with a narrow gauge needle. This means that the finished product needs to be pre-loaded into individual syringes, a complicated, costly process that does not readily lend itself to large scale production. The dispersions, on the other hand, can be manufactured in large quantities and loaded under aseptic conditions into conventional multi-use drug vials. In addition, given the large increase in drug mass loading per conjugate and the ratio at which the conjugate and affinity ligand modified lectins form optimal networks, the effective drug loading is about an order of magnitude higher in these materials versus materials prepared with high molecular weight conjugates. For example, the high mass loadings of insulin allow us to prepare dispersions containing up to 100 U/ml of insulin equivalents, the standard concentration used in all commercial insulin formulations. The dispersions are easily resuspended by gentle rolling just like other insulin products. Also like those commercial formulations, the new dispersions may be easily pulled up through a 28G needle to the appropriate dose volume and injected just like water without any significant pressure required. Incorporation of m-cresol as the bacteriostatic agent (used in all currently marketed insulin products) does not change the performance or safety profile and allows multiple daily usage for prolonged periods without any detectable microbial contamination. In various embodiments, the present disclosure therefore provides kits which include one or more vials with dispersion of cross-linked material.

In another aspect, the present disclosure provides libraries of conjugates and/or cross-linking agents. These libraries may be particularly useful for generating materials with a desired set point. In various embodiments, a library may include a plurality of conjugates which produce different set points with the same cross-linking agent. In various embodiments, a library may further include one or more cross-linking agents which form cross-linked materials with conjugates in the library. When the library includes more than one such conjugates, the different conjugates may have different molecular weights, a different number of affinity ligands per conjugate molecule and/or different affinity ligands. In various embodiments, a library may include one or more of the conjugates that include more than one type of affinity ligand.

EXAMPLES

I. Methods of Making Exemplary Conjugates

This first set of examples describes various methods for making exemplary conjugates. The examples also include assays for purifying and assaying the starting ingredients and final products. It is to be understood that these methods can be modified to produce other conjugates that fall within the scope of the invention.

Example 1

Synthesis of Azidoethylglucose (AzEG)

a. Synthesis of Bromoethyleglucose

DOWEX 50W×4 resin (Alfa Aesar, Ward Hill, Mass.) was washed with deionized water to remove color. A mixture of 225 gm D-glucose (1.25 mol; 1 equiv., Alfa Aesar) and 140 gm DOWEX 50W×4 was treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction was monitored by TLC (20% methanol/dichloromethane (DCM)). Reaction was complete after about four hours, and it was allowed to cool to room temperature. The solution was filtered to remove the resin, and the resin washed with ethyl acetate and DCM. The resulting filtrate was stripped to an amber oil in a rotary evaporator. A total of 400 gm after stripping.

The amber oil was purified on silica gel (4 kg silica packed in DCM) in the following manner. The crude was dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) were pooled and stripped to dryness to afford 152 gm of 1-α-bromoethyl-glucose (42%).

b. Conversion of Bromoethylglucose to Azidoethylglucose (AzEM)

A 5 L round bottom three-necked flask, equipped with a heating mantle, an overhead stirrer, and a thermometer, was charged with 150 gm bromoethylglucose (525 mmol). The oil was dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution was cooled to room temperature and concentrated to dryness on the rotovap. The solid residue was digested with 3×500 mL of 5:1 vol. CHCl$_3$:MeOH at 40 C. The combined organic portions were filtered and evaporated to dryness to afford azidoethylglucose (86 gm) as an off-white solid. TLC (20% MeOH/DCM; char with H$_2$SO$_4$): single spot, indistinguishable from the starting material.

c. Repurification of Azidoethylglucose 32 gm of azidoethylglucose was taken into 100 mL water. The turbid solution was filtered through a glass microfibre filter (Whatman GF/B). The golden filtrate was evaporated to a solid on a rotovapor. The solid was taken into methanol (100 mL) and the turbid solution was again filtered through a glass microfibre filter. The resulting pale yellow filtrate was stripped to a solid under vacuum.

The solid was taken into a minimum of methanol (50 mL) and ethyl acetate (150 mL) was added slowly with stirring. The heavy slurry was cooled and filtered. The solid was air dried (hygroscopic) and put in a 60 C oven overnight. TLC has very little origin material. Yield 15.4 gm. The Mother Liquor was evaporated under vacuum to a yellow gum. No attempt was made to further purify this material at this time.

Example 2

Synthesis of Azidoethylmannose (AzEM)

a. Synthesis of Bromoethylmannose

DOWEX 50W×4 resin (Alfa Aesar, Ward Hill, Mass.) is washed with deionized water to remove color. A mixture of 225 gm D-mannose (1.25 mol; 1 equiv., Alfa Aesar) and 140 gm DOWEX 50W×4 is treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction is monitored by TLC (20% methanol/dichloromethane (DCM)). Reaction is complete after about four hours, and then allowed to cool to room temperature. The solution is filtered to remove the resin, and the resin washed with ethyl acetate and DCM. The resulting filtrate is stripped to an amber oil in a rotary evaporator.

The amber oil is purified on silica gel (4 kg silica packed in DCM) in the following manner. The crude is dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) are pooled and stripped to dryness to afford 152 gm of 1-α-bromoethyl-mannose (42%).

b. Conversion of Bromoethylmannose to Azidoethylmannose (AzEM)

A 5 L round bottom three-necked flask, equipped with a heating mantle, an overhead stirrer, and a thermometer, is charged with 150 gm bromoethylmannose (525 mmol). The oil is dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution is cooled to room temperature and concentrated to dryness on the rotovap. The solid residue is digested with 3×500 mL of 5:1 vol. CHCl$_3$:MeOH at 40 C. The combined organic portions are filtered and evaporated to dryness to afford azidoethylmannose as an off-white solid.

c. Repurification of Azidoethylmannose 32 gm of azidoethylmannose is taken into 100 mL water. The turbid solution is filtered through a glass microfibre filter (Whatman GF/B). The filtrate is evaporated to a solid on a rotovapor. The solid is taken into Methanol (100 mL) and the turbid solution is again filtered through a glass microfibre filter. The resulting pale yellow filtrate is stripped to a solid under vacuum.

The solid is taken into a minimum of methanol (50 mL) and ethyl acetate (150 mL) is added slowly with stirring. The heavy slurry is cooled and filtered. The solid is air dried (hygroscopic) and put in a 60 C oven overnight. The Mother Liquor is evaporated under vacuum to a yellow gum.

Example 3

Synthesis of Azidoethylmannobiose (AzEBM)

The AzEM compound from Example 2 is selectively protected using benzene dimethyl ether, purified by column chromatography and subsequently reacted with benzyl bromide to give 1-α-(2-azidoethyl)-4,6-benzaldehyde diacetal-3-benzyl-mannopyranoside. The product is subsequently glycosylated with 1-α-bromo-2,3,4,6-tetrabenzoylmannopyranoside using silver triflate chemistry under rigorously anhydrous conditions to give the protected-azidoethylmannobiose product. The intermediate product is then deprotected to remove the benzoyl groups to give AzEBM.

Example 4

Synthesis of Azidoethylmannotriose (AzETM)

a. 1-α-bromo-2,3,4,6-tetrabenzoyl-mannose

To a 500 mL 3-neck flask containing a stir bar and nitrogen inlet was added 40 gm (60.9 mmole of pentabenzoylmannose and 80 mL methylene chloride. The resulting solution was cooled in an ice bath to <5 C, and 80 mL 33% HBr-acetic acid solution was added via an addition funnel at such a rate to maintain the reaction temperature <10 C. Upon complete addition (~30 min.) the ice bath was removed and stirring was continued for 3 hours.

The reaction solution was diluted with an equal volume (160 mL) of DCM and extracted successively with water (2×500 mL), saturated bicarbonate (2×50 mL) and Brine (1×50 mL), dried over magnesium sulfate and the solvent evaporated to give 41 gm of solid foam. (Theoretical yield 40.1 gm) and was stored under N$_2$ in a freezer. This material was used without further purification. The reaction was monitored by TLC: silica gel (Hexane/Ethyl Acetate, 7/3) starting material R$_f$ 0.65, product R$_f$ 0.8 UV visualization. $^1$H NMR (CDCl$_3$) δ 8.11 (d, 2H), 8.01 (m, 4H), 7.84 (d, 2H), 7.58 (m, 4H), 7.41 (m, 6H) 7.28 (t, 2H), 6.58 (s, 1H), 6.28 (m, 2H), 5.8 (m, 1H), 4.75 (dd, 1H) 4.68 (dd, 1H) 4.5 (dd, 1H).

b. 1-Azidoethyl-2,4-dibenzoylinannose

To a 1.0 L, 3-neck flask containing a stir bar, nitrogen inlet and 300 mL of anhydrous acetonitrile was added 25 gm 1-azidoethylmannose (100.4 mmole), and 50 mL triethyl orthobenzoate (220 mmole, 2.2 equiv.). The resulting slurry was stirred at room temperature and 0.8 mL (10 mmole) trifluoroacetic acid (TFA) was added neat. The solution cleared within 10 minutes and stirring was continued for an additional two hours, then 25 mL of 10% aqueous TFA was added and stirring was continued for an additional 2 hours to hydrolyze the intermediate to the ester isomers. The solvent was evaporated under vacuum to a viscous oil, which was triturated with 50 mL DCM and again evaporated to a viscous oil. Toluene (70 mL) was added to the residue and the viscous solution was seeded with 2,4-dibenzoylazidoethylmannose. A fine precipitate formed within 15 minutes and stirring was continued overnight at room temperature. The resulting heavy suspension was set in the freezer for 2-4 hours, then filtered and the solid washed with ice cold toluene (2×10 mL). The solid was air dried to a constant weight to give 21 gm (TY 22.85 gm @ 50% isomeric purity) of ~95% isomeric purity. The product was taken into 40 mL toluene, stirred for 1 hour and then set in the freezer for an additional 2 hours. The solid was filtered and washed (2×10 mL) with ice cold toluene and air dried to a constant weight to give 18.5 gm of the single isomer product 2,4-dibenzoylazidoethylmannose in 83% yield. The mother liquors contained the undesired isomer and a small amount of the desired isomer. The reaction was monitored by TLC: SG (Hexane/Ethyl Acetate 7/3) Starting Material $R_f$ 0.0, orthoester intermediate $R_f$ 0.9. (Hexane/Ethyl Acetate: 8/2) SM $R_f$ 0.8, desired isomer $R_f$ 0.4, un-desired isomer $R_f$ 0.2 $^1$H NMR 300 MHz (CDCl$_3$) δ 8.12 (t, 4H), 7.66 (t, 2H), 7.5 (m, 4H), 5.56 (t, 1H), 5.48 (m, 1H), 5.14 (m, 1H), 4.5 (dd, 1H), 4.0 (m, 2H), 3.8 (m, 3H), 3.56 (m, 1H), 3.44 (m, 1H).

c. Perbenzoylated-man(α-1,3)-man(α-1.6)-α-1-azidoethylinannopyranoside

To a 1.0 L 3-neck flask with a stir bar, nitrogen inlet was added 41 gm crude 1-bromo-tetrabenzoymannose (60.9 mmole, ~2.5 equiv.) in 185 mL DCM. To this was added 11.2 gm 2,4-dibenzoylazidoethylmannose (24.5 mmole) followed by 11.2 gm 4A sieves. The slurry was stirred a room temperature for 10 minutes and cooled to −15° C. in a methanol/ice bath.

In a separate dark vessel was added 190 mL toluene followed by 15.1 gm silver-trifluoromethanesulfonate (AgOTf) (58.8 mmole, 2.4 equiv.) and was stirred into solution in the dark. This solution was transferred to a large addition funnel, and added drop-wise to the stirring suspension while protecting the reaction from light. The reaction temperature was maintained <−10 C by adjusting the AgOTf addition rate. Upon complete addition (~30 minutes) the cold bath was removed and the reaction stirred for an additional 2 hours until a single product remained by TLC (SG, Hexane/Ethyl Acetate: 7/3, Bromo $R_f$ 0.9, azido $R_f$ 0.4, trios product $R_f$ 0.5, uv visualization).

Triethylamine (7 mL, 5.0 equiv.) was added followed by 200 mL DCM. The resulting slurry was filtered through a pad of silica gel and celite and washed with 2×75 mL DCM. The solvent was evaporated under vacuum and the residue taken into ethyl acetate and washed sequentially with water (2×100 mL), bicarb (2×50 mL), brine (1×75 mL) and dried over magnesium sulfate. The solvent was evaporated under vacuum to give 39 gm of solid foam (TY 39.5 gm). $^1$H NMR 300 MHz (CDCl$_3$) δ 8.3 (d, 2H), 8.2 (m, 8H), 7.85 (d, 4H), 7.75 (dd, 4H), 7.3-7.65 (m, 30H), 7.2 (t, 2H), 6.05 (m, 4H), 5.9 (t, 2H), 5.63 (m, 2H), 5.38 (s, 2H), 5.18 (d, 1H), 4.65 (m, 4H), 4.5 (m, 2H), 4.35 (m, 4H), 3.8 (m, 2H), 3.54 (m, 2H).

d. Man(α-1,3)-man(α-1.6)-α-1-azidoethylinannopyranoside

To a stirring suspension of 3.0 gm perbenzoylated-man (α-1,3)-man(α-1.6)-α-1-azidoethylmannopyranoside (1.86 mmole) in 40 mL methanol was added 0.2 mL 4.28M sodium methoxide in methanol. The resulting suspension was stirred 20 hours at room temperature giving a clear solution. The completion of the reaction was monitored by TLC, (SG, hexane/ethyl acetate: 8/2 SM $R_f$ 0.4, product $R_f$ 0.0).

The methanol was evaporated under vacuum giving an oily semi-solid. The residue was taken into ethyl acetate (50 mL) and stirred for 3 hours. The solid was filtered, washed with fresh ethyl acetate (2×20 mL) and air dried to a constant weight to give 1.09 gm (TY 1.07 gm) of product. The mother liquors contained residual methyl benzoate, the de-protection by-product.

Example 5

Synthesis of Aminoethyl-Sugars (AEG, AEM, AEBM, AETM) from Azidoethyl-Sugars (AzEG, AzEM, AzEBM, AzETM)

Figure 10:
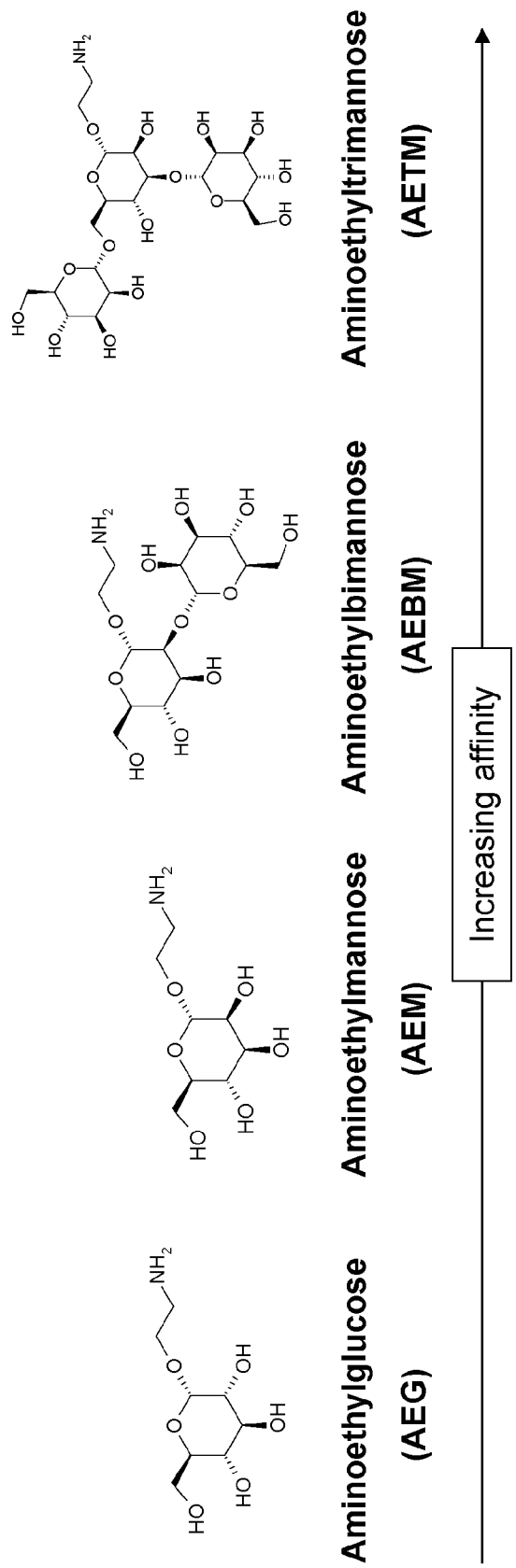
FIG. 10: Chemical structures of AEG, AEM, AEBM and AETM. The affinity of these sugar based affinity ligands for Con A increases as shown.
Figure 11:
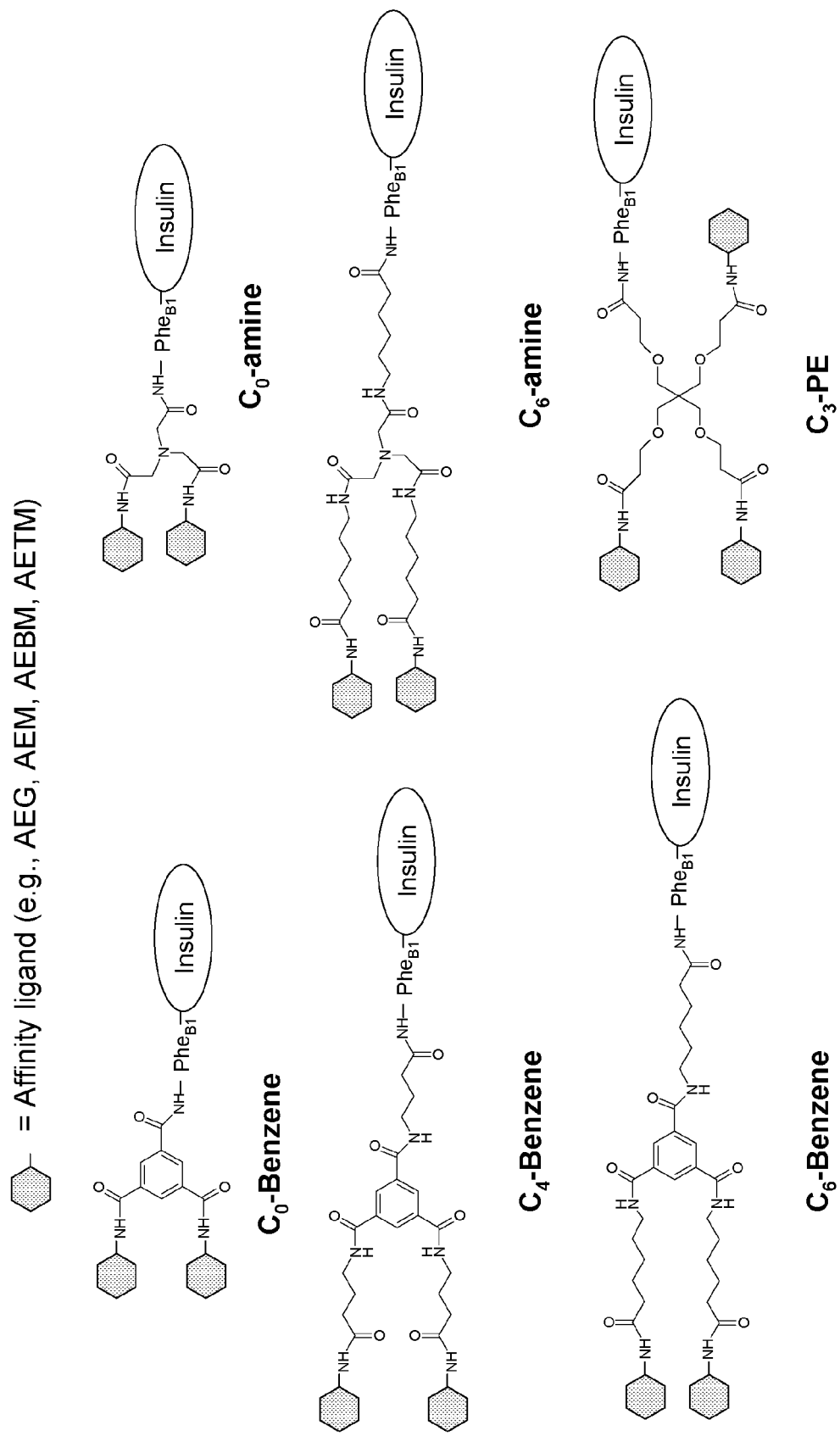
FIG. 11: Chemical structures of some exemplary non-dendrimeric conjugates.

The azido-terminated compounds from Examples 1-4 are readily hydrogenated at room temperature by using palladium/carbon catalyst, a small amount of acetic acid, and ethanol as a solvent to give the corresponding amine-terminated compounds. FIG. 10 shows the chemical structures of AEG, AEM, AEBM, AETM. The process is identical to the one described for AETM below, except that those skilled in the art will understand that the amounts of reagents, solvents, etc. should be scaled to the number of moles of sugar-ligand to be hydrogenated.

a. Man (α-1,3)-Man(α-1.6)-α-1-aminoethyltnannopyranoside ("aminoethyltrimannose", AETM)

To a solution of 5.3 gm (9.25 mmole) man(α-1,3)-man(α-1.6)-α-1-azidoethylmannopyranoside in 100 mL water and 50 mL ethanol was added 0.8 gm 5% Pd/C. The vigorously stirring suspension was hydrogenated at 30-40 psi for 48 hours or until no starting material was apparent by TLC (SG, Methanol, SM $R_f$ 0.75, Pdt $R_f$ 0.0, PMA vis.). The suspension was filtered over celite, which was rinsed with ethanol (2×50 mL) and the filtrate concentrated under vacuum.

HPLC of this material (C18, 3% Acetonitrile/97% 0.1% H$_3$PO$_4$, 220 nm, 2 ml/min) gave uv adsorption of the injection column void material, Rt 2.5 minutes, indicative of benzoate ester.

The filtrate was diluted with 70 mL water and 12 mL of 1N NaOH and the solution stirred overnight at room temperature (HPLC: no uv material at column void Rt 2.5 min., uv material at Rt 10.5 minutes co-eluting with benzoic acid). 2 gm of decolorizing charcoal were added and the stirring suspension heated to 80 C, cooled to room temperature and filtered over celite. The filtrate pH was adjusted to 8.0 with 2N HCl and the colorless solution concentrated under vacuum to about 50% volume.

The solution was loaded onto a resin column (Dowex 50W, 50 gm) and washed with water until eluting fractions were neutral to pH (6×75 mL) removing any residual acid by-products. The amine product was washed off the column with 0.25N ammonium hydroxide (6×75 mL) and the fractions containing the amine product-ninhydrin detection were combined and concentrated to 25-30 mL under vacuum. This concentrated solution was added drop-wise to 300 mL stirring ethanol and stirring continued for an additional 2 hours. The product was filtered, washed with fresh ethanol (2×50 mL) and air dried to a constant weight. The resulting white amorphous solid was dried further in a vacuum oven at 80 C for 5 hours to give 4.1 gm of a white granular solid (TY 5.1 gm). The NMR was clean of any aromatic protons. $^1$H NMR 300 MHz (D$_2$O) δ 5.08 (s, 1H), 4.87 (s, 1H), 4.81 (s, 1H), 4.8-3.6 (m, 18H), 2.9 (m, 2H).

Example 6

Dipropargyl Sugar Synthesis and Production of AE-Ligand a. Synthesis of Diethyl Diproparglymalonate Diethylmalonate (122.5 g, 0.7648 mol) was added to absolute ethanol (800 ml) containing sodium ethoxide (prepared from sodium metal, 38.5 g, 1.67 mol). After 30 min, propargyl bromide (200 g, 1.68 mol) was slowly added to the stirred suspension, keeping the temperature under 60 C. The mixture was refluxed overnight (15 hours). The precipitated salts were removed by filtration and washed with ethanol. Solvent was removed in vacuo, and the residue diluted with water and extracted with ethanol (2×200 ml). The combined extracts were dried over MgSO4, filtered, washed with Et2O and the solvent removed in vacuo to afford a golden colored oil. The oil was placed on high vacuum (40 C) for 3 hours and allowed to stand. Solids began to crystallize forming an oily solid. Let stand overnight (16 hours). Cyclohexane was charged to flask, solids broken-up, filtered, and washed with cyclohexane to afford white crystalline product (81 gm, 44.8% yield). Reaction was followed by GC.

b. Synthesis of Dipropargylmalonic Acid

Diethyl dipropargyl malonate (80 gm, 0.339 mol) was refluxed in 600 ml of 10% alcoholic potassium hydroxide overnight (15 hours). Solvent was removed in vacuo and the residue was acidified with 3N HCl. The residue was extracted with Et$_2$O (2×300 ml). The combined extracts were dried over MgSO4, filtered, washed with Et2O and concentrated in vacuo to an oil. Placed on high vac (40 C) for 2 hours and let stand to afford dipropargylmalonic acid as an oil (46 gm, 75.4% yield). Reaction was followed by GC.

c. Synthesis of Dipropargylacetic Acid

The dipropargylmalonic acid (26 gm, 0.443 mol) was heated neat at 135 C until CO$_2$ stopped evolving. It was then allowed to cool to an oil. The oil was distilled at 0.5 psi. The remaining oily residue in the distillation flask and solid were combined (15.7 gm, 79.9% yield) and was used as is in the next step.

d. Synthesis of [2-(3-prop-2-ynyl-hex-5-ynoylamino)-ethyl]-carbamic acid t-butyl ester N-boc-ethylenediamine (18.3 gm, 0.1143 mol) in 50 ml of CH$_3$CN was added slowly via an addition funnel to a stirred solution containing dipropargylacetic acid (15.56 gm, 0.1143 mol), TBTU (36.74 gm, 0.114 mol) and DIPEA (29.6 gm, 0.229 mol) in 300 ml of CH$_3$CN at 0 C. Precipitation occurred. The ice bath was removed and the product was stirred at ambient temperature overnight (16 hours). The reaction was now totally homogeneous. The solution was concentrated in vacuo and the residue was diluted with 800 ml of water. The resulting solids were filtered, washed copiously with water, and vacuum dried to give 14.3 gm of crude product. Re-crystallization (2×) from DCM, filtration and washing with hexanes affords the product (9.85 gm, 31% yield, 98% purity by HPLC (214 nm)).

e. Click Reaction of Azidosugar to [2-(3-prop-2-ynyl-hex-5-ynoylamino)-ethyl]-carbamic acid t-butyl ester To 1,1 dipropargyl-acetyl-(–1N,2N-BOC-1,2-diaminoethyl)amide (DP, 418 mg, 1.5 mmole) in DCM (20 mL) was added drop-wise TFA (4 mL) over 5 minutes at 0 C. The darkening solution was stirred at room temperature overnight. The volatiles were evaporated under reduced pressure. Toluene (20 mL) was added to the residue and stripped under reduced pressure two times. The resulting dark oil was used without further purification.

To this residue was added THF (20 mL) and water (20 mL) with stirring for 15 minutes. Copper Sulfate (225 mg, 0.9 mmole) was added followed by sodium ascorbate (180 mg, 0.9 mmole). The resulting mixture was heated to 55-60 C for 6 hours and then stirred at room temperature for 18 hours. The solution was evaporated under reduced pressure to approx. half volume and filtered through a microfibre glass filter. The resulting clear solution was placed on a resin column (Dowex 50X-2) which was washed with water (6×75 mL) until neutral pH, and then washed with 10% NH$_4$OH (8×75 mL). The fractions staining positive with Ninhydrin were combined and evaporated under reduced pressure to a glassy solid. The glass residue was taken into water (250 mL) and treated with 0.5 gm charcoal and heated to reflux. The cooled slurry was filtered over celite and a microfibre filter. The resulting pale yellow solution was evaporated to a glassy solid under reduced pressure and methanol was added and evaporated (2×) to give a off white foam (0.9 gm, TY 1.0 gm).

Example 7

Tripropargyl Sugar Synthesis and Production of AE-Ligand a. 2-(2-BOC-aminoethyl)thioacetamide-tris[(propargyloxy)methyl]aminomethane To a solution of t-butyl N-(2-mercaptoethyl)carbamate (Frontrun Organix, Ipswich, Mass.; 177.26 mg, 1 mmole) in ethanol (5 mL) was added NaOH (1.1 mmole) with stirring at room temperature. To this solution was added 2-bromoacetamide-tris[(propargyloxy)methyl]aminomethane (356 mg, 1.0 mmole, see *J. Org. Chem.* 73, 5602, 2008) and stirring was continued for 20 hours (TLC SG 8/2 hexane/ethyl acetate, pdt R$_f$ 0.4). The solvent was evaporated under vacuum and the residue was taken into ethyl acetate (40 mL) and washed successively with water (25 mL), 0.5 N NaOH (25 mL) and Brine (25 mL), dried over Na$_2$SO$_4$ filtered and concentrated to an oil (360 mg, TY 452.3 mg). NMR CDCl$_3$, (ppm): 7.05 (s, 1H, N—H); 5.25 ((s, 1H, N—H); 4.85 (s, 6H); 3.85 (s, 6H); 3.3 (m, 2H); 3.15 (s, 2H); 2.7 (m, 2H); 2.42 (s, 3H); 1.22 (s, 9H).

b. 2-(2-aminoethyl)thioacetamide-tris[(triazolo-1-(2-ethylmannose) 4-methoxy)methyl]aminomethane To a stirring solution of 2-(2-BOC-aminoethyl)thioacetamide-tris[(propargyloxy)methyl]aminomethane (1 gm, 2.21 mmole) in DCM (40 mL) at room temperature was added TFA (4 mL) dropwise. The resulting solution was stirred overnight. The solvents were removed under vacuum and the residue taken into toluene (15 mL) and evaporated to dryness.

The residue was taken into THF (40 mL), water (40 mL) and stirred into solution. Azidoethylmannose (3.75 eq., 2.0 gm, 8.3 mmole) was added followed by copper sulfate (500 mg, 2.0 mmole) and sodium ascorbate (400 mg, 2.0 mmole) and the resultant mixture stirred at 55-60 C (oil bath) for 6 hours, cooled to room temperature and stirred overnight. The resulting mixture was concentrated under vacuum to one half volume and filtered thru a micro-glass filter. The filtrate was loaded on a resin column (Dowex 50w 50×4-100) and eluted with water (6×75 mL) until neutral. The column was then eluted with 15% Ammonium Hydroxide (10×75 mL) and the fractions positive to ninhydrin were pooled and concentrated to a glassy foam (1.29 gm, TY (MW 1099 g/mol), 53% over two steps).

Example 8

Synthesis of $NH_2$-B1-BOC2(A1,B29)-Insulin

In a typical synthesis, 4 g of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.79 ml (2.6 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 µl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 µl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 60% of the desired BOC2 product and 40% of the BOC3 material.

A preparative reverse phase HPLC method is used to isolate the pure BOC2-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltraPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired BOC2 peak elutes at approximately 10.6 minutes followed closely by the BOC3 peak. Once collected, the solution is rotovapped to remove acetonitrile and lyophilized to obtain pure BOC2-insulin powder. Identity is verified by LC-MS (HT Laboratories, San Diego, Calif.) and site of conjugation determined by N-terminal sequencing (Western Analytical, St. Louis, Mo.).

Example 9

Synthesis of benzene-1,3,5-tricarboxy-(N-ω-aminoacid-NHS ester) amide frameworks A solution of 1,3,5-benzenetricarbonyl chloride (1 gm, 3.8 mmole) in dichloromethane (DCM) (5 mL) is added dropwise to a vigorously stirring solution of an ω-aminoacid (3.1 equivalents) in 1N NaOH (25 mL) in an ice bath. The ice bath is removed and stirring is continued for 4 hours at room temperature. 2N HCl (~15 mL) is added dropwise to approximately pH 2 and the resulting slurry is stirred for an additional 2 hours. The precipitate is filtered, washed with cold water (2×20 mL) and dried in air under vacuum and then in a 60 C oven overnight. The resulting white solid is used without further purification. Yield for each ω-aminoacid (4-aminobutyric acid: yield 1.6 gm, 91%; 6-aminocaproic acid: yield 1.9 gm, 92%)

The above material is taken into DMSO (5 mL) containing N-hydroxysuccinimide (3.1 mmole, 3.1 equiv.) and N-(3-dimethylaminopropyl)-N'-ethylcarbodiimide (EDCI, 3.6 mmole, 3.6 equiv.) is added at room temperature. The resulting solution is stirred for 24 hours, diluted with water (125 mL) and extracted with ethyl acetate (3×50 mL). The combined organic phase is washed with water (2×50 mL), brine (1×50 mL) and dried over $MgSO_4$. The solvent is evaporated and the semi-solid residue triturated with acetonitrile (10 mL). The solid is filtered and washed with cold solvent, dried in air under vacuum and then in a 60 C oven overnight. The product is free of urea bi-product. Benzene-1,3,5-tricarboxy-(N-6-aminocaproic-NHS ester)amide (TSB-C6): 304 mg, 36%, mp 140-142 C. Benzene-1,3,5-tricarboxy-($N^4$-butyric-NHS-ester)amide (TSB-C4): 245 mg, 45%, mp 182-184 C.

Example 10

Dendritic Framework Synthesis a. Hydrogenation of Nitro Group Containing, Alkyne-Terminally Functionalized Dendrons Dendrons containing either n=2, 4, or 8 terminal alkynes and a nitropropionic acid core are obtained (e.g., from Polymer Factory, Sweden) and used without further purification. The dendron is dissolved in 100 mL a 50:50 vol. mixture of DCM and ethanol, and 0.8 gm of 5% Pd/C is added. The vigorously stirring suspension is hydrogenated at 30-40 psi for 48 hours or until no starting material is apparent by TLC. The suspension is filtered over celite, which is rinsed with ethanol (2×50 mL) and the filtrate concentrated under vacuum.

The filtrate is diluted with 70 mL water and 12 mL of 1N NaOH and the solution stirred overnight at room temperature. 2 gm of decolorizing charcoal are added and the stirring suspension heated to 80 C, cooled to room temperature and filtered over celite. The filtrate pH is adjusted to 8.0 with 2N HCl and the colorless solution concentrated under vacuum to about 50% volume.

The solution is loaded onto a resin column (Dowex 50W, 50 gm) and washed with water until eluting fractions are neutral to pH (6×75 mL) removing any residual acid by-products. The amine product is washed off the column with 0.25N ammonium hydroxide (6×75 mL) and the fractions containing the amine product (ninhydrin detection) are combined and evaporated to vacuum using a rotary evaporator.

b. Reaction of Dendron (Amine, Alkyne-4) with Azidoethyl Mannose

The dendron product containing the amino core and four terminal alkyne groups obtained after hydrogenation (8.3 mmol) is taken into THF (40 mL), water (40 mL) and stirred into solution. Azidoethylmannose (4.75 eq., 2.53 gm, 10.51 mmole) is added followed by copper sulfate (500 mg, 2.0 mmole) and sodium ascorbate (400 mg, 2.0 mmole) and the resultant mixture stirred at 55-60 C (oil bath) for 6 hours, cooled to room temperature and stirred overnight. The resulting mixture is concentrated under vacuum to one half volume and filtered thru a micro-glass filter. The filtrate is loaded on a resin column (Dowex 50w 50×4-100) and eluted with water (6×75 mL) until neutral. The column is then eluted with 15% ammonium hydroxide (10×75 mL) and the fractions positive to ninhydrin are pooled and concentrated to a glassy foam.

Example 11

Amine-Functionalized Drug Conjugation with Multivalent Activated Esters in Organic Solvent (Drug Added First)

A framework containing N-terminal activated esters is dissolved at 60 mM in 1.0 ml of anhydrous DMSO followed by the addition of 400 ul (excess) of triethylamine (TEA). The solution is stirred rapidly for 10 minutes at room temperature. The amine-bearing drug is then dissolved separately in 7.9 ml of DMSO at a concentration of 7.4 mM. Once dissolved, the entire drug solution is added dropwise over the course of 10 minutes to the framework/DMSO/TEA solution followed by room temperature mixing for two hours. The remaining activated esters are then reacted with amine-functionalized affinity ligands in the following manner. A 370 mM solution of affinity ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then (3×(3-1)×60 mM/370 mM)=0.973 ml of affinity ligand solution are added. If there are N=4 initial activated ester groups per framework, then (3×(4-1)×60 mM/370 mM)=1.46 ml of affinity ligand solution are added, and so on. After the affinity ligand solution is added, the solution is stirred for one more hour at room temperature to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and affinity ligand used. Once collected, the solution is rotovapped to remove acetonitrile and lyophilized to obtain pure conjugate whose identity may be verified by LC-MS (HT Laboratories, San Diego, Calif.).

Example 12

B1-Insulin Conjugates with Multivalent Sugars—Homogeneous Ligand

Using the method described in Example 11 and the amine-bearing drug, $NH_2$-B1-BOC2(A1,B29)-insulin (MW=6,008 g/mol) of Example 8, drug conjugates were prepared with the following frameworks and affinity ligands. Tris-Succinimidyl-1,3,5-benzenetricarboxylate (TSB), tris-Succinimidyl aminotriacetate (TSAT), tris-Succinimidyl (6-aminocaproyl) aminotriacetate (TSAT-C6), and tetrakis-(N-succinimidyl carboxypropyl)pentaerythritol TSPE activated ester frameworks were purchased from Molecular Biosciences (Boulder, Colo.) and used without further purification. The TSB-C4 and TSB-C6 frameworks were synthesized according to Example 9. The AEM, AEBM, and AETM affinity ligands were synthesized according to Examples 1-4. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups were removed by dissolving the lyophilized powder obtained according to Example 11 in 90% TFA/10% anisole for one hour at 4 C followed by 10× superdilution in 25 mM HEPES pH 8.2 buffer containing 0.150M NaCl. The pH was adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to approximately 58 U of insulin/ml (based on A280 measurements) and stored at 4 C until needed. Because the starting $NH_2$-B1-BOC2(A1,B29)-insulin material only possesses one free amine group at the Phe-B1 terminus, the Phe-B1 is the only site of insulin conjugation to the framework as verified in each deprotected final product by N-terminal sequencing.

| | Synthesis Conditions | | | Product Characterization | | |
|---|---|---|---|---|---|---|
| Framework | Framework MW | Affinity ligand | AE-sugar MW | Purity (HPLC) | MW (LC-MS) | Sugar/ Insulin |
| TSB | 501 | AEM | 223 | 97% | 6410 | 2.0 |
| TSB | 501 | AEBM | 385 | 94% | 6734 | 2.0 |
| TSB | 501 | AETM | 547 | 96% | 7057 | 2.0 |
| TSB-C4 | 755 | AEM | 223 | 95% | 6665 | 2.0 |
| TSB-C4 | 755 | AEBM | 385 | 97% | 6989 | 2.0 |
| TSB-C4 | 755 | AETM | 547 | 95% | 7313 | 2.0 |
| TSB-C6 | 882 | AEM | 223 | 99% | 6791 | 2.0 |
| TSB-C6 | 882 | AEBM | 385 | 99% | 7114 | 2.0 |
| TSB-C6 | 882 | AETM | 547 | 95% | 7438 | 2.0 |
| TSAT | 482 | AEM | 223 | 98% | 6390 | 2.0 |
| TSAT | 482 | AEBM | 385 | 95% | 6714 | 2.0 |
| TSAT | 482 | AETM | 547 | 94% | 7038 | 2.0 |
| TSAT-C6 | 822 | AEM | 223 | 97% | 6730 | 2.0 |

-continued

| Framework | Synthesis Conditions | | | Product Characterization | | |
|---|---|---|---|---|---|---|
| | Framework MW | Affinity ligand | AE-sugar MW | Purity (HPLC) | MW (LC-MS) | Sugar/ Insulin |
| TSAT-C6 | 822 | AEBM | 385 | 99% | 7054 | 2.0 |
| TSAT-C6 | 822 | AETM | 547 | 97% | 7378 | 2.0 |
| TSPE | 813 | AEM | 223 | 98% | 6829 | 3.0 |
| TSPE | 813 | AEBM | 385 | 97% | 7314 | 3.0 |
| TSPE | 813 | AETM | 547 | 94% | 7802 | 3.0 |

Example 13

B1-Insulin Conjugates with Multivalent Sugars—Mixed Ligands

Using the method described in Example 11 and the amine-bearing drug, $NH_2$-B1-BOC2(A1,B29)-Insulin (MW=6,008 g/mol) of Example 8, insulin conjugates were prepared which possessed a mixture of sugar affinity ligands connected to the framework.

The TSAT-C6 and TSPE activated ester frameworks were purchased from Molecular Biosciences (Boulder, Colo.) and used without further purification. The AEM, AEBM, and AETM were synthesized according to Examples 1-4. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups were removed by dissolving the lyophilized powder obtained according to Example 11 in 90% TFA/10% anisole for one hour at 4 C followed by 10× superdilution in 25 mM HEPES pH 8.2 buffer containing 0.150M NaCl. The pH was adjusted to between 7.0 and 8.0 using NaOH solution after which the material was passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to the desired level and stored at 4 C until needed. Because the starting $NH_2$-B1-BOC2(A1,B29)-insulin material only possesses one free amine group at the Phe-B1 terminus, the Phe-B1 is the only site of insulin conjugation to the framework as verified in each deprotected final product by N-terminal sequencing.

| Framework | Framework MW | Mixed Affinity ligand | AE-sugar MW | Purity (HPLC) | MW (LC-MS) | Sugar/ Insulin |
|---|---|---|---|---|---|---|
| TSPE | 813 | AEM/ AETM (33/67 mol/mol) | 223/ 547 | 94% | 7478 | 1.0 AEM, 2.0 AETM |
| TSPE | 813 | AEM/ AETM (67/33 mol/mol) | 223/ 547 | 94% | 7152 | 2.0 AEM, 1.0 AETM |
| TSAT-C6 | 822 | AEM/ AEBM (50/50 mol/mol) | 223/ 385 | 96% | 6892 | 1.0 AEM, 1.0 AEBM |
| TSAT-C6 | 822 | AEBM/ AETM (50/50 mol/mol) | 385/ 547 | 95% | 7216 | 1.0 AEBM, 1.0 AETM |

Example 14

B1-Insulin Conjugates with Multivalent Sugars Using Premade Multivalent sugars Using the method described in Example 11 and the amine-bearing drug, $NH_2$-B1-BOC2(A1,B29)-insulin (MW=6,008 g/mol) of Example 8, the following insulin conjugates are prepared from pre-synthesized multivalent amine-containing affinity ligands. The disuccinimidyl suberate (DSS) and TSAT-C6 activated ester frameworks are purchased from Molecular Biosciences (Boulder, Colo.) and used without further purification. Divalent AEM-2, AEBM-2, and AETM-2 molecules containing a terminal reactive amine are prepared by conjugating two of each affinity ligand to a suitable framework to which a reactive amine is also conjugated. Trivalent AEM-3, AEBM-3, and AETM-3 molecules containing a terminal reactive amine are prepared by conjugating three of each affinity ligand to a suitable framework to which a reactive amine is also conjugated. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups are removed by dissolving the lyophilized powder obtained according to Example 11 in 90% TFA/10% anisole for one hour at 4 C followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to the desired level and stored at 4 C until needed. Because the starting $NH_2$-B1-BOC2(A1,B29)-Insulin material only possesses one free amine group at the Phe-B1 terminus, the Phe-B1 is the only site of insulin conjugation to the framework as verified in each deprotected final product by N-terminal sequencing.

| | Synthesis Conditions | | | Expected Product Characterization | |
|---|---|---|---|---|---|
| Framework | Framework MW | Affinity Ligand | AE-sugar MW | MW (LC-MS) | Sugar/ Insulin |
| DSS | 368 | AEM-2 | 676 | 6621 | 2.0 AEM |
| DSS | 368 | AEBM-2 | 1000 | 6945 | 2.0 AEBM |
| DSS | 368 | AETM-2 | 1324 | 7269 | 2.0 AETM |
| DSS | 368 | AEM-3 | 1085 | 7031 | 3.0 AEM |
| DSS | 368 | AEBM-3 | 1571 | 7517 | 3.0 AEBM |
| DSS | 368 | AETM-3 | 2057 | 8003 | 3.0 AETM |
| TSAT-C6 | 822 | AEM-2 | 676 | 7637 | 4.0 AEM |
| TSAT-C6 | 822 | AEBM-2 | 1000 | 8285 | 4.0 AEBM |
| TSAT-C6 | 822 | AETM-2 | 1324 | 8933 | 4.0 AETM |

-continued

| Synthesis Conditions | | | Expected Product | | |
|---|---|---|---|---|---|
| Framework | Framework MW | Affinity Ligand | AE-sugar MW | MW (LC-MS) | Sugar/Insulin Characterization |
| TSAT-C6 | 822 | AEM-3 | 1085 | 8046 | 6.0 AEM |
| TSAT-C6 | 822 | AEBM-3 | 1571 | 9018 | 6.0 AEBM |
| TSAT-C6 | 822 | AETM-3 | 2057 | 9990 | 6.0 AETM |

Example 15

B1-Insulin Conjugates with Multivalent Sugars Using Dendritic Framework—Homogeneous Ligand 0.1 gm (0.098 mmol) dendron containing an amino core and four terminal alkyne groups prepared in Example 10b is dissolved at 100 mg/ml in anhydrous DMSO. The solution is added dropwise to a solution containing disuccinimidyl suberate (DSS, Molecular Biosciences, 0.098 mmol) and triethylamine (400 uL) and allowed to react for 1 hour at room temperature. This mixture is then added dropwise to a 50 mg/ml solution containing the $NH_2$-B1-BOC2(A1,B29)-insulin (MW=6,008 g/mol) of Example 8 (0.588 g, 0.098 mmol) and allowed to react for 2 hours.

The resulting conjugate is superdiluted in water, and the pH adjusted to 8.0. The solution is desalted using BioGel P2, followed by concentration using Amicon 3k ultrafiltration devices. The resulting solution is purified by reverse phase chromatography, rotovapped to remove acetonitrile, and lyophilized. The BOC protecting groups are removed by dissolving the lyophilized powder in 90% TFA/10% anisole for one hour at 4 C followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to the desired level and stored at 4 C until needed. Because the starting $NH_2$-B1-BOC2(A1,B29)-insulin material only possesses one free amine group at the Phe-B1 terminus, the Phe-B1 is the only site of insulin conjugation to the framework and is verified in each deprotected final product by N-terminal sequencing.

Example 16

Synthesis of $NH_2$-B29-BOC2(A1,B1)-insulin a. Fmoc-1-(B29)-Insulin

In a typical synthesis, 4 gm of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.2 equivalents of 9-fluorenylmethyl N-succinimidyl carbonate (Fmoc-NHS) (Sigma Aldrich, St. Louis, Mo.) is slowly added to the insulin-TEA solution as a 1.0 M solution of the Fmoc-NHS in THF. The reaction is mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 μl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 μl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 20% of the Fmoc1 product, 65% of the Fmoc2 product, and 15% of unreacted insulin.

A preparative reverse phase HPLC method is used to isolate the pure desired Fmoc1-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltaPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired Fmoc1 peak elutes at approximately 3 minutes after the unreacted RHI peak, followed closely by the Fmoc2-insulin peak. Once collected, the solution is rotovapped to remove acetonitrile and lyophilized to obtain pure Fmoc1-insulin powder. Identity is verified by LC-MS (HT Laboratories, San Diego, Calif.) and site of conjugation determined by N-terminal sequencing (Western Analytical, St. Louis, Mo.).

b. BOC2(A1,B1)-Fmoc-(B29)-Insulin

In a typical synthesis, 1 g of Fmoc1-(B29)-insulin is dissolved in 25 ml of anhydrous DMSO at room temperature followed by the addition of 1 ml of triethylamine (TEA). The solution is stirred for 30 minutes at room temperature. Next, 0.379 ml (2.2 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 1 ml of a stock solution containing 250 ul of ethanolamine in 5 ml of DMSO followed by mixing for five minutes. After quenching, the entire solution is poured into 400 ml of acetone and mixed briefly with a spatula. Next, 8×100 μl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×100 μl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains greater than 90% of the desired BOC2-Fmoc-1 product.

A preparative reverse phase HPLC method is used to isolate the pure BOC2-Fmoc-1-insulin from the crude powder.

Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltraPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired BOC2-Fmoc-1 peak elutes at approximately 5 minutes after the Fmoc1-insulin starting material. Once collected, the solution is rotovapped to remove acetonitrile and lyophilized to obtain pure BOC2(A1,B1)-Fmoc(B29)-insulin powder. Identity is verified by LC-MS (HT Laboratories, San Diego, Calif.) and site of conjugation determined by N-terminal sequencing (Western Analytical, St. Louis, Mo.).

c. $NH_2$-(B29)-BOC2(A1,B1)-Insulin

The Fmoc protecting group of the BOC2(A1,B1)-Fmoc (B29) is removed by dissolving the lyophilized powder obtained according to the previous step in 20% piperidine in dimethylformamide (DMF) for 30 minutes at 4 C followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove Fmoc, DMF, and any other contaminating salts. The $NH_2$-(B29)-BOC2(A1,B1)-insulin is lyophilized into a powder if needed or used directly in aqueous solution if desired.

Example 17

Synthesis of $NH_2$-B29-BOC2(A1,B1)-Insulin Conjugates

All of the multivalent-affinity ligand-drug conjugates described in previous examples using the $NH_2$-B1-BOC2 (A1,B29)-insulin of Example 8 may be prepared instead using the $NH_2$-B29-BOC2(A1,B1)-insulin of Example 16. All of the resulting conjugates will possess the same MW and degree of substitution characteristics, but the site of conjugation to the insulin molecule will be at the epsilon B29 amino group and not the N-terminal Phe-B1. This can be confirmed by N-terminal sequencing.

Example 18

Amine-Functionalized Drug Conjugation with Multivalent Activated Esters in Organic Solvent (Drug Added Last)

This example describes an alternative to the method described in Example 11 in which the drug is added to the framework before the affinity ligand(s). In this example the affinity ligand(s) are added to the framework before the drug.

A framework containing N terminal activated esters is dissolved at 60 mM in 1 ml of anhydrous DMSO followed by the addition of 400 ul (excess) of triethylamine (TEA). The solution is stirred rapidly for 10 minutes at room temperature. In parallel, a 122 mM solution of affinity ligand is prepared in an appropriate volume of anhydrous DMSO. Once dissolved, enough affinity ligand solution is added dropwise over the course of ten minutes to provide a number of reactive equivalents equal to exactly the number of activated ester groups on the framework, N, minus one. For example, if there are N=3 activated ester groups on the framework, then (1×(3-1)×60 mM/122 mM)=0.98 ml of affinity ligand solution are added. If there are N=4 activated ester groups on the framework, then (1×(4-1)×60 mM/122 mM)=1.5 ml of affinity ligand solution are added, and so on. After the affinity ligand solution is added, the solution is stirred for two hours at room temperature.

The amine-bearing drug is then dissolved separately in 7.5 ml of anhydrous DMSO at a concentration of 8.1 mM. Once dissolved, the entire drug solution is added over the course of one minute to the framework/DMSO/affinity ligand/TEA solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and affinity ligand used. Once collected, the solution is rotovapped to remove acetonitrile and lyophilized to obtain pure conjugate whose identity may be verified by LC-MS (HT Laboratories, San Diego, Calif.).

Example 19

B29-Insulin Conjugates with Multivalent Sugars Produced in Organic Solvent from Unprotected Insulin This example makes use of the fact that in the unprotected insulin case, the Lys-B29 epsilon-amino moiety is the most reactive amine, followed by the A1 and then the B1. Therefore, when unprotected insulin is used as the amine-containing drug the resulting conjugate should be predominantly substituted at the Lys-B29 position. Using the method described in Example 18 and recombinant human insulin (MW=5808 Da, Sigma Aldrich, St. Louis, Mo.) as the amine-containing drug, the following insulin conjugates were prepared using the TSAT-C6 activated ester framework purchased from Molecular Biosciences (Boulder, Colo.). The AEM and AETM were synthesized as described previously. The appropriately sized size exclusion medium was Biogel P2 (Bio-Rad Laboratories, Hercules, Calif.), and the appropriately sized ultrafiltration membrane molecular weight cut-off was 3 kDa.

| Synthesis Conditions | | | Product Characterization | | |
|---|---|---|---|---|---|
| Framework | Framework MW | Affinity ligand | AE-sugar MW | Purity (HPLC) | MW (LC-MS) | Sugar/ Insulin |
| TSAT-C6 | 822 | AEM | 223 | 85% | 6729 | 2.0 |
| TSAT-C6 | 822 | AETM | 547 | 85% | 7378 | 2.0 |

According to N-terminal sequencing, approximately 85% of the AEM-containing framework was conjugated to insulin via the Lys-B29 and approximately 87% of the AETM-containing framework was conjugated to insulin via the Lys-B29.

Example 20

Amine-Functionalized Drug Conjugation with Multivalent Activated Esters in Aqueous Solvent (Drug Added Last)

This example describes an alternative to the method described in Example 18 in which the reaction is performed in aqueous solvent instead of organic solvent.

The framework containing N terminal activated esters is dissolved at 60 mM in 6.25 ml of anhydrous DMSO followed by the addition of 2 ml (excess) of triethylamine (TEA). The solution is stirred rapidly for 10 minutes at room temperature. In parallel, a 448 mM solution of affinity ligand is prepared in an appropriate volume of anhydrous DMSO. Once dissolved, enough affinity ligand solution is added dropwise over the course of ten minutes to provide a number of reactive equivalents equal to 1.5 times the number of activated ester groups on the framework, N, minus one. For example, if there are N=3 activated ester groups on the framework, then (1.5×(3-1)×60 mM/448 mM)×6.25 ml=2.5 ml of affinity ligand solution are added. If there are N=4 activated ester groups on the framework, then (1.5×(4-1)×60 mM/448 mM)×6.25 ml=3.8 ml of affinity ligand solution are added, and so on. After the affinity ligand solution is added, the solution is stirred for one hour at room temperature.

The amine-bearing drug is then dissolved separately at 17.2 mM in 2.67 ml of a 0.1M, pH 11 sodium carbonate buffer and the pH subsequently adjusted to 10.8 with 1.0N sodium hydroxide. Once dissolved, the entire framework/DMSO/affinity ligand/TEA solution is added dropwise over the course of 75 minutes to the drug/carbonate buffer solution. During the addition, the pH of the resulting mixture is adjusted every 5 minutes to 10.8 if necessary using dilute HCl or NaOH. The solution is allowed to stir for an additional 15 minutes after the dropwise addition to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 40 ml. This solution is further purified to obtain the desired product using preparative reverse phase HPLC on a Waters SymmetryPrep C18, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and affinity ligand used. Once collected, the solution is rotovapped to remove acetonitrile and lyophilized to obtain pure conjugate whose identity may be verified by LC-MS (HT Laboratories, San Diego, Calif.).

Example 21

B29-AEM-2-Insulin Conjugate Synthesized in Aqueous Solvent from Unprotected Insulin This example makes use of the fact that in the unprotected insulin case, the Lys-B29 epsilon-amino moiety is the most reactive amine, followed by the A1 and then the B1. Therefore, when unprotected insulin is used as the amine-containing drug the resulting conjugate should be predominantly substituted at the Lys-B29 position. Using the method described in Example 20 and recombinant human insulin (MW=5808, Sigma Aldrich, St. Louis, Mo.) as the amine-containing drug, an AEM-2 insulin conjugate was prepared using the TSAT-C6 activated ester framework purchased from Molecular Biosciences (Boulder, Colo.). The AEM used as the insulin analog was synthesized as described previously. The appropriately sized size exclusion medium was Biogel P2 (Bio-Rad Laboratories, Hercules, Calif.), and the appropriately sized ultrafiltration membrane molecular weight cut-off was 3 kD. The final product (95% pure by HPLC) was found to have the desired MW of 6729 g/mol (LC-MS), representing a total of 2.0 AEM molecules conjugated per insulin, with greater than 85% of the conjugate molecules conjugated at the Lys-B29 site (N-terminal sequencing).

Example 22

Generalized Amine-Functionalized Drug Conjugation with Aldehyde-Containing Framework a. Framework Functionalized with More than One Affinity Ligand and One Terminal Aldehyde First, a framework containing N terminal activated esters is dissolved at 60 mM in 27.0 ml of anhydrous DMSO followed by the addition of 800 ul (excess) of triethylamine (TEA). The solution is stirred rapidly for 10 minutes at room temperature. A stock solution of amine-bearing diethyl acetal is prepared at 580 mM in 5 ml of anhydrous DMSO. Once dissolved, 2.9 ml of the diethyl acetal solution are added dropwise over the course of 5 minutes to the framework/DMSO/TEA solution followed by room temperature mixing for an additional 15 minutes. The remaining activated esters are then reacted with amine-functionalized affinity ligands in the following manner. A 370 mM solution of affinity ligand is prepared in an appropriate volume of dry DMSO. Once dissolved, enough solution is added to provide a number of reactive equivalents equal to 1.5 times the number of initial activated ester groups, N, minus one. For example, if there are N=3 initial activated ester groups per framework, then (1.5×(3-1)×60 mM×27/370 mM)=13 ml of affinity ligand solution are added. If there are N=4 initial activated ester groups per framework, then (1.5× (4-1)×60 mM×27/370 mM)=20 ml of affinity ligand solution are added, and so on. After the affinity ligand solution is added, the solution is stirred for an additional hour and 45 minutes at room temperature to ensure complete reaction. After reaction, the entire solution is diluted by a factor of ten with diethyl ether, mixed vigorously, and centrifuged to separate the dense bottom phase containing the desired material from the supernatant. After discarding the supernatant, the same volume of ethanol is added to generate a solid precipitated mass. After centrifuging and discarding the supernatant, the material is washed extensively with ethanol and ether and then dried under vacuum to yield the crude framework containing multiple affinity ligands and a diethyl acetal group.

b. Conjugation of Amine-Functionalized Drug with Terminal Aldehyde

Once dried, the aldehyde group is generated from the diethyl acetal by dissolving the collected material in 60 ml of DI water with the solution pH adjusted to 1.0. The solution is mixed for 30 minutes after which 6 ml of a 200 mM HEPES pH 8.2 buffer containing 1.5 M NaCl is added and the solution pH adjusted to 6.5 using dilute NaOH solution. 48 mmol of the amine containing drug are added to the solution and the pH readjusted to 6.5 if necessary. Separately, a stock solution of reducing agent is prepared by dissolving 1.5 g of sodium cyanoborohydride (Sigma Aldrich, St. Louis, Mo.) in 15 ml of a 20 mM HEPES pH 7.0 buffer containing 0.150 M NaCl and the pH carefully adjusted to 6.5 with dilute HCl solution. 13 ml of the cyanoborohydride stock solution are added to the drug/framework/aldehyde solution and allowed to react overnight at room temperature.

The resulting aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and affinity ligand used. Once collected, the solution is rotovapped to remove acetonitrile and lyophilized to obtain pure conjugate whose identity may be verified by LC-MS (HT Laboratories, San Diego, Calif.).

Example 23

AEM-2-Framework Containing a Terminal Reactive Aldehyde Group and Subsequent Insulin Conjugation at B1 a. TSAT Functionalized with 2 AEM and 1 Aminobutyraldehyde Diethyl Acetal (ABDA)

This material is synthesized according to the method described in Example 22a using TSAT (Molecular Biosciences, Boulder, Colo.) as the multivalent activated ester framework and 4-aminobutyraldehyde diethyl acetal (Sigma Aldrich, St. Louis, Mo.) as the amine-bearing diethyl acetal. AEM (MW=223 g/mol), synthesized as described previously was used as the affinity ligand.

b. Conjugation of TSAT-AEM-2 ABDA with $NH_2$-B1-BOC2(A1,B29)-Insulin

This material was synthesized using the method described in Example 22b and the TSAT-AEM-2-ABDA produced in (a) above along with the amine-bearing drug, $NH_2$-B1-BOC2 (A1,B29)-insulin (MW=6,008 g/mol), synthesized according to Example 8. The appropriately sized size exclusion medium is Biogel P2 (Bio-Rad Laboratories, Hercules, Calif.), and the appropriately sized ultrafiltration membrane molecular weight cutoff is 3 kD. Because the starting $NH_2$-B1-BOC2 (A1,B29)-insulin material only possesses one free amine group at the Phe-B1 terminus, the Phe-B1 is the only site of insulin conjugation to the framework. The BOC protecting groups are removed by dissolving the lyophilized powder in 90% TFA/10% anisole for one hour at 4 C followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to the desired level and stored at 4 C until needed.

The final product (95% pure by HPLC) was found to have the desired MW of 6462 g/mol (LC-MS), representing a total of 2.0 AEM molecules conjugated per insulin, 99% of which were conjugated at the Phe-B1 site (N-terminal sequencing).

Example 24

AEM-3-Framework Containing a Terminal Reactive Aldehyde Group and Subsequent Insulin Conjugation at B1 a. TSPE Functionalized with 3 AEM and 1 Aminobutyraldehyde Diethyl Acetal (ABDA)

This material is synthesized according to the method described in Example 22a using TSPE (Molecular Biosciences, Boulder, Colo.) as the multivalent activated ester framework and 4-aminobutyraldehyde diethyl acetal (Sigma Aldrich, St. Louis, Mo.) as the amine-bearing diethyl acetal. AEM (MW=223 g/mol), synthesized as described previously, was used as the affinity ligand.

b. Conjugation of TSPE-AEM-3-ABDA with $NH_2$-B1-BOC2(A1,B29)-Insulin

This material was synthesized using the method described in Example 22b and the TSPE-AEM-3-ABDA produced in (a) above along with the amine-bearing drug, $NH_2$-B1-BOC2 (A1,B29)-insulin (MW=6,008 g/mol), synthesized according to Example 8. The appropriately sized size exclusion medium is Biogel P2 (Bio-Rad Laboratories, Hercules, Calif.), and the appropriately sized ultrafiltration membrane molecular weight cutoff is 3 kD. Because the starting $NH_2$-B1-BOC2 (A1,B29)-insulin material only possesses one free amine group at the Phe-B1 terminus, the Phe-B1 is the only site of insulin conjugation to the framework. The BOC protecting groups are removed by dissolving the lyophilized powder in 90% TFA/10% anisole for one hour at 4 C followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to the desired level and stored at 4 C until needed.

The final product (95% pure by HPLC) was found to have the desired MW of 6897 g/mol (LC-MS), representing a total of 3.0 AEM molecules conjugated per insulin, 99% of which were conjugated at the Phe-B1 site (N-terminal sequencing).

Example 25

AEM-3-Scaffold Containing a Terminal Reactive Aldehyde Group and Subsequent Insulin Conjugation at B1 Using Unprotected Insulin a. TSPE Functionalized with 3 AEM and 1 Aminobutyraldehyde Diethyl Acetal (ABDA)

This material is synthesized according to the method described in Example 22a using TSPE (Molecular Biosciences, Boulder, Colo.) as the multivalent activated ester scaffold and 4-aminobutyraldehyde diethyl acetal (Sigma Aldrich, St. Louis, Mo.) as the amine-bearing diethyl acetal. AEM (MW=223 g/mol), synthesized as described previously, was used as the indicator analog.

b. Conjugation of TSPE-AEM-3-ABDA with $NH_2$-B1-BOC2(A1,B29)-Insulin

This material was synthesized using the method described in Example 22b and the TSPE-AEM-3-ABDA produced in (a) above along with the amine-bearing drug, unmodified insulin (MW=5,808 g/mol, Sigma-Aldrich, St. Louis, Mo.). The appropriately sized size exclusion medium is Biogel P2 (Bio-Rad Laboratories, Hercules, Calif.), and the appropriately sized ultrafiltration membrane molecular weight cutoff is 3 kD. Although the starting unprotected insulin material possesses three free amine groups, the Phe-B1 is the predominant site of insulin conjugation to the scaffold due to the fact that the Phe-B1 (pKa~6.8) is the most reactive amine at pH 6.5. The lyophilized powder is dissolved in 25 mM HEPES pH 8.2 buffer containing 0.150M NaCl. The pH is adjusted to between 7.0 and 8.0 using NaOH solution after which the material is then concentrated using Amicon 3K membranes (Millipore, Billerica, Mass.) to the desired level and stored at 4 C until needed.

The final product (95% pure by HPLC) was found to have the desired MW of 6897 g/mol (LC-MS), representing a total of 3.0 AEM molecules conjugated per insulin, >85% of which were conjugated at the Phe-B1 site (N-terminal sequencing).

Example 26

Mixed Framework Chemistry and Corresponding Separate Conjugation of Drug and Affinity Ligands Succinimidyl-3,5-dimaleimidophenyl benzoate (SDMB) can be purchased from Molecular Biosciences (Boulder, Colo.) and used in the following example without further purification. SDMB is dissolved at 60 mM in 1.0 ml of anhydrous DMSO followed by the addition of 400 ul (excess) of triethylamine (TEA). The solution is stirred rapidly for 10 minutes at room temperature. The amine-bearing drug is then dissolved separately in 7.5 ml of anhydrous DMSO at a concentration of 8.1 mM. Once dissolved, the entire SDMB solution is added dropwise over the course of ten minutes to the DMSO-drug solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml.

Separately, 6.0 mmol of an amine-containing affinity ligand is dissolved in a 20 mM pH 8.2 HEPES buffered saline solution containing 0.150 M NaCl at a concentration of 450 mM. To this solution, 6.6 mmol of iminothiolane (Sigma-Aldrich, St. Louis, Mo.) is added and allowed to react at pH 8.2 for 30 minutes at room temperature to convert the amine-terminal groups to terminal sulfhydryl groups. The resulting material is mixed with the 10 ml solution of drug-framework-di-maleimide conjugate produced in the previous step. The maleimide groups are allowed to react with the indicator-analog sulfydryl groups at pH 8.2 for 2 hours to ensure complete reaction. The resulting solution is then purified by size exclusion using an appropriate solid phase for the desired separation of conjugated and unconjugated materials. The solution passing through the column void volume is then concentrated using an appropriately sized ultrafiltration membrane to approximately 10 ml.

Finally, this solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and affinity ligand used. Once collected, the solution is rotovapped to remove acetonitrile and lyophilized to obtain pure conjugate whose identity may be verified by LC-MS (HT Laboratories, San Diego, Calif.).

Example 27

Insulin-Conjugated to Aminoethylsugars Using Mixed Framework Chemistry

Using the method described in Example 26 and the amine-bearing drug, $NH_2$-B1-BOC2(A1,B29)-insulin (MW=6,008 g/mol), synthesized according to Example 8, the following specific drug conjugates are obtained. AEM (MW=223 g/mol), AEBM (MW=385 g/mol), and AETM (MW=547 g/mol) were synthesized as previously described and used as the affinity ligands in the synthesis. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups are removed by dissolving the lyophilized powder obtained according to Example 26 in 90% TFA/10% anisole for one hour at 4 C followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to approximately 58 U of insulin/ml (based on A280 measurements) and stored at 4 C until needed. Because the starting $NH_2$-B1-BOC2(A1,B29)-insulin material only possesses one free amine group at the Phe-B1 terminus, the Phe-B1 will be the only site of insulin conjugation to the framework. This can be verified in each deprotected final product by N-terminal sequencing.

| Synthesis Conditions | | | Expected Product | |
|---|---|---|---|---|
| | | AE-iminothiolane | Characterization | |
| Affinity Ligand | AE-sugar MW | intermediate MW | MW (LC-MS) | Sugar/ Insulin |
| AEM | 223 | 360 | 6822 | 2.0 AEM |
| AEBM | 385 | 522 | 7146 | 2.0 AEBM |
| AETM | 547 | 684 | 7470 | 2.0 AETM |

Example 28

Generalized Click Chemistry for Drug Conjugation with Complementary Frameworks

A framework (8.3 mmol) containing at least one amino functionality and one or more terminal alkyne groups is taken into THF (40 mL), water (40 mL) and stirred into solution. An azidoethyl group-bearing drug (10.51 mmole) is added followed by copper sulfate (500 mg, 2.0 mmole) and sodium ascorbate (400 mg, 2.0 mmole). The resulting mixture is stirred at 55-60 C (oil bath) for 6 hours, cooled to room temperature, stirred overnight and concentrated under vacuum to one half volume and filtered thru a micro-glass filter. The filtrate is loaded on a resin column (Dowex 50w 50×4-100) and eluted with water (6×75 mL) until neutral. The column is then eluted with 15% ammonium hydroxide (10× 75 mL) and the fractions positive to ninhydrin are pooled and concentrated to a glassy foam.

Example 29

Conjugates Prepared Using Natural Insulins from Other Species Such as Bovine and Porcine Insulins from other species which contain at least one reactive amine functionality (e.g., bovine and porcine insulin) may be coupled using any of the methods used to conjugate recombinant human insulin. Those skilled in the art will appreciate that the molecular weights of the resulting conjugates made from bovine or porcine insulins will differ from those made from recombinant human insulin by the amounts listed in the following table.

| Type of Insulin | Molecular Weight (g/mol) | Difference in MW human insulin (g/mol) |
|---|---|---|
| Human insulin | 5808 | — |
| Porcine insulin | 5778 | −30 |
| Bovine insulin | 5733 | −75 |

Those skilled in the art will also appreciate that the resulting conjugates made from bovine or porcine insulin may have chromatographic peak retention times that differ slightly from those conjugates made from human insulin, due to the small differences in structures between the insulins.

Example 30

Conjugates Prepared with Insulin Analogs Such as Lispro, Aspart, Glulysine, Glargine, and Detemir All known insulin analogs which contain at least one reactive amine functionality (e.g., Lispro, Aspart, Glulisine, Glargine, and Detemir) may be coupled using any of the methods used to conjugate recombinant human insulin. Those skilled in the art will appreciate that the molecular weights of the resulting conjugates made from insulin analogs will differ from those made from recombinant human insulin by the amounts listed in the following table.

| Type of Insulin | Molecular Weight (g/mol) | Difference in MW human insulin (g/mol) |
|---|---|---|
| Human insulin | 5808 | — |
| Insulin lispro | 5808 | — |
| Insulin aspart | 5832 | +24 |
| Insulin glulisine | 5823 | +15 |
| Insulin glargine | 6063 | +255 |
| Insulin detemir | 5913 | +105 |

Those skilled in the art will also appreciate that the resulting conjugates made from insulin analogs may have chromatographic peak retention times that differ slightly from those conjugates made from human insulin, due to the small differences in structures between the insulins.

The use of insulin glulisine (which does not contain a B29 lysine, but rather a B3 lysine) will give predominantly B3 conjugates when using unprotected insulin glulisine. However, if B1-insulin glulisine conjugates are desired, then BOC-(A1,B3)-insulin glulisine is first synthesized using the same protocol as BOC-(A1,B29)-human insulin as described in Example 8.

Example 31

Conjugates Prepared with Peptidic Insulin Secretagogue Conjugates

Peptidic insulin secretagogues (e.g., without limitation GLP-1 or the GLP-1 analog exanitide) which contain an N-terminal amine functionality may be coupled using any of the methods used to conjugate insulin.

II. In Vitro Assays of Exemplary Conjugates

This second set of examples describes various experiments investigating the in vitro properties of some exemplary conjugates.

Example 32

Synthesis of Insulin-Glycogen Conjugates

This comparative example describes the synthesis of an insulin-glycogen conjugate according to U.S. Patent Application Publication No. 20070099820. Briefly, 1 gm of commercially available, unpurified oyster glycogen (Type II, Sigma-Aldrich, St. Louis, Mo.) is dissolved in deionized water at a concentration of 10 mg/ml. Solid CNBr is added to the resulting solution at a CNBr to glycogen mass ratio of 0.68 and the pH maintained constant at 10.7+/−0.2 using 3N sodium hydroxide (NaOH) solution. After stirring for 15 minutes, another equal mass of solid CNBr equal is added and the pH maintained constant at 10.7+/−0.2 while stirring for 45 minutes. Insulin is then added to the solution at an insulin to glycogen mass ratio of 0.60 and the pH adjusted to 9.15 using solid sodium bicarbonate. The solution is stirred overnight, ultrafiltered exhaustively against deionized water using a 50 kDa MWCO polyethersulfone disc membrane filter (Millipore, Bedford, Mass.), and lyophilized. The resulting powder is then purified from unconjugated insulin by gel filtration HPLC (Waters, Milford, Mass.) using a 1 M acetic acid mobile phase over a Superdex™ 30 HiLoad 16/60 (Amersham Biosciences, Piscataway, N.J.) packed column. The insulin glycogen fraction is then lyophilized to obtain the conjugate as a pure white powder. The resulting purified material contained 1.0 wt % of insulin per insulin-glycogen conjugate as measured using amino acid analysis (UCLA Biopolymers Laboratory, Los Angeles, Calif.).

Example 33

Liquid Chromatography Analysis

This example describes the differences between the RP-HPLC profiles of insulin-glycogen synthesized according to Example 32 and an exemplary conjugate synthesized according to the present invention. 100 ul of a 5 mg/ml solution of insulin-glycogen synthesized according to Example 32 and 100 ul of a 1 mg/ml solution of exemplary conjugate were injected separately onto a Waters Symmetry C8 Sum column (4.6 mm×250 mm), equilibrated with a 80% Water/20% Acetonitrile (CH3CN) mobile phase (each containing 0.1% TFA). The exemplary conjugate used in this study was synthesized using TSAT-C6 as the framework, AEM as the affinity ligand, and $NH_2$-B1-BOC2(A1,B29)-insulin as the drug.

Figure 1:
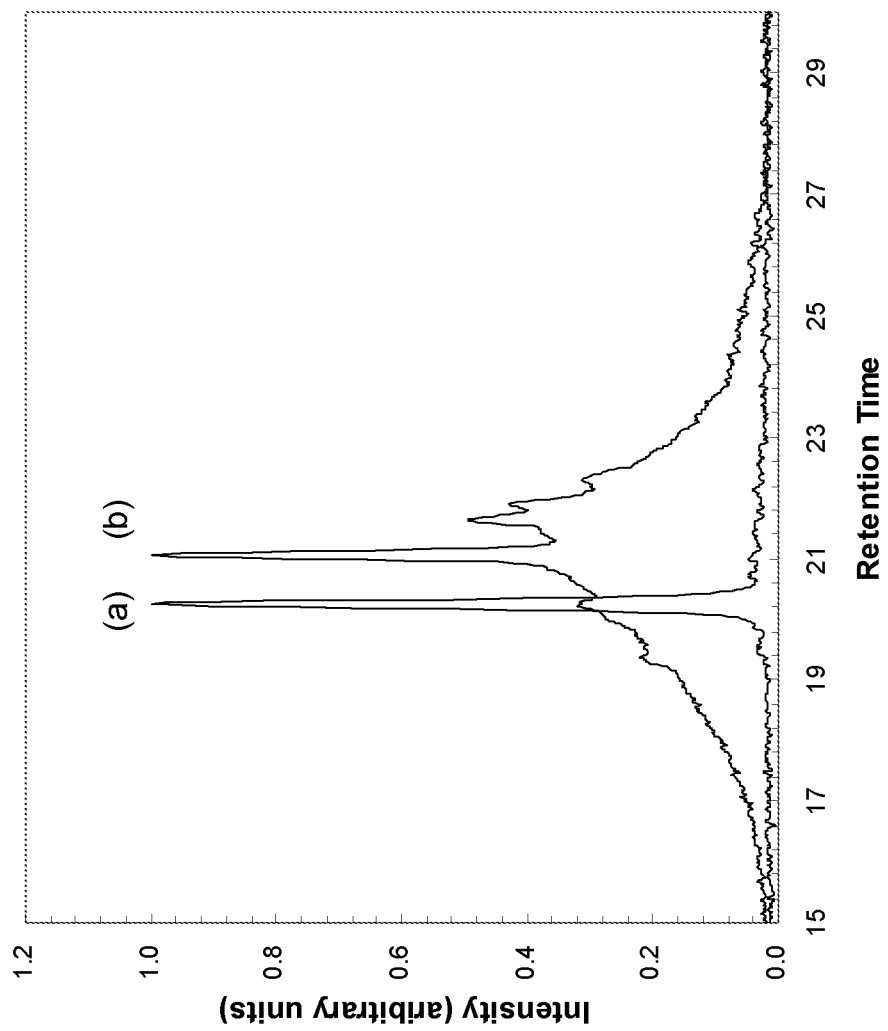
FIG. 1: Comparison between RP-HPLC chromatograms obtained for (a) exemplary conjugate synthesized using TSAT-C6 as the scaffold, AEM as the affinity ligand, and NH2-B1-BOC2 (A1,B29)-insulin as the drug and (b) an insulin-glycogen conjugate synthesized according to Example 32.

The samples were eluted at 1.0 ml/minutes using the following gradient method: 0-5 minutes—constant 80% Water/20% CH3CN, 5-35 minutes—linear gradient to 50% Water/50% CH3CN. The elution profiles in FIG. 1 show a single spike for the exemplary conjugate indicating a single chemically distinct species as compared to a broad and heterogenous elution profile for the insulin-glycogen conjugate, indicating a broad distribution of different chemical and/or molecular weight entities.

Example 34

Molecular Weight Distribution Analysis

This example describes the difference in MW and MW distribution between the insulin-glycogen synthesized according to Example 32 and the same exemplary conjugate. The MW and MW distribution of the insulin-glycogen conjugate was determined by injecting 1 ml of a 25 mg/ml solution in pH 7 HEPES buffered saline onto an Ultrahydrogel Size Exclusion Column (Waters Corporation, Millford, Mass.) equilibrated with HEPES buffered saline. The column was eluted over the course of 30 minutes at 0.5 ml per min, and the elution profile was measured as an absorbance at 280 nm. In separate experiments using the same protocol, dextran MW standards of 1000, 5000, 12000, 25000, 50000, 80000, 150000, 270000, and 410000 g/mol (Sigma-Aldrich, St. Louis, Mo.) were injected to establish a calibration curve of MW versus retention time. Based on the calibration curve and the elution profile of the insulin-glycogen conjugate, the average MW was determined to be 500,000 g/mol with 67% of the distribution eluting over the broad range of 250,000 to 1,000,000 g/mol (data not shown). In contrast, the exemplary inventive conjugate was determined to have just a single MW of exactly 6,730 g/mol as determined by LC/MS (HT Laboratories, San Diego, Calif.) (data not shown).

Example 35

Chemical and Physical Stability of Conjugates

Figure 2:
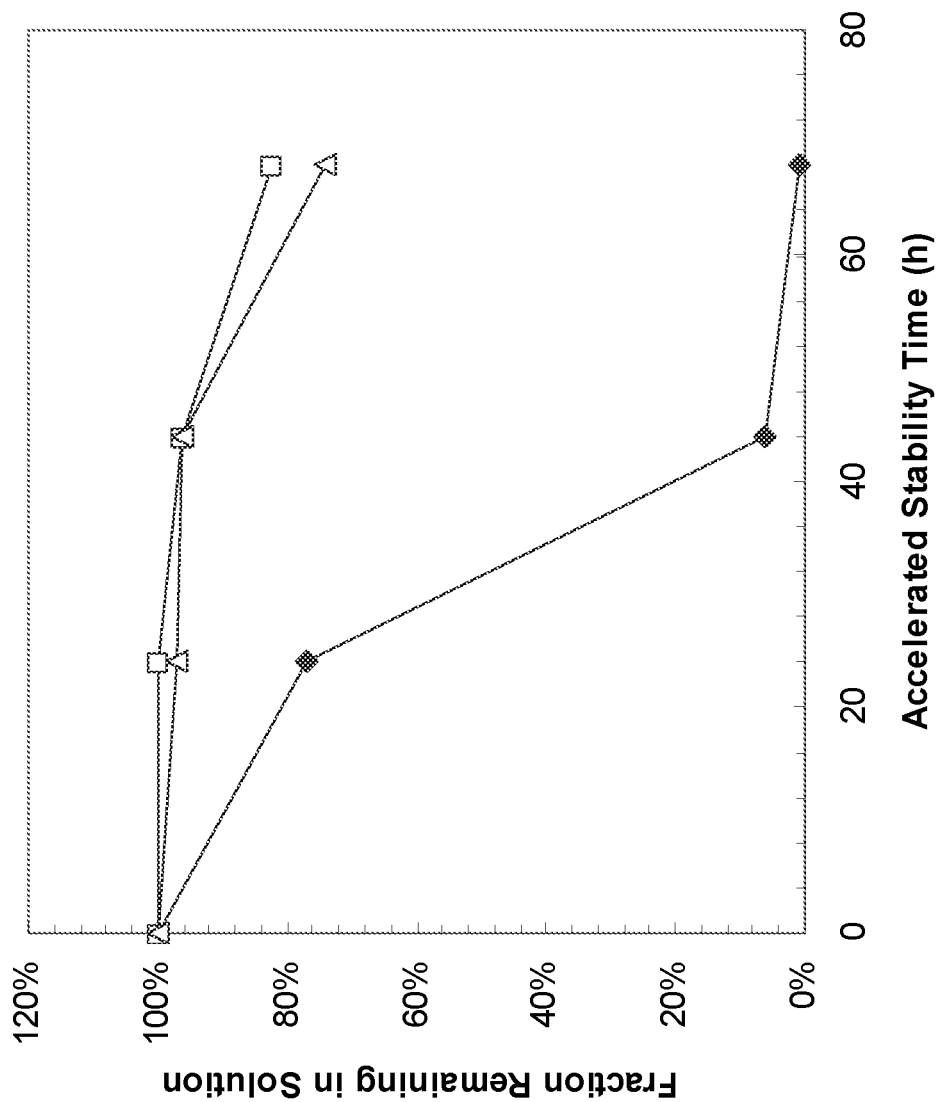
FIG. 2: Accelerated stability testing (AST) aggregation assay for Conjugate 1 (□), Conjugate 2 (Δ), and RHI (◆) in PBS buffer. The conjugates demonstrate greatly enhanced stability over pharmaceutical grade RHI.

This example compares the stability of an exemplary inventive conjugate with that of unconjugated insulin under accelerated conditions according to the method described in Hinds et al. (*Bioconj. Chem.* 11:195-201, 2000) at 37 C and a mechanical agitation rate of 150 strokes/min. Pharmaceutical grade recombinant human insulin (RHI) was selected as the control for the accelerated stability study. Holcombe et al. (*Diabetes Care* 27:1241-1242, 2004) describes that under non-accelerated conditions RHI stability is maintained for at least 30 days at room temperature (RT) and considerably longer when refrigerated. FIG. 2 shows the results from the aggregation stability assay for RHI and two exemplary conjugates in pH 7.4 phosphate buffered saline (PBS) at 50 U/ml. In all cases, the % remaining in solution was determined by centrifuging (4500×g, 5 min) the solution at a given time point, measuring the A280 of the supernatant, and dividing the supernatant A280 by that of the original starting solution. Conjugate 1 was synthesized using TSAT-C6 as the framework, AEM as the affinity ligand, and $NH_2$-B1-BOC2(A1, B29)-insulin as the drug. Conjugate 2 was synthesized using TSPE as the framework, AEM as the affinity ligand, and $NH_2$-B1-BOC2(A1,B29)-insulin as the drug.

After 48 hours of continuous agitation at 37 C, less than 6% of the RHI remained stable in solution, while the majority of the RHI precipitated out as insoluble aggregates. After the same amount of time, the both conjugates remained substantially more stable, as 96%-99% of the IPC's remained intact and soluble in the PBS solution. The data conclusively show that the conjugates are significantly more stable than RHI under these conditions.

RP-HPLC was used to assess the chemical stability of the conjugates (see FIG. 3a). After 48 hours of accelerated stability the conjugate solutions were analyzed using a C8-reverse phase column using a water-acetonitrile elution gradient. The retention times of the pre- and post-stability conjugate samples are shown along with the percentage of unconjugated (free) insulin and desamido insulin found in the resulting LC traces. No detectable amounts of free insulin or desamido were observed, indicating that (i) the covalent linkage between the sugars and the insulin molecule is stable, and (ii) no significant chemical degradation of the conjugate occurs during the accelerated stability test (AST). Prior to and in parallel with the AST, the conjugate was also subjected to a 90-day non-accelerated stability test that included daily thermal cycling between 4° C. and RT. At the conclusion of the parallel study, RP-HPLC demonstrated that the conjugate was still chemically and physically stable (data not shown).

Further confirmation of the conjugate chemical stability in HEPES buffer is provided from the LC-MS data obtained before and after subjecting the conjugate to the AST. Interestingly, the 48 hour AST conjugate samples in PBS showed that substantial degradation had occurred, while the 48 hour AST conjugate samples in HEPES buffer were completely intact and stable (see FIG. 3b). Conjugate HS-1-60-1 stored in HEPES has a MW of 6730 Da before and after the AST, demonstrating that both mannose residues, the multimeric scaffold, and insulin are all chemically unchanged and quite stable. To ensure conjugate stability, all buffers used for storage, in vitro testing, and in vivo testing contain HEPES as the buffering agent.

The LC-MS data greatly enhances FDA manufacturing regulatory compliance, as the LC-MS test can readily act as the chemical identity assay of the conjugate. Since the drug (e.g., insulin), multimeric scaffold, and conjugate all have discrete molecular weights, the resulting affinity ligand ratio can be readily calculated by subtracting the scaffold MW from the conjugate MW to give the remaining mass due to the sugar groups. In the case of conjugate HS-1-60-1, the mannose:insulin molar ratio is calculated as exactly 2.0.

Example 36

Functional Stability of Conjugates

Figure 4:
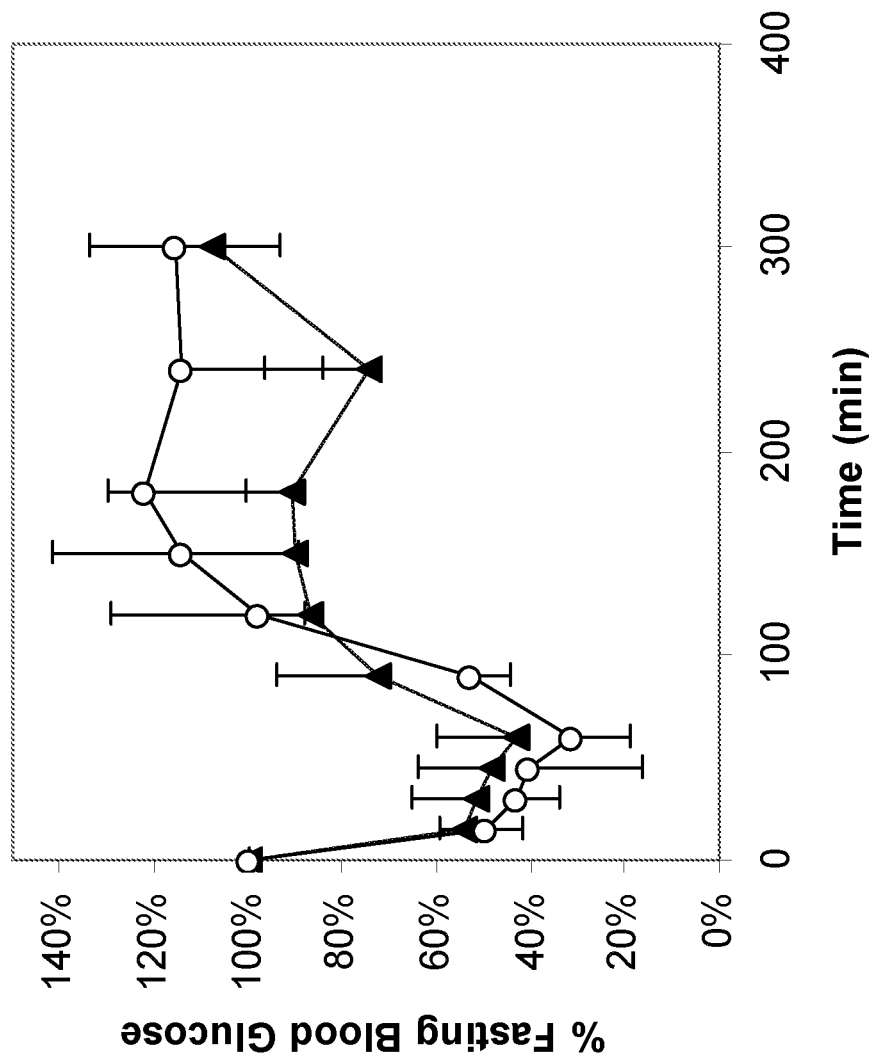
FIG. 4: In vivo bioactivity in (n=4) non-diabetic, male Sprague-Dawley (SD) rats for fresh conjugate (▲) and 72 hr AST conjugate (○). The 72 hr AST conjugate bioactivity was indistinguishable from that of the fresh conjugate (p>0.21 for all timepoints).

After demonstrating that the conjugate was chemically and physically stable, a 72 hour AST conjugate was assessed for its subcutaneous bioactivity in vivo vs. fresh conjugate using Sprague-Dawley rats at 5 U/kg (see FIG. 4).

Analysis of the 72 hour HEPES AST conjugate data showed that the time to reach the glucose nadir ($T_{nadir}$) was 60 minutes, and the time to return to 70% of the fasting blood glucose values ($T_{70\%BG}$) was less than 128±15 min. A comparison of fresh conjugate vs. 72 hour AST conjugate bioactivity curves at each timepoint using the student t-test (n=4 for each group) showed no significant differences (all p-values>0.21). These results were within specified targets for the formulation, indicating that preserved conjugate chemical stability translates into preserved in vivo functional performance.

III. In Vivo Assays of Exemplary Conjugates

This third set of examples describes various experiments investigating the in vivo properties of some exemplary conjugates.

Example 37

Conjugate Bioactivity Versus RHI and Dextran or Glycogen Conjugates a. Insulin-Dextran Bioactivity This comparative example evaluates the in vivo pharmacodynamic profile of subcutaneously administered insulin-dextran (Sigma-Aldrich, MW ~70K). As shown below, the insulin-dextran conjugates synthesized according to U.S. Patent Publication No. 20040202719 act relatively slowly after subcutaneous injection, because the high MW of the conjugate polymer significantly hinders the absorption rate into systemic circulation. Insulin-dextran was synthesized using a modified cyanogen bromide (CNBr) coupling reaction. Briefly, 500 mg of dextran (MW=70K, Sigma-Aldrich) was dissolved in 50 ml of deionized water. 56 mg of solid CNBr was added to the resulting solution and the pH was maintained at 10.7±0.2 using 5 N NaOH solution. After stirring for 15 min, another 56 mg of solid CNBr was added and the pH was maintained at 10.7±0.2 while stirring for 45 minutes. 300 mg of recombinant human insulin (RHI) was then added to the solution, and the pH was adjusted to 9.15 using solid sodium bicarbonate. The solution was stirred overnight, ultrafiltered exhaustively against DI water using a 10K MWCO polyethersulfone disc membrane filter (Millipore, Bedford, Mass.), and lyophilized. The resulting powder was then purified from unconjugated insulin by high performance liquid chromatography (Waters, Milford, Mass.) using a 1 M acetic acid mobile phase over a Superdex™ 75 packed column (Amersham Biosciences, Piscataway, N.J.). The insulin-dextran fraction was then lyophilized to obtain the conjugate as a pure powder. The degree of insulin conjugation was 10% (w/w) as determined by amino acid analysis (UCLA Biopolymers Laboratory, Los Angeles, Calif.).

Figure 5:
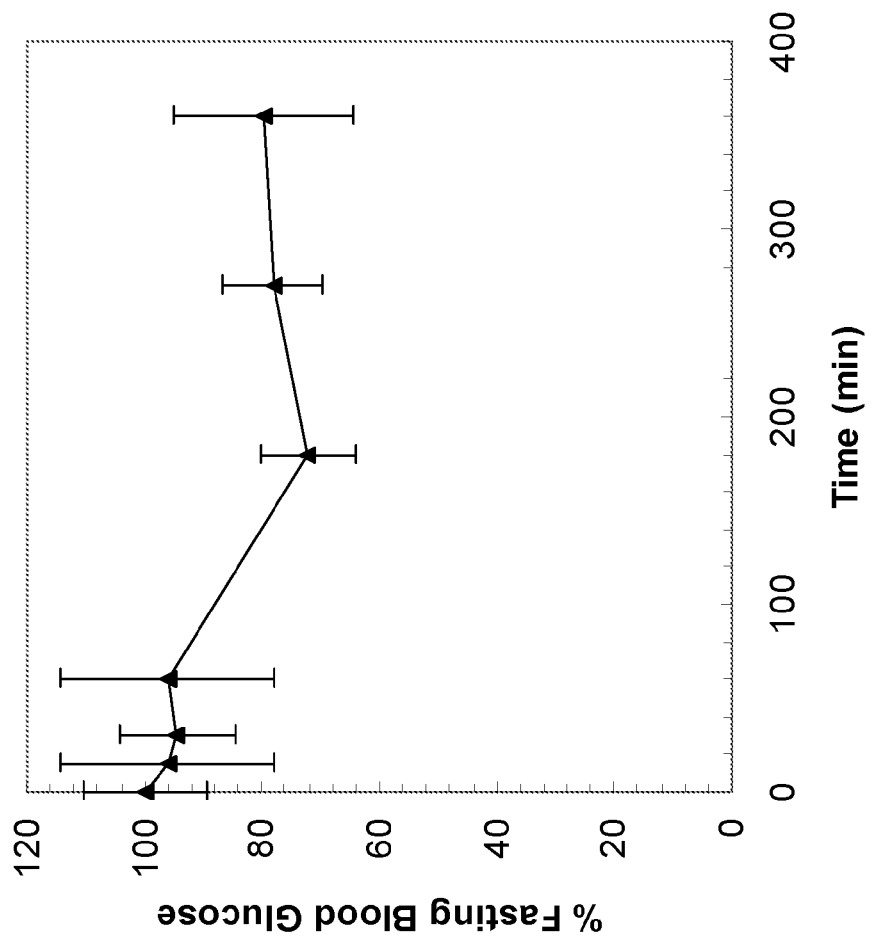
FIG. 5: Blood glucose depression profile in non-diabetic, male SD rats (n=3) for subcutaneously injected (▲) insulin-dextran (70 K) at a dose of ~20 U of insulin equivalents/kg.

Subcutaneous injections of the insulin-dextran were administered using 0.25 ml of a sterilized 1×PBS solution (20 U of equivalent insulin/ml) behind the neck of fasted normal non-diabetic rats (Male Sprague-Dawley, 200-250 g, n=4). Blood samples were collected via tail vein bleeding at −15 and 0 minutes, and at 15, 30, 45, 60, 90, 120, 180, 240, 300 and 360 minutes after injection. Blood glucose values were measured using commercially available test strips (Precision Xtra, Abbott Laboratories, Abbott Park, Ill.). As shown in FIG. 5, the times to reach the glucose nadir ($T_{nadir}$) concentration was found to be about 3 hours after injection, and the serum glucose levels remain depressed for at least five hours post injection.

b. Insulin-Glycogen Bioactivity

Figure 6:
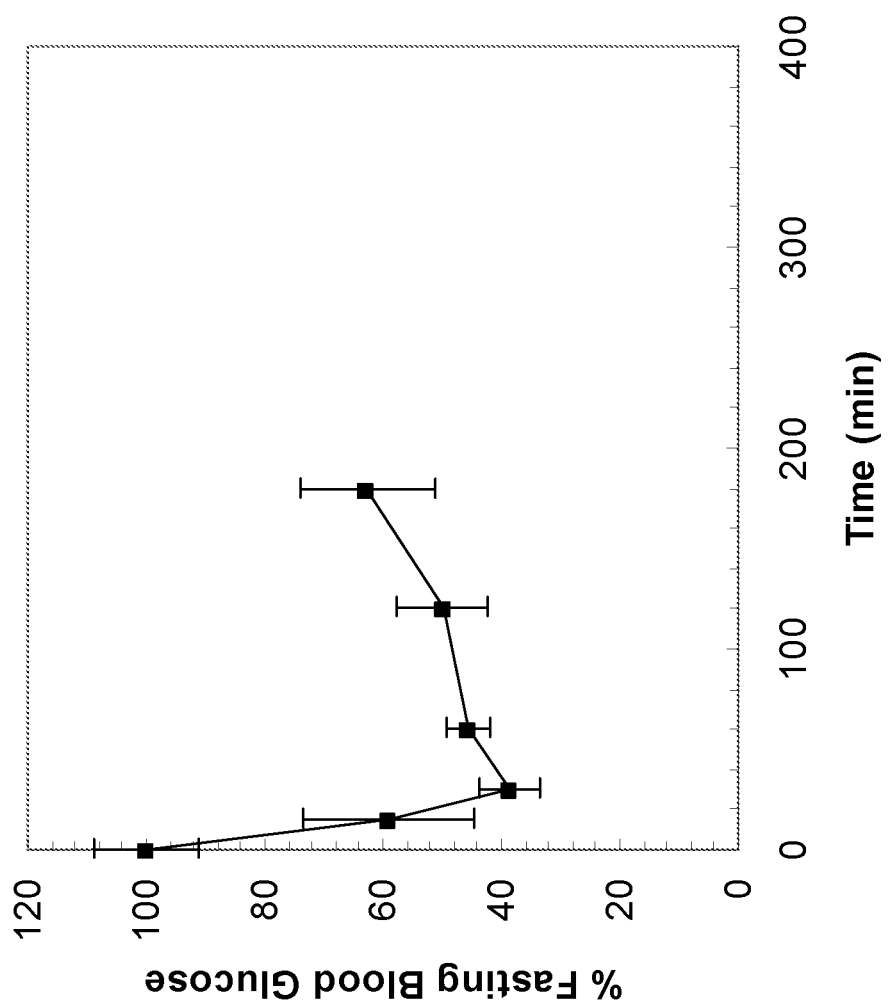
FIG. 6: Blood glucose depression profile in non-diabetic, male SD rats (n=3) for subcutaneously injected (■) insulin-glycogen (Type II oyster) at a dose of ~2.5 U of insulin equivalents/kg.

This example evaluates the in vivo pharmacodynamic profile of subcutaneously administered insulin-glycogen. The insulin-glycogen conjugate was synthesized according to Example 32. The bioactivity of the insulin-glycogen conjugate was evaluated by injecting a 2.5 equivalent U of insulin/kg dose behind the neck of fasted normal non-diabetic rats (Male Sprague-Dawley, 200-250 g, n=4). Blood samples were collected via tail vein bleeding at −15 and 0 minutes, and at 15, 30, 45, 60, 90, 120, 180, 240, 300 and 360 minutes after injection. Blood glucose values were measured using commercially available test strips (Precision Xtra, Abbott Laboratories, Abbott Park, Ill.). As compared to the insulin-dextran conjugates above, the high MW insulin-glycogen conjugates lower glucose levels much more rapidly and to a greater extent (see FIG. 6). This rapid action and elimination profile is due to the rapid enzymatic digestion of the high MW glycogen polymer chain following subcutaneous injection.

c. A Comparison of Conjugate and RHI Bioactivity

Figure 7:
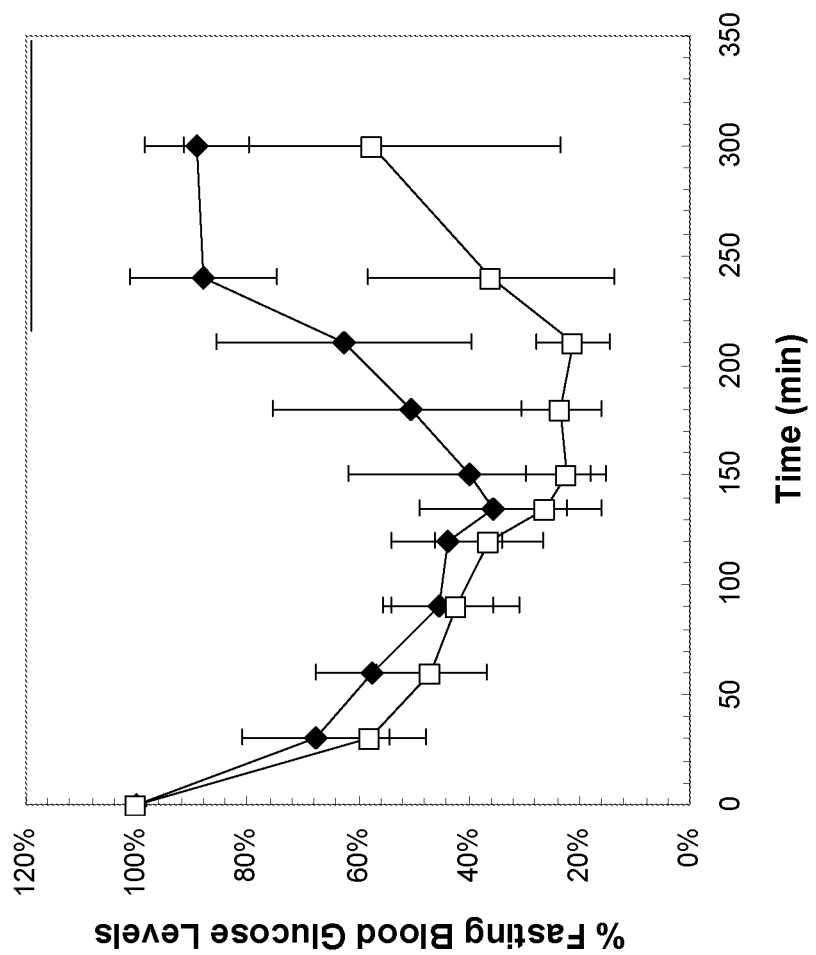
FIG. 7: Blood glucose levels resulting from a 3.5 U equivalent insulin/kg subcutaneous dose of (◆) TSAT-C6-AEM-2 insulin conjugate and (□) soluble recombinant human insulin (RHI) in male non-diabetic SD rats. Each set of data represents the average and standard deviation for n=6 rats.

This example evaluates and compares the in vivo pharmacodynamic profile of a subcutaneously administered exemplary conjugate and recombinant human insulin (RHI). The exemplary conjugate was synthesized using TSAT-C6 as the scaffold, AEM as the indicator analog, and $NH_2$-B1-BOC2 (A1,B29)-insulin as the drug. In each case, the conjugate or RHI was injected at 3.5 U/kg behind the neck of fasted normal non-diabetic rats (Male Sprague-Dawley, 400-500 g, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). As shown in FIG. 7, the glucose depression profiles for RHI and the exemplary conjugate are nearly identical despite the inability for the exemplary conjugate to be enzymatically digested in vivo. The rapid action and elimination profiles of the conjugate are most likely due to the fact that the conjugate is only 14% larger than RHI making any effect of increased MW almost negligible in terms of pharmacodynamic properties.

Example 38

PK Comparison with RHI

Figure 8:
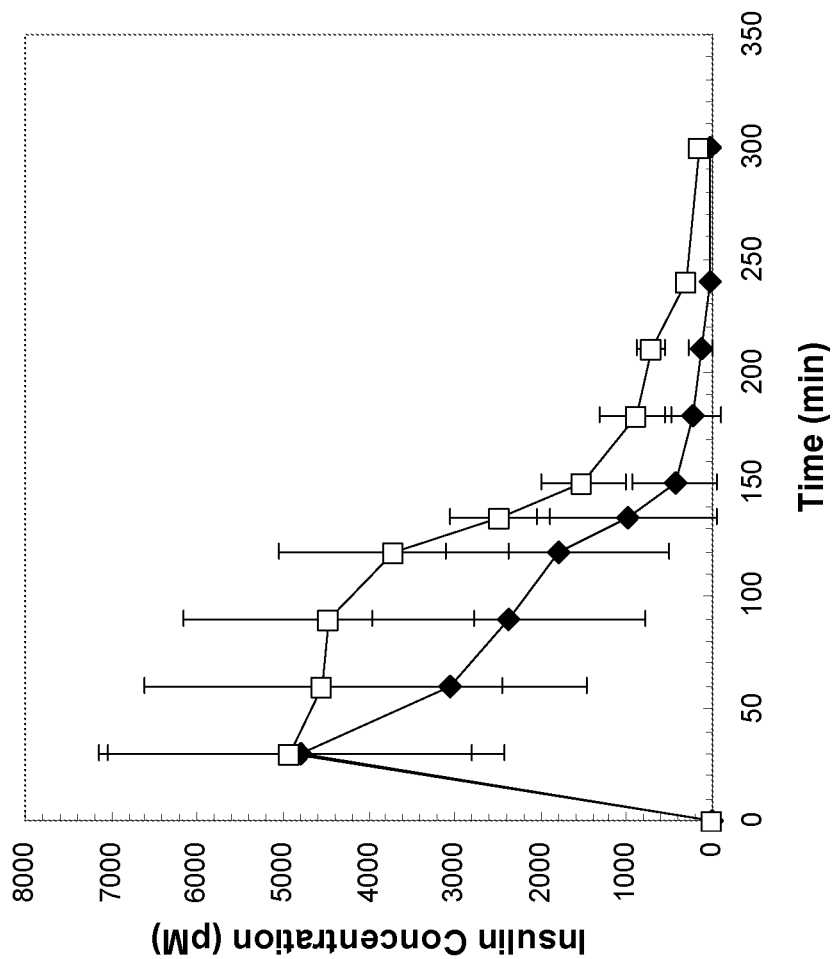
FIG. 8: Serum insulin concentrations resulting from a 3.5 U equivalent insulin/kg subcutaneous dose of (◆) TSAT-C6-AEM-2 insulin conjugate and (□) soluble recombinant human insulin (RHI) in male non-diabetic SD rats. Each set of data represents the average and standard deviation for n=6 rats.

This example describes and compares the serum insulin profiles obtained for a subcutaneously administered exemplary conjugate and recombinant human insulin (RHI). The exemplary conjugate was synthesized using TSAT-C6 as the framework, AEM as the affinity ligand, and $NH_2$-B1-BOC2 (A1,B29)-insulin as the drug. In each case, the conjugate or RHI was injected at 3.5 U/kg behind the neck of fasted normal non-diabetic rats (Male Sprague-Dawley, 400-500 g, n=6). Blood samples were collected via tail vein bleeding at 0 minutes and at 30, 60, 90, 120, 150, 180, 210, 240, and 300 minutes after injection. Blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 8, the pharmacokinetic profile for the conjugate is statistically indistinguishable from that of RHI, demonstrating that this conjugate is rapidly absorbed into and eliminated from serum following a subcutaneous injection.

Example 39

Figure 9:
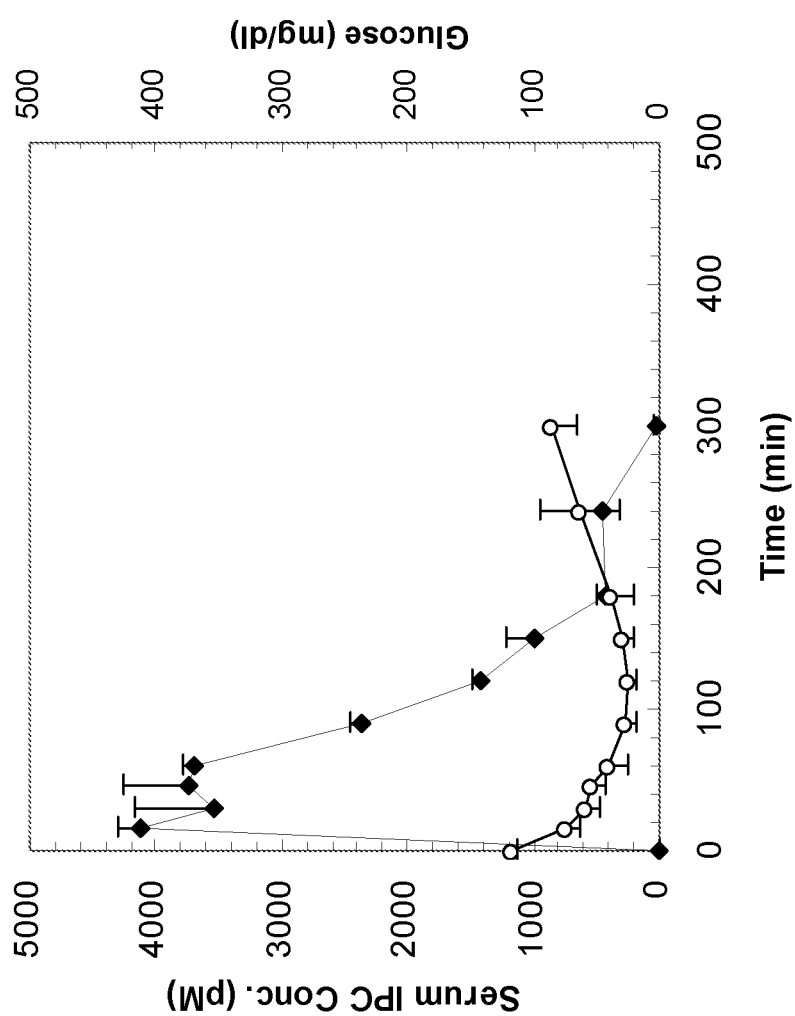
FIG. 9: Plot of (◆) serum insulin and (○) blood glucose levels following subcutaneous injection in non-diabetic, male SD rats at time 0 with TSAT-C6-AEM-2 (B29-substituted) insulin conjugate (5 U/kg). Data represents the average and standard deviation for n=3 rats.

PK and Bioactivity of a B29-Substituted Version of the AEM-2-TSAT-C6-Insulin Conjugate This example describes the serum insulin and blood glucose depression profiles obtained for a subcutaneously administered exemplary conjugate. The exemplary conjugate was synthesized using TSAT-C6 as the framework, AEM as the affinity ligand, and recombinant human insulin as the drug (to produce a B29-substituted conjugate instead of a B1-substituted conjugate as in Examples 37 and 38). In this case, the conjugate was injected at 5 U/kg behind the neck of fasted normal non-diabetic rats (Male Sprague-Dawley, 400-500 g, n=3). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 9, the pharmacokinetic profile for the B29-substituted conjugate is statistically indistinguishable from that of RHI as well as the B1-substituted conjugate from Example 38, demonstrating that this conjugate is also rapidly absorbed into and eliminated from serum following a subcutaneous injection.

Example 40

PK and Bioactivity Comparison with Lispro

This example compares the serum insulin and blood glucose profiles obtained for a subcutaneously administered exemplary conjugate and insulin lispro. Insulin lispro (HUMALOG®) is a rapid acting insulin analog in which the penultimate lysine and proline residues on the C-terminal end of the B-chain have been reversed. This modification blocks the formation of insulin multimers. Data from soluble recombinant human insulin (RHI) is also provided for comparison (see Example 38 and FIG. 8).

Figure 12:
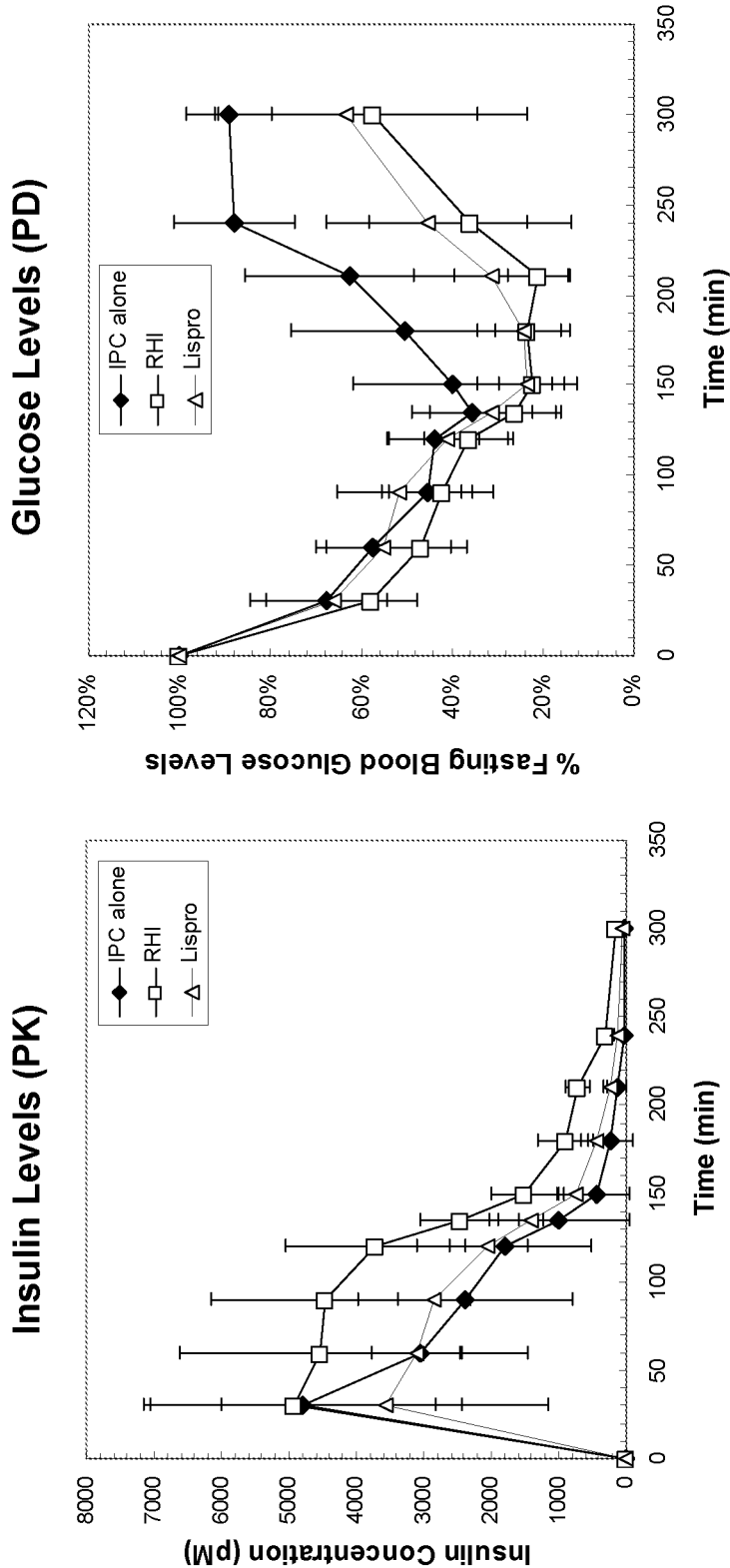
FIG. 12: Plot of serum insulin (left) and blood glucose (right) levels following subcutaneous injection in non-diabetic, male SD rats at time 0 with TSAT-C6-AEM-2 insulin conjugate (◆), soluble recombinant human insulin, (○) and insulin lispro (Δ) (all 3.5 U/kg). Data represents the average and standard deviation for n=6 rats.

The exemplary conjugate was synthesized using TSAT-C6 as the framework, AEM as the affinity ligand, and $NH_2$-B1-BOC2(A1,B29)-insulin as the drug. In each case, the conjugate or insulin lispro was injected at 3.5 U/kg behind the neck of fasted normal non-diabetic rats (Male Sprague-Dawley, 400-500 gm, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 12, the pharmacokinetic profile for the conjugate is statistically indistinguishable from that of insulin lispro.

Example 41

Effect of Affinity Ligand on Bioactivity

This example compares the blood glucose profiles obtained for a series of subcutaneously administered exemplary conjugates. The exemplary conjugates were synthesized using TSAT-C6 as the framework, and $NH_2$-B1-BOC2 (A1,B29)-insulin as the drug. The affinity ligand composition was varied across the conjugates to cover a range of affinities: AEM-2, AEBM-2, AETM-1 AEBM-1 and AETM-2 (from lowest to highest affinity). In each case, the conjugates were injected at 5 U/kg (3.5 U/kg for AEM-2) behind the neck of fasted normal non-diabetic rats (Male Sprague-Dawley, 400-500 gm, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden).

Figure 13:
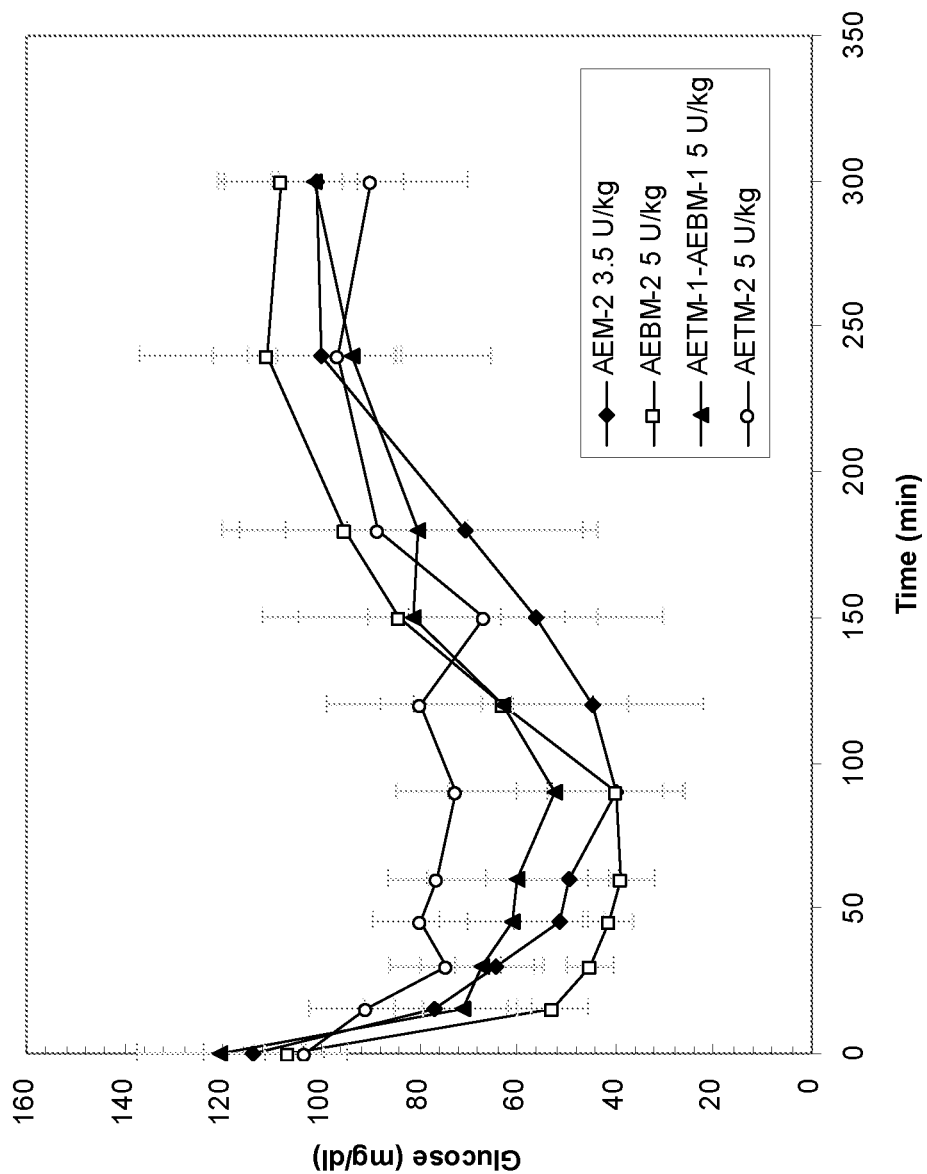
FIG. 13: Plot of blood glucose levels following subcutaneous injection in non-diabetic, male SD rats (n=3 for each formulation) at time 0 with TSAT-C6 based insulin conjugates with the different affinity ligands as shown. The glucose lowering response decreases as the affinity of the affinity ligand increases.
Figure 14:
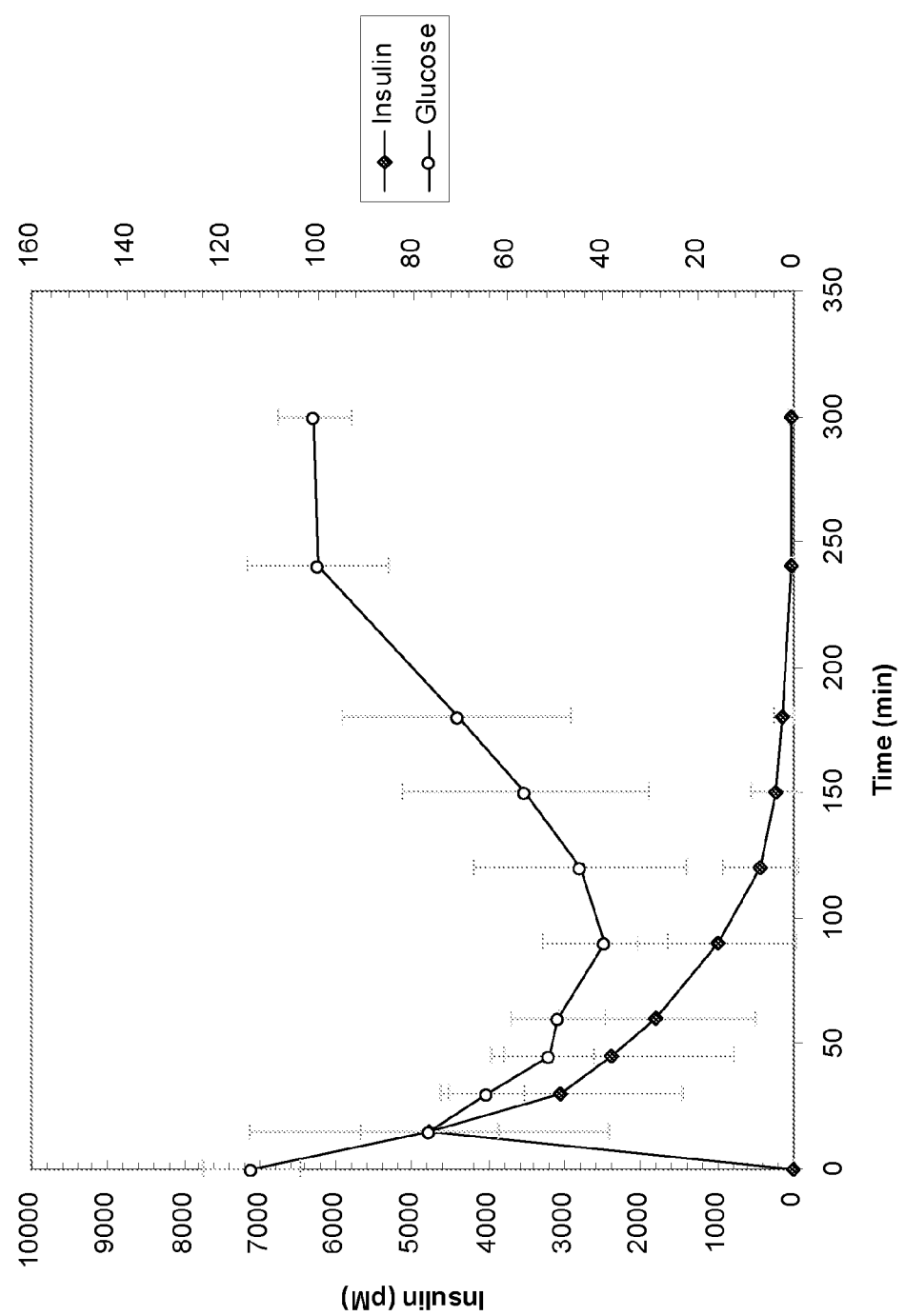
FIG. 14: Plot of serum insulin (left) and blood glucose (right) levels following subcutaneous injection in non-diabetic, male SD rats (n=3) at time 0 with TSAT-C6-AEM-2 conjugate (3.5 U/kg).
Figure 15:
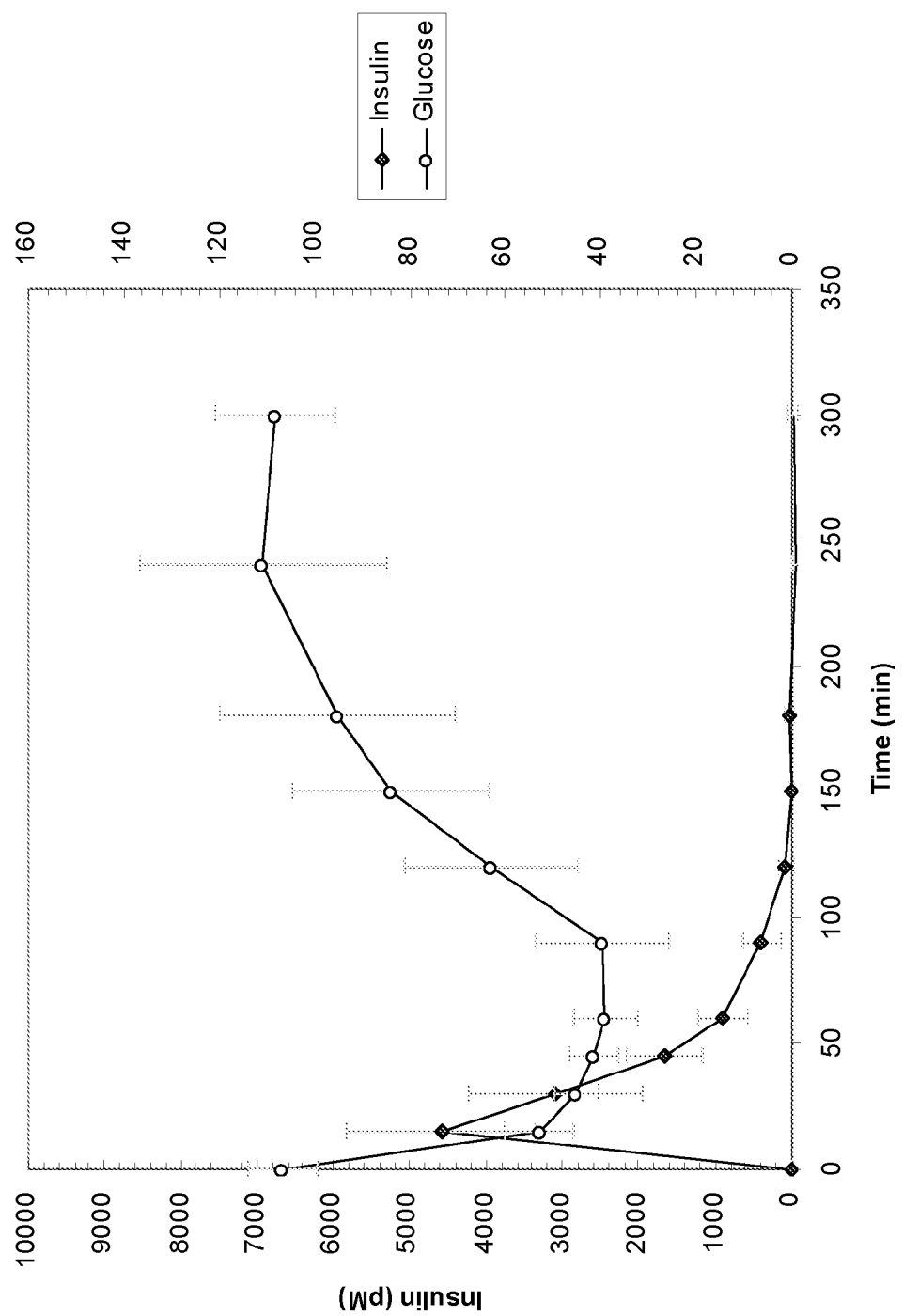
FIG. 15: Plot of serum insulin (left) and blood glucose (right) levels following subcutaneous injection in non-diabetic, male SD rats (n=3) at time 0 with TSAT-C6-AEBM-2 conjugate (5 U/kg).
Figure 16:
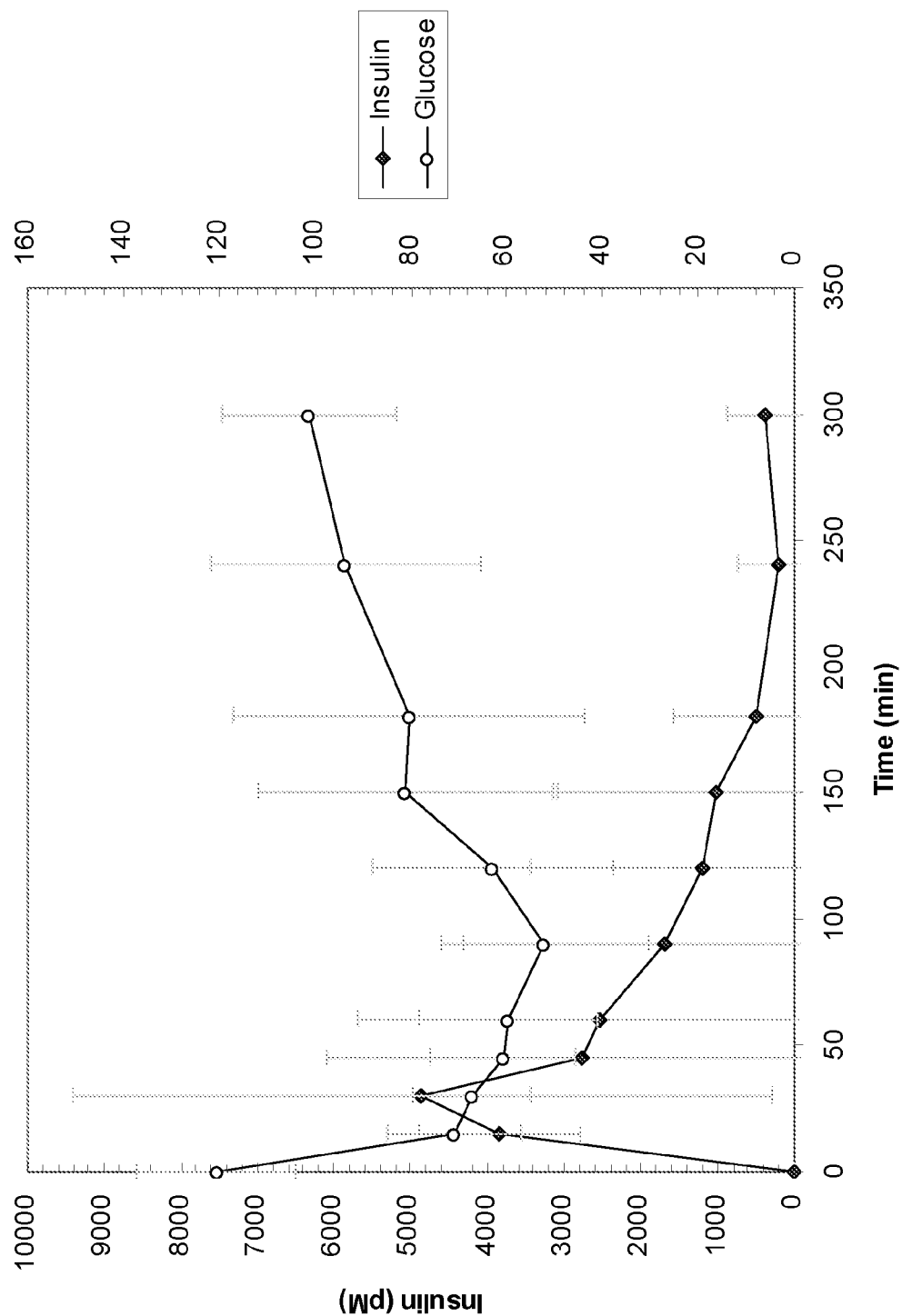
FIG. 16: Plot of serum insulin (left) and blood glucose (right) levels following subcutaneous injection in non-diabetic, male SD rats (n=3) at time 0 with TSAT-C6-AEBM-1 AETM-1 conjugate (5 U/kg).

As can be seen in FIG. 13, the glucose lowering response decreased as the affinity of the ligand increased. This data provided the first indication that the nature of the affinity ligand may affect the bioactivity of the conjugate. FIGS. 14-16, show the blood glucose levels alongside the serum insulin levels for each of the four conjugates tested. These results show quite clearly that the reduced glucose response for conjugates with higher affinity ligands result from the reduced PK profile of the conjugate (compare FIG. 14 for AEM-2 with FIG. 16 for AETM-2). As described in U.S. Ser. No. 61/147,878, filed Jan. 28, 2009 (the contents of which are incorporated herein by reference) we have demonstrated that this reduced PK profile (and associated bioactivity) can be reversed by an increase in the physiological glucose concentration (i.e., the level of conjugate in circulation rises with increasing glucose concentration). It will be appreciated that, in certain embodiments, this glucose dependence can be used to further tune the in vivo properties of a conjugate.

IV. Binding-Site Modified Lectins

This fourth set of examples describes the preparation and testing of a variety of binding-site modified lectins.

Example 42

Synthesis of Azidophenyl-Sugar Modified Con A

All steps were performed at room temperature unless otherwise specified. First, 5.0 g of native Con A (Sigma-Aldrich, St. Louis, Mo.) was dissolved in 200 ml of a 10 mM pH 5.0 acetate buffer solution containing 150 mM sodium chloride, 2 mM calcium chloride, 2 mM manganese chloride, and 0.1% w/v sodium azide (S28 buffer) and any insoluble material was separated by centrifugation and/or filtration. We have found that different commercial preparations of native Con A contain appreciable concentrations of inhibitory sugars that are, in certain embodiments, removed prior to photoaffinity modification. To that end, the solution was purified through a Biogel-P6 size exclusion column with an S28 mobile phase two times. Finally, the resulting solution was diluted with S28 to a final volume of 1 L. Under gentle stirring conditions, 0.4 g of hydroquinone (Sigma-Aldrich, St. Louis, Mo.) was added followed by 165 mg of either azidophenylglucose (APG, PolyOrg Inc., Leominster, Mass.) or azidophenylmannose (APM, PolyOrg. Inc., Leominster, Mass.). The solution was stirred in the dark at 4 C for one hour at the lowest possible stir speed. After one hour of stirring, any additional insoluble material was removed via centrifugation and/or filtration. 200 ml of the solution was poured into a 9"×13" aluminum pan and reacted at 4 C inside a CL-1000 UV crosslinking oven (UVP, Upland, Calif.) for 15 min at 360 nm (the UV reaction may also take place using 302 nm light). Following the reaction, any additional insoluble material was removed via centrifugation and/or filtration. The clarified solution was then purified 1× through Biogel-P6 size exclusion columns (Econopak, Bio-Rad Labs, Hercules, Calif.) with an S28 mobile phase. The UV crosslinking reaction and P6 purification process was then repeated until the entire solution was reacted. Finally, the combined P6-purified solutions were concentrated down to ~180 ml using a Pall tangential flow filtration cartridge apparatus (Millipore, Billerica, Mass.) equipped with Omega 30K membranes. The resulting solution was clarified via centrifugation and/or filtration and passed through 0.22 um filters prior to affinity column purification.

Example 43

Generalized Synthesis of Diazirine Photoreactive Ligands 0.9 mmol of aminoethyl (AE) functionalized sugar ligand (e.g., AEG, AEM, AEBM, AETM) were dissolved in 4 ml of anhydrous DMSO after which 1.6 ml of anhydrous triethylamine (TEA) were added to form a cloudy emulsion. In a separate container, 200 mg (0.9 mmol) of NHS-diazirine (Thermo Fisher Scientific Inc., Rockford, Ill.) powder was dissolved in 4 ml of anhydrous DMSO under dark conditions. Once dissolved, the NHS-diazirine solution was added dropwise to the AE-sugar solution and then allowed to react overnight at room temperature in the dark. TLC analysis (50% ethanol:50% ethyl acetate) of the overnight solution confirmed complete reaction as evidenced by the co-elution of the UV signal of the diazirine moiety (254 nm) and the sugar signal (sulfuric acid-ethanol stain) and concomitant disappearance of the AE-functionalized sugar ligand from the origin of the TLC (sulfuric acid-ethanol stain). The solution was then diluted into 80 ml of a pH 5.0, 25 mM HEPES solution containing 0.15 M sodium chloride, pH adjusted to pH 5 if necessary, and then frozen until required for photoaffinity reaction with Con A.

Example 44

Synthesis and Characterization of Sugar-Functionalized Diazirine Con A

All steps were performed at room temperature unless otherwise specified. First, 5.0 g of native Con A (Sigma-Aldrich, St. Louis, Mo.) was dissolved in 200 ml of a 10 mM pH 5.0 acetate buffer solution containing 150 mM sodium chloride, 2 mM calcium chloride, 2 mM manganese chloride, and 0.1% w/v sodium azide (S28 buffer) and any insoluble material were separated by centrifugation and/or filtration. We have found that different commercial preparations of native Con A contain appreciable concentrations of inhibitory sugars that are, in certain embodiments, removed prior to photoaffinity modification. To that end, the solution was purified through a Biogel-P6 size exclusion column with an S28 mobile phase two times. Finally, the resulting solution was diluted with S28 to a final volume of 1 L. Next, the solution volume was brought up to 1 L-⅓ ligand volume, using 1×S28 and poured into a 1 L media bottle with stir bar. Under gentle stirring conditions in the dark, 0.4 g of hydroquinone (Sigma-Aldrich, St. Louis, Mo.) was dissolved. Next, 33 ml of the diazirine-sugar conjugate obtained in Example 43 was added in 7 aliquots under gentle stirring conditions in the dark. Once dissolved, the entire solution was incubated under gentle stirring for an additional 10 min at 4 C in the dark. After 10 min of stirring, any additional insoluble material was removed via centrifugation and/or filtration. 250 ml of the solution was poured into a 9"×13" aluminum pan and reacted at 4 C inside a CL-1000 UV crosslinking oven (UVP, Upland, Calif.) for 15 min at 360 nm. Following the reaction, any additional insoluble material was removed via centrifugation and/or filtration. The clarified solution was then purified 1× through Biogel-P6 size exclusion columns (Econopak, Bio-Rad Labs, Hercules, Calif.) with an S28 mobile phase. The UV crosslinking reaction and P6 purification process was then repeated until the entire solution was reacted. Finally, the combined P6-purified solutions were concentrated down to ~180 ml using a Pall tangential flow filtration cartridge apparatus (Millipore, Billerica, Mass.) equipped with Omega 30K membranes. The resulting solution was clarified via centrifugation and/or filtration and passed through 0.22 um filters prior to affinity column purification.

Example 45

Affinity Column Purification of Modified Con A Samples

Photoaffinity modified lectins synthesized according to Examples 42 and 44 were purified via affinity column chromatography to separate fully reacted material from unreacted and/or partially reacted material. 100-200 ml of solution was injected onto a XK50/100 column (50 mm diameter×100 cm length) packed with glucose-containing Superdex 30 beads (GE Healthcare Life Sciences, UK) equilibrated with S28 buffer. The column was then eluted for 4 hours at 5 ml/min with S28. The desired fraction, having been fully reacted, eluted first from the column followed by partially reacted material which still had a partial affinity for the glucose-containing stationary phase. Typically, material eluting from 70-120 min was collected and the rest discarded. The column was then washed at 5 ml/min with S28 buffer containing 80 mM alpha-methyl-mannose solution for six hours to remove any unreacted lectin followed by regeneration in S28 at 5 ml/min for another six hours. The collected fraction was concentrated using Amicon Ultra 30K ultrafiltration membranes (Millipore, Billerica, Mass.) to approximately 100 ml and passed through 0.22 um filters prior to any further affinity column purification steps. The column purification process was repeated a second, third, and fourth time to obtain sufficiently pure material for subsequent studies. After the fourth purification step, the material was concentrated using Amicon Ultra 30K ultrafiltration membranes (Millipore, Billerica, Mass.) to approximately 18 mg/ml as determined by the solution absorbance at 280 nm (A280). This solution was passed through a 0.22 um filter and stored at 4 C until required for future studies.

Example 46

Chemical Characterization of Modified Con A Samples a. SDS-PAGE

Denaturing polyacrylamide gel electrophoresis (PAGE) using sodium dodecyl sulfate (SDS) was performed on the materials to ensure that no adverse proteolytic cleavage occurred as a result of exposure to UV light. Briefly, a 10-15% Tris-HCl pre-made gel (Criterion, Bio-Rad, Hercules, Calif.) and 1× Tris-glycine-SDS buffer (Bio-Rad, Hercules, Calif.) were used to perform the PAGE experiment. A broad-range molecular weight standard (Bio-Rad, Hercules, Calif.) and a 2 mg/ml sample of native concanavlin A lectin (Con A, Type VI, Sigma-Aldrich, St. Louis, Mo.) were also run as controls. 25 uL of each modified lectin or control sample was dissolved in 50 uL of 1× Laemmli Buffer (Bio-Rad, Hercules, Calif.) containing 5 uL of -mercaptoethanol (Fisher Scientific), and the samples were heated in a boiling water bath for approximately 5 minutes. After the samples had cooled to room temperature, 20 uL of each sample was loaded into the wells of the pre-made PAGE gels. The samples were then run at 200 volts for 60 minutes. After the electrophoresis, the gels were fixed in a solution of deionized water:methanol:glacial acetic acid in a volume ratio of 60:30:10 for 30 minutes, followed by two washes in deionized water. Finally, the gels were stained with 1× Bio-Safe Coomassie Blue stain (Bio-Rad, Hercules, Calif.) for 60 minutes. The final gels were imaged with a light table and digital camera to record the stained gel. The stained protein bands were assayed for their molecular weights by comparing against the molecular weight and native Con A control samples. Proteolytic cleavage of the modified lectin samples during exposure to UV light would result in molecular weight bands that appear to be lower MW and distinctly different than those present in the native Con A control.

b. Matrix-Assisted Laser Desorption Ionization (MALDI) Mass Spectroscopy

Those skilled in the art will recognize that MALDI is a well known technique to characterize protein molecular weights. MALDI can be used to characterize the modified lectin sub-unit MW after conjugation to affinity ligand and subsequent affinity column purification to calculate the extent to which the modified lectin has been covalently linked with affinity ligand.

Modified lectin samples at 2 mg/ml were added to BioSpin 30 columns (Bio-Rad, Hercules, Calif.) that had been previously equilibrated with deionized water. The BioSpin columns were centrifuged for 4 minutes at 1000×g, and the resulting eluent contained modified lectin samples that had been substantially desalted. The samples were frozen on dry ice and shipped for MALDI analysis using a sinnapic acid matrix.

c. Analytical Ultracentrifugation (AUC)

AUC is a technique used to determine the native molecular weight of protein samples as they exist in solution. Since some lectins include quaternary structures (e.g., Con A) it is recommended to uncover the molecular mass of the modified lectins under non denaturing conditions (SDS-PAGE, MALDI).

Modified lectin samples and control native Con A (Type VI, Sigma-Aldrich, St. Louis, Mo.) samples were dissolved at concentrations of 1.0, 0.5, and 0.25 mg/ml in S28 buffer containing 12.5 mM α-D-mannose, and these were placed into the AUC cells of a Beckman XL-I analytical ultracentrifuge (Biophysical Instrumentation Facility, MIT, Cambridge, Mass.) and successively spun at speeds of 10 k, 20 k, 30 k, or 40 k rpm and allowed to equilibrate for multiple hours at each speed. Each cell was scanned at a wavelength of 280 nm, and Winmatch software (Cambridge, Mass.) was used to determine the equilibration times of the AUC cells. The obtained AUC data for each sample was fit using a non-linear least squares analysis using WinNonLin v1.06 (UConn, Rockville, Conn.) to obtain the molecular weight of the sample.

d. Isothermal Calorimetry

Titration calorimetry was performed at 25 C in a Micro-Cal VP-ITC microcalorimeter (Biophysical Instrumentation Facility, MIT, Cambridge, Mass.), using a 1.4 ml (nominal) titration cell. Typical modified lectin concentrations were in the range of 4-6 mg/ml in PBS buffer (10 mM $NaPO_4$ pH 7.2, 150 mM NaCl, 0.2 mM $CaCl_2$). Samples were titrated with 10 mM methyl-α-D-mannopyranoside in the same buffer, using one 2 μl increment initially to clear the syringe, followed by 9 injections of 4 μl, increasing to 8 μl for the 11th to 30th addition, at intervals of 240 sec. Normally, the latter additions showed only background heat of dilution (i.e., total saturation). Data (eliminating the first data point, and any others that were obviously bad) were fit to the single site model using Origins software supplied with the instrument.

e. MAC Assay

Various photoaffinity-labeled lectins such as those synthesized in Examples 42 and 44 and purified according to Example 45 were compared based on their ability to agglutinate cells possessing affinity ligands to which the unmodified lectin is capable of binding. The minimum agglutinating concentrations (MAC) of each composition was determined in V-well microtitre plates using a 2% v/v suspension of formaldehyde-stabilized rabbit erythrocytes according to the procedure of Crowley et al., Methods. Enzymol. 83:368-373, 1982. Formaldehyde-treated rabbit erythrocytes, prepared by published procedures (Nowak et al., Biochim. Biophys. Acta 393:115-123, 1975), from rabbit blood obtained from University of Michigan Unit for Laboratory Animal Medicine, were available from previous studies. The MAC was defined as the lectin protein concentration (exclusive of attached chemical compounds) in the highest dilution showing visible agglutination.

Briefly, an aqueous solution of a lectin composition was added to the wells of a 96-well plate using dilutions so that the lectin concentration spanned from about 0.1 to 1000 ug/ml. An aliquot of the formaldehyde-treated Rabbit erythrocytes was then pipetted into each well. At low lectin concentrations, there was insufficient lectin to form a network of crosslinked cells and the cells dropped to the bottom of the V-well forming what looks like a dark pin-point circle at the bottom of the plate when viewed from above. However, once the lectin concentration reached the minimum agglutination concentration (MAC), the lectin molecules began crosslinking the saccharide receptors on the erythrocyte surfaces, resulting in a network that cannot settle to the bottom of the V-well forming what looks like a large, opaque, diffuse circle when viewed from above. The lowest concentration that produces the large diffuse circle is the MAC value for a particular formulation.

Figure 17:
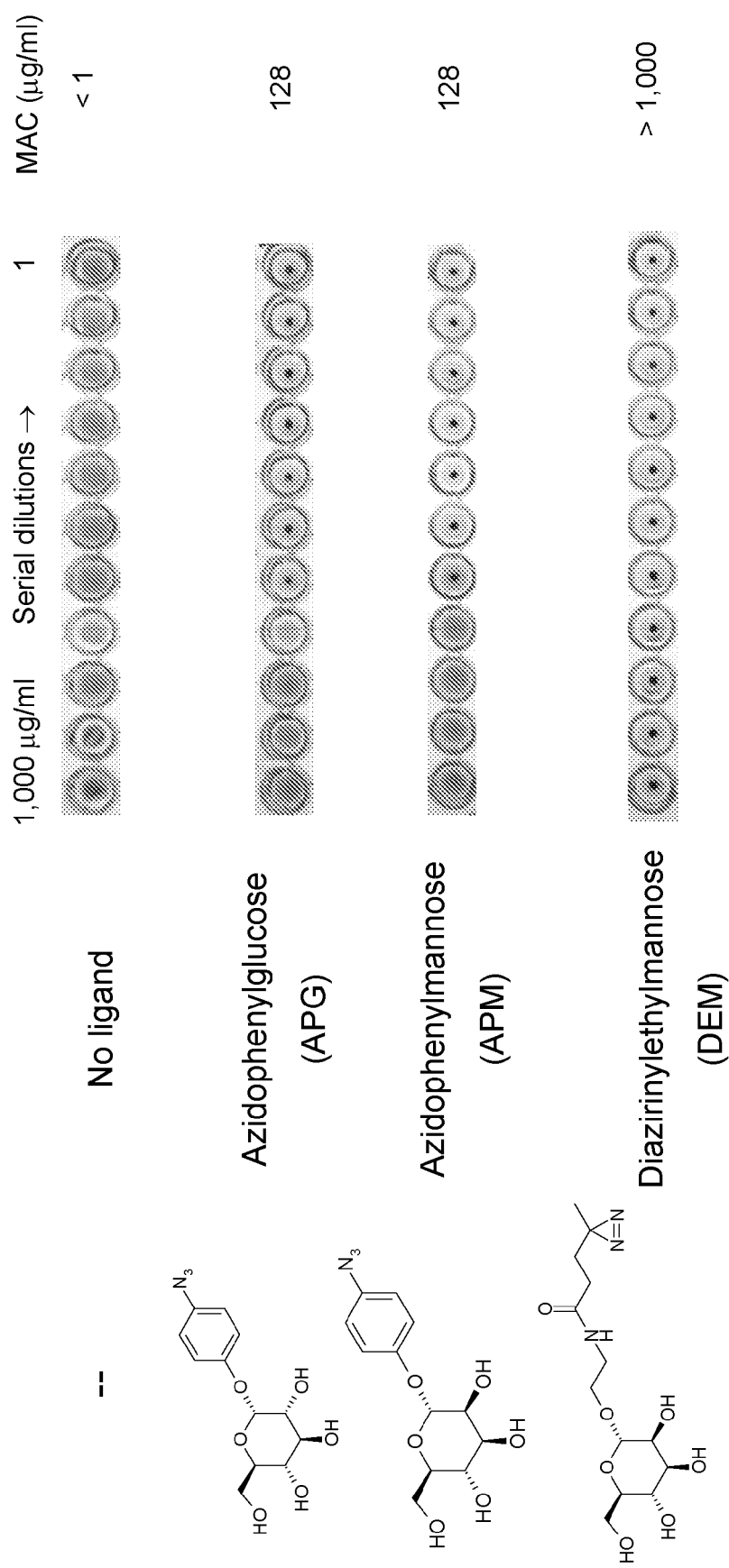
FIG. 17: Comparison of minimum agglutinating concentrations (MAC) for lectins modified with different affinity ligands.

The following table summarizes the MAC values for Con A-based formulations synthesized according to the examples described above (see also FIG. 17):

| Modified lectin | Affinity ligand type | Synthesis method | MAC (ug/ml) |
| --- | --- | --- | --- |
| Umodified | — | — | <1 |
| APG-Con A | APG | Example 42 | 128 |
| APM-Con A | APM | Example 42 | 128 |
| DEM-Con A | AEM-diazirine | Examples 43-44 | >1,000 |

Example 47

Mitogenicity Assay

This example describes an assay that may be used to characterize and thereby compare the T-cell mitogenicity of different modified lectin compositions. Modifications and alternatives to this typical assay will be apparent to those skilled in the art. Peripheral blood mononuclear cells (PBMCs), rather than highly purified T-cells, are used for this assay since T-cell activation by lectins generally requires the presence of non-T-cell populations collectively termed accessory cells (e.g., monocytes, dendritic cells). In a typical assay, PBMCs are isolated from the whole blood of three healthy human donors and plated out separately at about 100,000 cells per well in a 96 well plate. Triplicate serial dilutions of different lectin compositions (e.g., native and treated) starting at 1000 (or 100) ug/ml concentration are then added to the wells. The plates are incubated for three days at 37 C, at which time 0.8 uCi of $^3$H-thymidine is added to each well for an additional 18 hours. The degree of mitogenicity is then measured by $^3$H-thymidine uptake by the proliferating PBMCs. In some cases, the mitogenicity of a novel lectin composition (e.g., a treated composition) is expressed as the % maximal native mitogenicity. The % maximal native mitogenicity is obtained by dividing the maximal CPM (counts per minute) value for the modified lectin composition over all measured concentrations by the maximal CPM value of the native lectin composition over all measured compositions.

In previous studies we have found found a strong correlation between the MAC value and % Con A maximal mitogenicity, i.e., a significant increase in MAC value leads to a significant decrease in mitogenic effect. Therefore, MAC value is used in the present disclosure as a surrogate for determining potential reductions in mitogenicity for a given chemical modification.

V. Cross-Linked Materials for Controllably Releasing a Conjugate

This fifth set of examples describes the preparation of exemplary cross-linked materials for controllable releasing conjugates. The examples also describe some of their in vitro and in vivo properties.

Example 48

Cross-Linked Materials Prepared from Modified Con A 0.50 ml of a 18 mg/ml DEM-Con A solution in S28 was added to a centrifuge tube and subsequently mixed with 0.111 ml of a 1.18 mg/ml zinc acetate dihydrate deionized water solution. 0.50 ml of a 2.3 mg/ml solution of C6-amine-AEBM-2-insulin in pH 8.2, 25 mM HEPES buffer containing 0.150 M sodium chloride (S14 buffer) was then added followed by rapid mixing to form a dispersion of insoluble particles. The dispersion was allowed to sit at room temperature for 20 min and then separated from the supernatant by centrifugation. The resulting cake was washed 2x with 1.0 ml of pH 7.4, 25 mM HEPES buffer containing 0.150 M sodium chloride (S24 buffer). During this process, the initial supernatant as well as the 2x wash solutions were collected in one large centrifuge tube. To the combined supernatant and wash solutions, 0.333 ml of a 1.18 mg/ml zinc acetate dihydrate deionized water solution were added. The solution was allowed to stand for 20 min after which any additional precipitated particles were isolated via centrifugation and combined with the particles remaining from the first two washing steps. This combined insoluble fraction was washed an additional 3x with 0.333 ml of S24 buffer. The remaining insoluble material was dispersed in 0.333 ml of S24 buffer and incubated overnight under mild agitation at 37 C. The next day, the remaining particles were again isolated by centrifugation and washed one additional time in 0.333 ml of S24. The resulting insoluble material was dispersed in a total volume of 0.30 ml using S24 and set aside for future studies. This process may be scaled up directly to produce any amount of desired product. C6-amine-AEBM-2-insulin may be substituted in the above synthesis with C6-amine-AETM-2-insulin (or any other conjugate) to produce a formulation with different stimuli-responsive performance characteristics.

Example 49

IPGTT Experiments in Non-Diabetic Rats 0.300 ml of a given cross-linked material is injected subcutaneously into each of three normal male Sprague Dawley (SD) rats (Charles River Laboratories, location) weighing between 400 and 500 g. Prior to formulation injection, blood glucose values are measured via tail vein bleeding using a Precision Xtra glucometer (Abbott Laboratories, Alameda, Calif.) and approximately 100 ul of serum is obtained via tail vein bleeding to assay for background insulin levels. Food is removed from the rat cages during the duration of the study. Serum and blood glucose values are obtained at 30 min, 60 min, 90 min, and 120 min post-injection. At 120 min after the injection, an intraperitoneal injection of a 38% w/v glucose solution is injected to provide a 4 g/kg dose after which serum and blood glucose values are obtained at 135 min, 150 min, 180 min, 210 min, 240 min, and 300 min. Serum insulin concentrations are subsequently measured with a commercially available ELISA kit (Human Insulin ELISA, Mercodia, Uppsala, Sweden) using a standard curve generated from the pure insulin conjugate solution.

Figure 18:
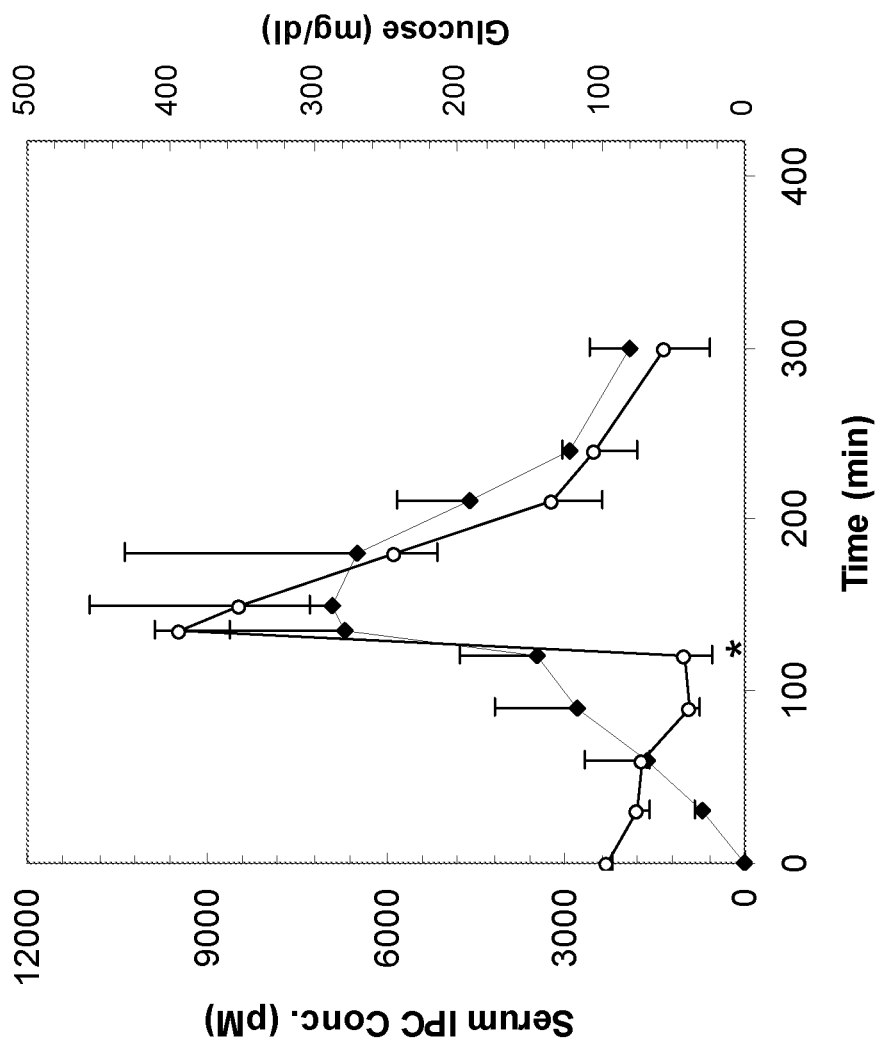
FIG. 18: Plot of (◆) serum insulin and (○) blood glucose levels following subcutaneous injection in non-diabetic SD rats at time 0 with (TSAT-C6-AEBM-2-insulin/DEM-photo-affinity-modified Con A) glucose-responsive materials. An i.p. injection of glucose was administered at 120 min as indicated by the *.
Figure 19:
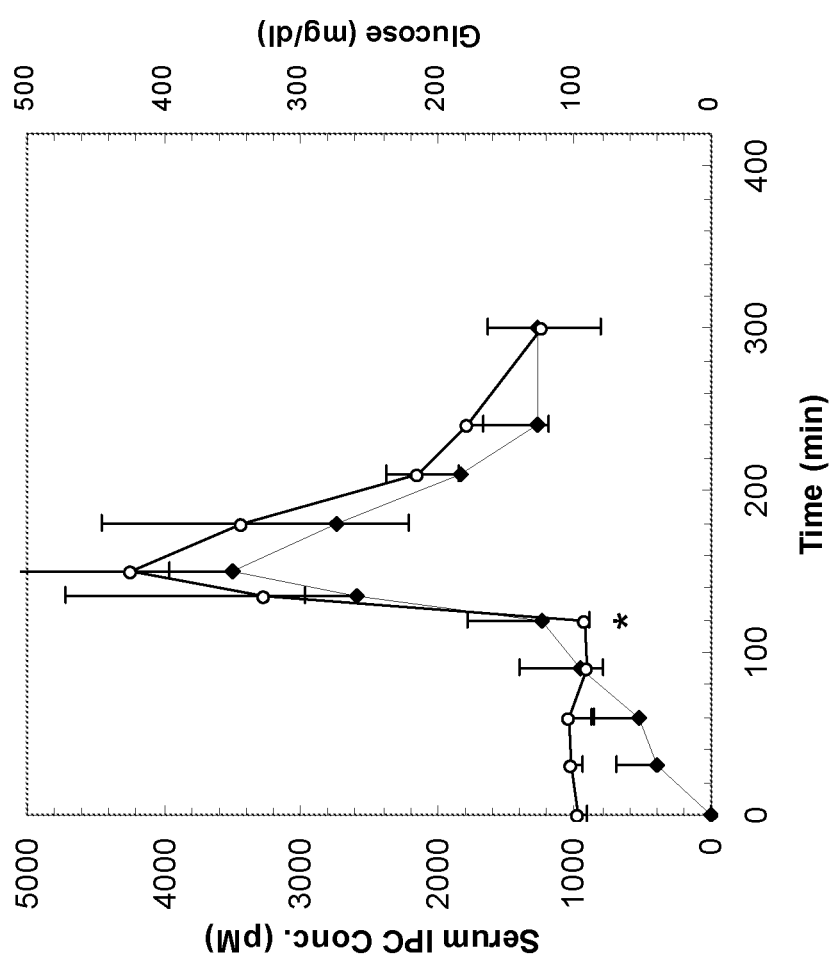
FIG. 19: Plot of (◆) serum insulin and (○) blood glucose levels following subcutaneous injection in non-diabetic SD rats at time 0 with (TSAT-C6-AETM-2-insulin/DEM-photo-affinity-modified Con A) glucose-responsive materials. An i.p. injection of glucose was administered at 120 min as indicated by the *.

FIGS. 18 and 19 show the results obtained with cross-linked materials that were constructed from DEM-Con A and C6-amine-AEBM-2-insulin or C6-amine-AETM-2-insulin, respectively according to the procedures described in Example 48. The DEM-Con A/C6-amine-AEBM-2 formulation shows ~2× increase in serum insulin concentration from baseline following the intraperitoneal glucose tolerance test (IPGTT) indicating glucose-responsive delivery in vivo. The DEM-Con A/C6-amine-AETM-2 formulation on the other hand shows 3-4× increase in serum insulin concentration from baseline in response to glucose following the IPGTT with significantly less material leaking out of the system at physiologically normal glucose concentrations. Furthermore, the injection sites in all animals receiving DEM-Con A formulations showed absolutely no signs of inflammation or necrosis due to the presence of the lectin further confirming the improved safety profile of the photoaffinity-modified materials.

Example 50

Effect of Different Animal Sera on Glucose-Responsive Dissolution of Insulin-Glycogen Cross-Linked Materials and Correlation to Amylase Activity This example describes the in vitro dissolution in various animal sera as a function of glucose concentration for glucose-responsive formulations synthesized using an insulin-glycogen based conjugate. The insulin-glycogen conjugate was synthesized according to the following procedure. First, 62.5 ml of a 10 mg/ml recombinant human insulin solution (RHI) in pH 8.2, 25 mM HEPES buffer (Sigma-Aldrich, St. Louis, Mass.) was adjusted to pH 9.0 and cooled on ice to produce the RHI stock solution. Separately, 0.312 ml of triethylamine (TEA, Sigma-Aldrich, St. Louis, Mass.) was dissolved in 3 ml of DI water to produce the TEA stock solution. Separately, 0.300 g of cyanodimethylamino pyridinium tetrafluoroborate (CDAP, Sigma-Aldrich, St. Louis, Mo.) was dissolved in 1.2 ml of DMSO to produce the CDAP Stock solution. Separately, 100 mg of mannosamine-HCl (Sigma-Aldrich, St. Louis, Mo.) was dissolved in 1.5 ml of a 100 mM pH 9 HEPES saline buffered saline solution and pH adjusted to 9.0 to produce the mannosamine stock solution. Separately, 2.0 g of oyster Type IX glycogen (Sigma-Aldrich, St. Louis, Mo.) was dissolved in 40 ml of a 100 mM pH 9 HEPES saline buffered saline solution after which the solution was clarified by filtration and cooled on an ice bath. Next, 1 ml of the CDAP stock solution was added to the glycogen solution and mixed for one minute after which 1 ml of the TEA solution was added and the pH of the resulting solution adjusted to 9.0. After an additional 1 minute of stirring, 62 ml of the RHI solution were added and the resulting solution stirred for five minutes followed by addition of 1.065 ml of the mannosamine solution. The solution was stirred overnight at room temperature, ultrafiltered exhaustively against deionized water using a 50 kDa MWCO polyethersulfone disc membrane filter (Millipore, Bedford, Mass.), and lyophilized. The resulting powder was then purified 3× from unconjugated insulin by gel filtration HPLC (Waters, Milford, Mass.) using a 1 M acetic acid mobile phase over a Superdex™ 30 HiLoad 16/60 (Amersham Biosciences, Piscataway, N.J.) packed column. The insulin glycogen fraction was then lyophilized to obtain the conjugate as a pure white powder.

Twenty-four glucose-responsive formulations were prepared using acetylated Con A (ACA) as the multivalent crosslinking agent in the following manner. 200 ul of a 25 mg/ml insulin-glycogen conjugate solution in pH 7.0 HEPES buffered saline was mixed with 200 ul of a 25 mg/ml chemically-modified, acetylated Con A (ACA) solution in pH 7.0 HEPES buffered saline and allowed to stand for 20 minutes. Next, each formulation was centrifuged and washed 5× at room temperature with 400 ul of pH 7.0 HEPES buffered saline. After the last wash and centrifugation, the supernatant was discarded and the remaining insoluble material dispersed in 50 ul of 1×PBS.

The 24×50 ul dispersions were added to a 96-well plate along with 50 ul of serum from a particular animal species containing a specific amount of glucose according to the following format:

| Insulin-glycogen/ACA cross-linked material | Species sera | | | |
|---|---|---|---|---|
| Glucose Concentration (mg/dl) | pH 7, 1× PBS | Rat | Pig | Human |
| 0 | 1 | 7 | 13 | 19 |
| 50 | 2 | 8 | 14 | 20 |
| 100 | 3 | 9 | 15 | 21 |
| 200 | 4 | 10 | 16 | 22 |
| 400 | 5 | 11 | 17 | 23 |
| 800 | 6 | 12 | 18 | 24 |

At the start of the experiment each well appeared white and opaque (as measured by a decrease in light transmission or increase in absorbance at 450 nm, A450). The 96-well plate was then incubated for 6 hours at 37 C after which the A450 value for each well was measured again. The % of the formulation remaining was calculated by dividing the A450 (final) by the A450 (initial) and multiplying by 100. If all the material had dissolved, the A450 value was close to zero indicating almost 0% remaining. Alternatively, if no material had dissolved, the A450 was close to the initial value indicating almost 100% remaining.

Figure 20:
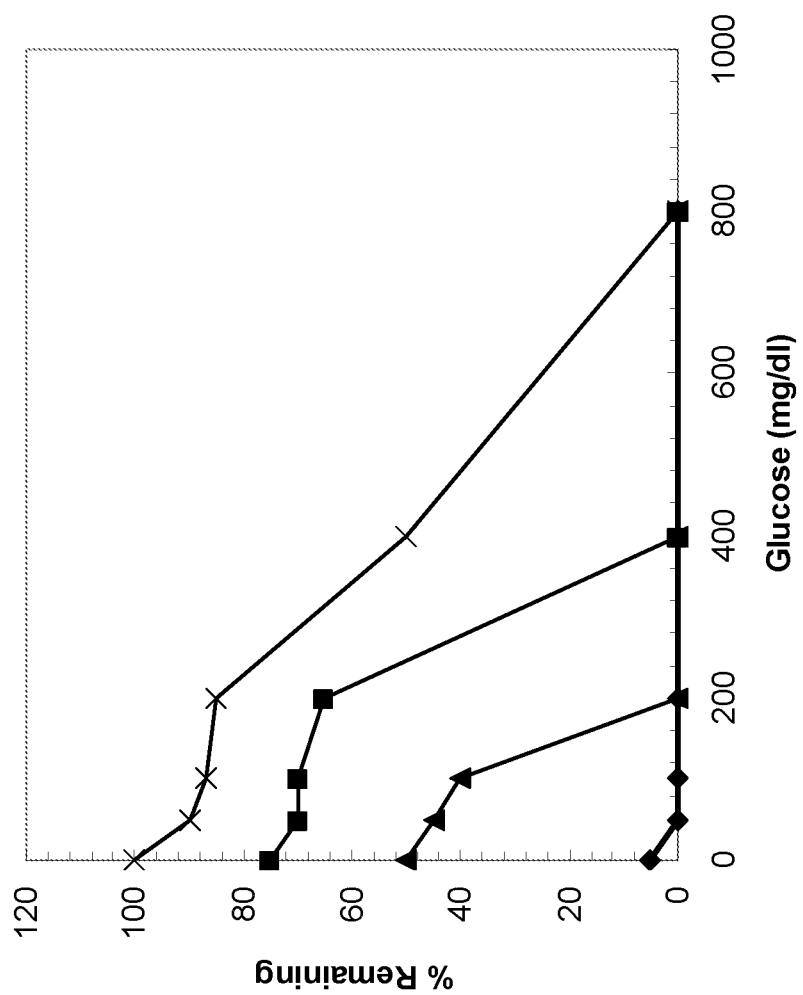
FIG. 20: Amount of glucose-responsive, insulin-glycogen-based material remaining insoluble as a function of glucose concentration after six hours of incubation at 37° C. in the presence of (◆) porcine serum, (■) human serum, (▲) rat serum, and (x) 1×PBS buffer.

The results in FIG. 20 show that the cross-linked materials constructed from insulin-glycogen conjugates dissolve in an ideal glucose responsive manner over the six hour study when incubated in buffered saline. However, the materials dissolve completely regardless of the glucose concentration when incubated in pig serum. Rat serum maintains some glucose responsiveness but dissolves significantly over six hours even in the absence of glucose. Over 20% of the material incubated in human serum still dissolves in the absence of glucose.

Figure 21:
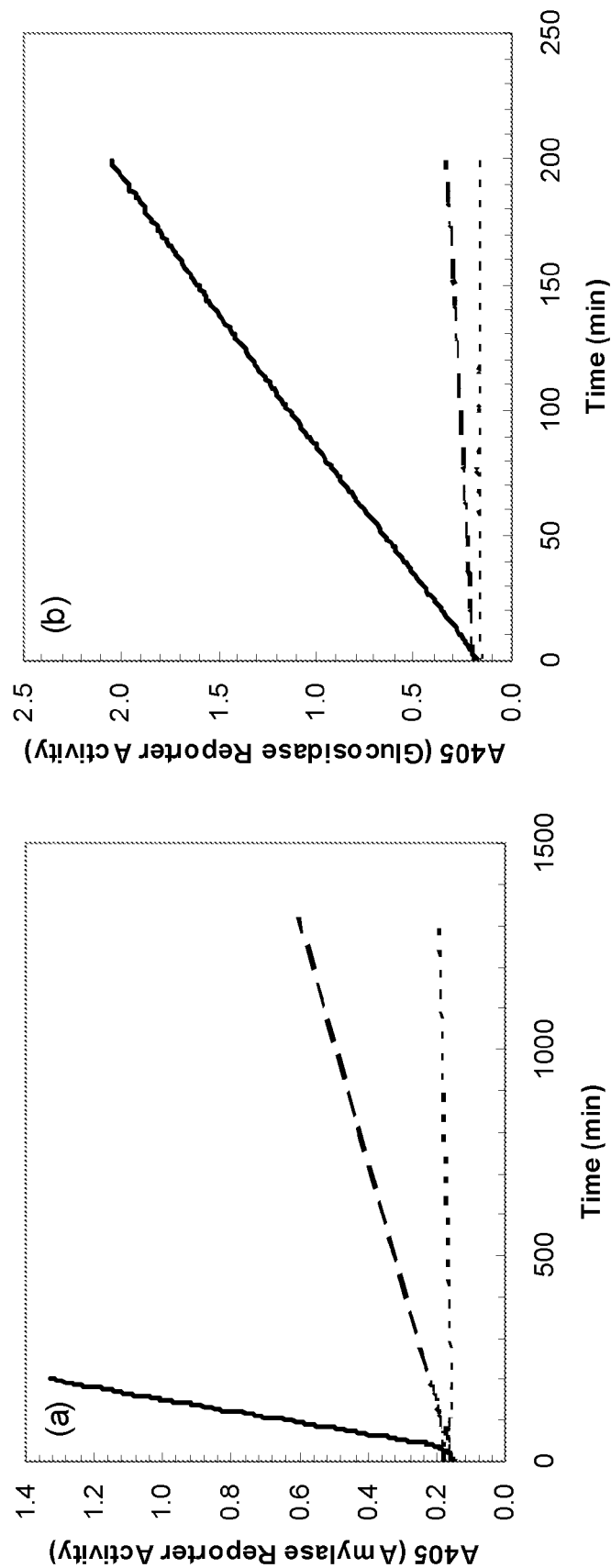
FIG. 21: Digestion activity of 1:8 dilutions of porcine (solid line), rat (long dash line), and human (short dash line) serum in PBS as measured by production of colorimetric signal (A405) for (a) amylase activity (4-Nitrophenyl α-D- penta-(1→4)-glucopyranoside reporter) and (b) glucosidase activity (4-Nitrophenyl α-D-glucopyranoside reporter).

These differences were correlated to each species' intrinsic amylase and glucosidase digestion activity by first developing a microplate assay that takes advantage of the production of a colorimetric signal from oligosaccharides connected through linear α-1,4 glycosidic bonds like glycogen. To investigate amylase activity, 4-Nitrophenyl α-D-penta-(1→4)-glucopyranoside (Sigma Aldrich, St. Louis, Mo.) was used, and 4-Nitrophenyl α-D-glucopyranoside (Sigma Aldrich, St. Louis, Mo.) was used to investigate glucosidase activity. For each assay, serum from a particular species was diluted by increasing amounts with 1×PBS and a known concentration of colorimetric reporter was spiked into the solution after which the absorbance signal at 405 nm (A405) was measured as a function of time. FIGS. 21a and 21b illustrate the A405 production due to enzyme activity in each of the different species of serum tested for amylase and glucosidase activity, respectively. Here we see that at a 1:8 dilution of serum in PBS, porcine serum exhibits approximately 17× the digestion activity of rat serum. Furthermore, there appears to be almost no activity whatsoever in the human serum tested under these conditions. Therefore, the differences in the material dissolution profiles in each species' serum are directly correlated with the ability for that species' serum to digest the underlying glycogen conjugate. Taken together, these results provided the impetus for designing a subcutaneous bioactive conjugate such as the ones described in this disclosure to circumvent the glycogen-digestion limitation but still form glucose-responsive materials.

Example 51

Glucose-Responsive Material Using ACA and an AEM-2 Conjugate

This example describes the formation of glucose-responsive insoluble materials using a conjugate synthesized with TSAT-C6 as the framework, AEM as the affinity ligand, and $NH_2$-B1-BOC2(A1,B29)-insulin as the drug. 50 ul of a 2 mg/ml conjugate solution in pH 8.2 HEPES buffered saline was mixed with 50 ul of a 25 mg/ml chemically-modified, acetylated Con A (ACA) solution in pH 7.0 HEPES buffered saline in each well of a 96-well microplate. Each well contained 5.5 ul of a concentrated glucose solution of increasing concentrations to produce final concentrations equal to 0, 50, 100, 200, 400, 800, and 1600 mg/dl. The final well contained 5.5 ul of the highly potent alpha-methyl mannose sugar inhibitor such that the final concentration was 100 mM. The ability of the ACA/conjugate mixture to precipitate in the presence of increasing glucose concentrations was then evaluated. When the combination forms an insoluble network, the well appears white and opaque (as measured by a decrease in light transmission or increase in absorbance at 450 nm, A450) as shown in FIG. 22. When the glucose concentration is high enough, the contents of the entire well become soluble and clear (as measured by an increase in light transmission or decrease in absorbance at 450 nm, A450). The results clearly show that this particular formulation is most responsive to concentrations between 100 and 400 mg/dl, an ideal candidate for in vivo testing. Furthermore, as described below, this particular conjugate exhibits almost the same subcutaneous bioactivity as unconjugated insulin without requiring enzymatic digestion to exert its biological effects.

Example 52

Similar Performance Across all Animal Sera

This example describes the in vitro dissolution in various animal sera as a function of glucose concentration for the glucose-responsive formulation of Example 51.

24×50 ul dispersions were added to a 96-well plate along with 50 ul of serum from a particular animal species containing a specific amount of glucose according to the following format:

| Insulin-glycogen/ACA cross-linked material | Species sera | | | |
|---|---|---|---|---|
| Glucose Concentration (mg/dl) | pH 7, 1× PBS | Rat | Pig | Human |
| 0 | 1 | 7 | 13 | 19 |
| 50 | 2 | 8 | 14 | 20 |
| 100 | 3 | 9 | 15 | 21 |
| 200 | 4 | 10 | 16 | 22 |
| 400 | 5 | 11 | 17 | 23 |
| 800 | 6 | 12 | 18 | 24 |

At the start of the experiment each well appeared white and opaque (as measured by a decrease in light transmission or increase in absorbance at 450 nm, A450). The 96-well plate was then incubated for 6 hours at 37 C after which the A450 value for each well was measured again. The % of the formulation remaining was calculated by dividing the A450 (final) by the A450 (initial) and multiplying by 100. If all the material had dissolved, the A450 value was close to zero indicating almost 0% remaining. Alternatively, if no material had dissolved, the A450 was close to the initial value indicating almost 100% remaining. The results are shown in FIG. 22.

When compared to the insulin-glycogen formulation tested under the same conditions (see FIG. 20), this new formulation was not only glucose-responsive and resistant to dissolution at low glucose concentrations, but its glucose-responsive properties were nearly identical in all the species tested (see FIG. 23).

Example 53

Glucose-Responsive Material Using ACA and an AEM-2 Conjugate

This example describes an alternative method for forming glucose-responsive insoluble materials using a conjugate synthesized with TSAT-C6 as the framework, AEM as the affinity ligand, and $NH_2$-B1-BOC2(A1,B29)-insulin as the drug. 0.50 ml of a 2.3 mg/ml solution of conjugate in pH 8.2, 25 mM HEPES buffer containing 0.150 M sodium chloride (S14 buffer) was added to a centrifuge tube and subsequently mixed rapidly with 0.500 ml of a 25 mg/ml ACA solution in pH 7.4, 25 mM HEPES buffer containing 0.150 M sodium chloride (S24 buffer) to form a dispersion of insoluble particles. The dispersion was allowed to sit at room temperature for 20 min and then separated from the supernatant by centrifugation. The resulting cake was washed 5× with 1.0 ml of pH 7.4, 25 mM HEPES buffer containing 0.150 M sodium chloride (S24 buffer). After the last wash, the remaining insoluble material was incubated overnight at 37 C. The next day, the remaining particles were again isolated by centrifugation and washed one additional time in 1.0 ml of S24. The resulting insoluble material was dispersed in a total volume of 0.30 ml using S24 and set aside for future studies. This process may be scaled up directly to produce any amount of desired product.

Example 54

IPGTT Experiments in Non-Diabetic Rats 0.300 ml of the material prepared in Example 53 was injected subcutaneously into each of three normal male Sprague Dawley (SD) rats (Charles River Laboratories, Wilmington, Mass.) weighing between 400 and 500 g. Prior to formulation injection, blood glucose values were measured via tail vein bleeding using a Precision Xtra glucometer (Abbott Laboratories, Alameda, Calif.) and approximately 100 ul of serum was obtained via tail vein bleeding to assay for background insulin levels. Food was removed from the rat cages during the duration of the study. Serum and blood glucose values were obtained at 30 min, 60 min, 90 min, and 120 min post-injection. At 120 min after the injection, an intraperitoneal injection of a 38% w/v glucose solution was injected to provide a 4 g/kg dose after which serum and blood glucose values were obtained at 135 min, 150 min, 180 min, 210 min, 240 min, and 300 min. Serum insulin concentrations were subsequently measured with a commercially available ELISA kit (Human Insulin ELISA, Mercodia, Uppsala, Sweden) using a standard curve generated from the pure insulin conjugate solution. Endogenous rat insulin does not cross-react on this assay; therefore, any results obtained were due solely to the exogenously administered insulin conjugate and not from endogenous insulin from the animal (See Human Insulin ELISA kit instructions, Mercodia, Uppsala, Sweden).

In a separate experiment, 0.300 ml of saline was injected subcutaneously into each of three normal male Sprague Dawley (SD) rats (Charles River Laboratories, Wilmington, Mass.) weighing between 400 and 500 g. Prior to saline injection, blood glucose values were measured via tail vein bleeding using a Precision Xtra glucometer (Abbott Laboratories, Alameda, Calif.) and approximately 100 ul of serum was obtained via tail vein bleeding to assay for background insulin levels. Food was removed from the rat cages during the duration of the study. Serum and blood glucose values were obtained at 30 min, 60 min, 90 min, and 120 min post-injection. At 120 min after the injection, an intraperitoneal injection of a 38% w/v glucose solution was injected to provide a 4 g/kg dose after which serum and blood glucose values were obtained at 135 min, 150 min, 180 min, 210 min, 240 min, and 300 min. Serum insulin concentrations were subsequently measured with a commercially available ELISA kit specific for Rat Insulin (Rat Insulin ELISA, Mercodia, Uppsala, Sweden). The results from this experiment established the glucose-responsive endogenous insulin secretion produced by the pancreas in a normal, non-diabetic rat.

In a separate experiment, 5 U/kg of recombinant human insulin (RHI, Sigma-Aldrich, St. Louis, Mo.) was injected subcutaneously into each of three normal male Sprague Dawley (SD) rats (Charles River Laboratories, Wilmington, Mass.) weighing between 400 and 500 g. Prior to the RHI injection, blood glucose values were measured via tail vein bleeding using a Precision Xtra glucometer (Abbott Laboratories, Alameda, Calif.) and approximately 100 ul of serum was obtained via tail vein bleeding to assay for background insulin levels. Food was removed from the rat cages during the duration of the study. Serum and blood glucose values were obtained at 30 min, 60 min, 90 min, and 120 min post-injection. At 120 min after the injection, an intraperitoneal injection of a 38% w/v glucose solution was injected to provide a 4 g/kg dose after which serum and blood glucose values were obtained at 135 min, 150 min, 180 min, 210 min, 240 min, and 300 min. Serum insulin concentrations were subsequently measured with a commercially available ELISA kit (Human Insulin ELISA, Mercodia, Uppsala, Sweden) using a standard curve generated from the pure insulin conjugate solution. Endogenous rat insulin does not cross-react on this assay; therefore, any results obtained were due solely to the exogenously administered insulin conjugate and not from endogeneous insulin from the animal (See Human Insulin ELISA kit instructions, Mercodia, Uppsala, Sweden).

FIG. 24a shows ~2× increase in serum insulin concentration from baseline following the intraperitoneal glucose tolerance test (IPGTT) indicating glucose-responsive delivery in vivo. Furthermore, the peak-baseline release profile compares favorably to the glucose-responsive endogenous insulin production in a normal, non-diabetic rat (see FIG. 24b). Finally, FIG. 25 shows that RHI injected and analyzed under the same exact conditions is absorbed and eliminated rapidly causing severe hypoglycemia during the first 120 minutes and fails to exhibit any measurable glucose-responsive profile after IPGTT administration.

Example 55

Normo-/Hyper-Glycemic Clamp Experiments in Non-Diabetic Rats

This example describes the use of glucose clamps to maintain glucose levels in rats at a constant value to obtain the steady state serum insulin concentration as a function of glucose concentration. 0.300 ml (~0.6 ml/kg of body weight) of the material prepared in Example 53 was injected subcutaneously into each of four normal, double jugular vein catheterized, male Sprague Dawley (SD) rats (Charles River Laboratories, Wilmington, Mass.) weighing between 300 and 400 g. One catheter from each rat was connected to a variable rate syringe pump containing a concentrated glucose solution. Blood glucose values were measured via tail vein bleeding every five minutes using a Precision Xtra glucometer (Abbott Laboratories, Alameda, Calif.) and the syringe pump intravenous infusion rate was adjusted periodically for the first two hours post-injection to maintain the rats at 100 mg/dl. After the first two hours, the glucose infusion rate was increased to and maintained at 400 mg/dl for an additional two hours. Serum was collected at regular intervals for insulin concentration (Human Insulin ELISA, Mercodia, Uppsala, Sweden) and blood glucose values. As shown in FIG. 26 this material exhibits a steady state increase in glucose concentration of ~4× from 100 to 400 mg/dl ($p<0.05$) and a near 1:1 matching between glucose and insulin levels ($p<0.0001$).

Example 56

Normo-/Hyper-Glycemic Clamp Experiments in Non-Diabetic Pigs and Correspondence to Results Obtained in Rats Because the particular material of Example 53 did not show significant differences in dissolution rates between rat and pig serum, the following experiment was performed to determine if similar glucose-responsive profiles could be obtained in pigs. 0.300 ml (~0.012 ml/kg of body weight) of the material prepared in Example 53 was injected subcutaneously into each of four normal, jugular vein catheterized, male Yucatan Miniature pigs (Sinclair Research, Columbia, Mo.) weighing 20-25 kg. The catheter from each pig was connected to a variable rate syringe pump containing a concentrated glucose solution. Blood glucose values were measured via intravenous catheter blood withdrawals every five minutes using a Precision Xtra glucometer (Abbott Laboratories, Alameda, Calif.) and the syringe pump intravenous infusion rate was adjusted periodically for the first two hours post-injection to maintain the pigs at 65 mg/dl. After the first two hours, the glucose infusion rate was increased to and maintained at 400 mg/dl for an additional two hours. Serum was collected at regular intervals for insulin concentration and blood glucose values. Because the insulin conjugate cross-reacts with endogenous porcine insulin, a new assay methodology was developed and implemented to detect the insulin in pigs. First, a radioimmunoassay (RIA) kit (Millipore, Billerica, Mass.) was developed to detect both porcine and the exemplary insulin conjugate with roughly the same signal to noise. The signal on this kit due to endogenous porcine insulin was determined by running a particular blank pig serum sample on a c-Peptide RIA kit (Millipore, Billerica, Mass.) and on the insulin RIA kit. Once the resulting correlation was determined, any serum sample RIA insulin signal could be converted into a contribution from endogenous insulin and conjugated insulin.

Using this method, FIG. 27 was constructed to display the net conjugate serum insulin levels (endogenous porcine insulin already substracted), which shows that this formulation exhibits a steady state increase in glucose concentration of ~6× from 65 to 400 mg/dl (p<0.05) and a near 1:1 matching between glucose and insulin levels (p<0.0001). Therefore, the formulation performs in nearly the same glucose-responsive manner in both rats and pigs.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A cross-linked material comprising:
conjugates which include an anti-diabetic drug and two or more separate affinity ligands bound to a non-polymeric framework, wherein the molecular weight of the non-polymeric framework is less than 10,000 Da; and
multivalent cross-linking agents that non-covalently bind the affinity ligands of the conjugates and thereby cross-link the conjugates to form a cross-linked material, wherein the non-covalent bonds between the multivalent cross-linking agents and the affinity ligands are competitively dissociated in the presence of excess amounts of a target molecule.

2. The material of claim 1, wherein the target molecule is glucose and the two or more separate affinity ligands comprise a saccharide.

3. The material of claim 2, wherein the two or more separate affinity ligands comprise a saccharide selected from the group consisting of glucose, mannose, glucosamine, mannosamine, methylglucose, methylmannose, ethylglucose, and ethylmannose.

4. The material of claim 2, wherein the two or more separate affinity ligands comprise aminoethylglucose (AEG), aminoethylmannose (AEM), aminoethylbimannose (AEBM) or aminoethyltrimannose (AETM).

5. The material of claim 1, wherein the conjugate has the general formula (I):

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

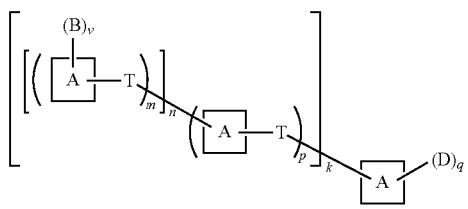

wherein:
each occurrence of

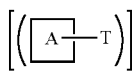

represents a potential branch within the conjugate;
each occurrence of

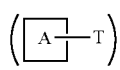

represents a potential repeat within a branch of the conjugate;
each occurrence of

is independently a covalent bond, a carbon atom, a heteroatom, or an optionally substituted group selected from the group consisting of acyl, aliphatic, heteroaliphatic, aryl, heteroaryl, and heterocyclic;
- each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;
- each occurrence of R is independently hydrogen, a suitable protecting group, or an acyl moiety, arylalkyl moiety, aliphatic moiety, aryl moiety, heteroaryl moiety, or heteroaliphatic moiety;
- —B is -T-L$^B$-X;
- each occurrence of X is independently an affinity ligand;
- each occurrence of L$^B$ is independently a covalent bond or a group derived from the covalent conjugation of a T with an X;
- -D is -T-L$^D$-W;
- each occurrence of W is independently an anti-diabetic drug;
- each occurrence of L$^D$ is independently a covalent bond or a group derived from the covalent conjugation of a T with a W;

k is an integer from 2 to 11, inclusive, defining at least two k-branches within the conjugate;

q is an integer from 1 to 4, inclusive;

k+q is an integer from 3 to 12, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1.

6. The material of claim 5, wherein the conjugate is of the formula (VIa):

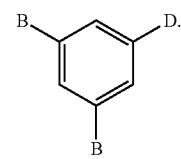

7. The material of claim 6, wherein the conjugate is of the formula (VIa-1):

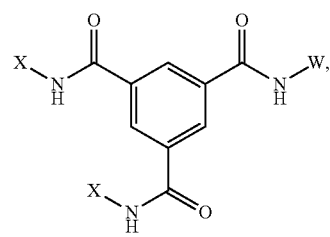

formula (VIa-2):

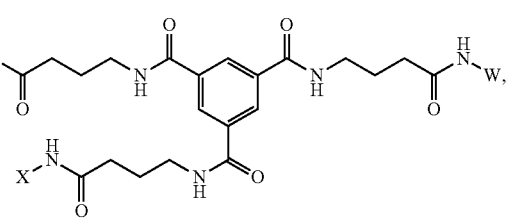

or formula (VIa-3):
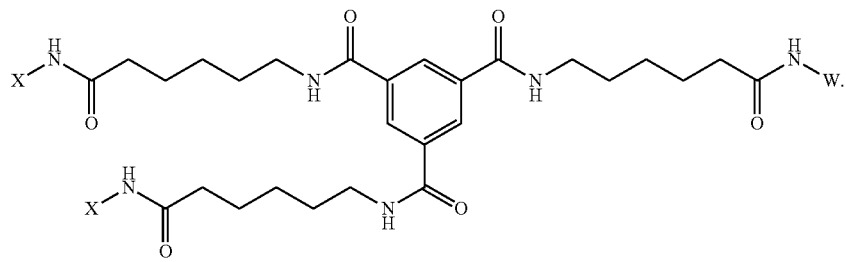
8. The material of claim 5, wherein the conjugate is of the formula (VIb):
9. The material of claim 8, wherein the conjugate is of the formula (VIb-1):
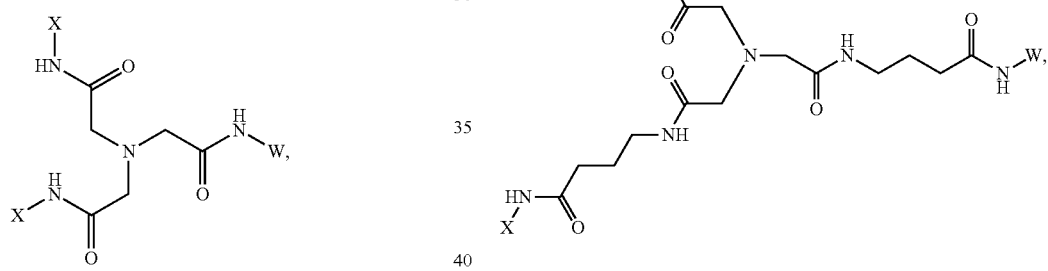
formula (VIb-2):
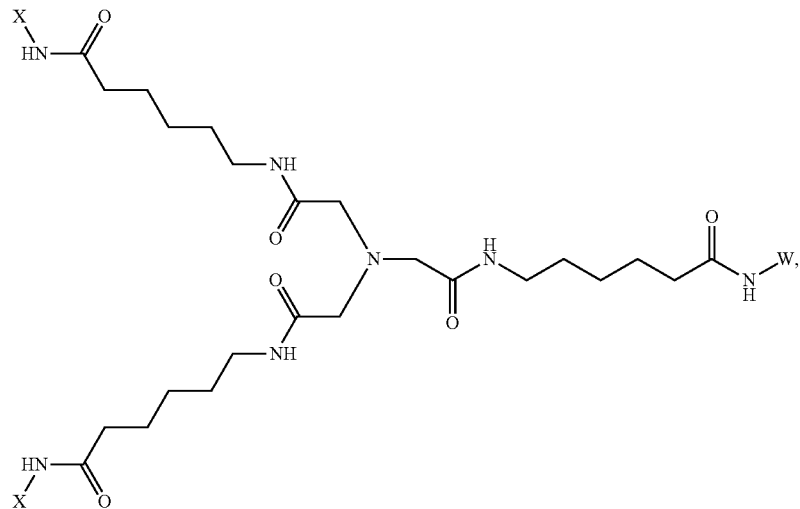
formula (VIb-3):

or formula (VIb-4):

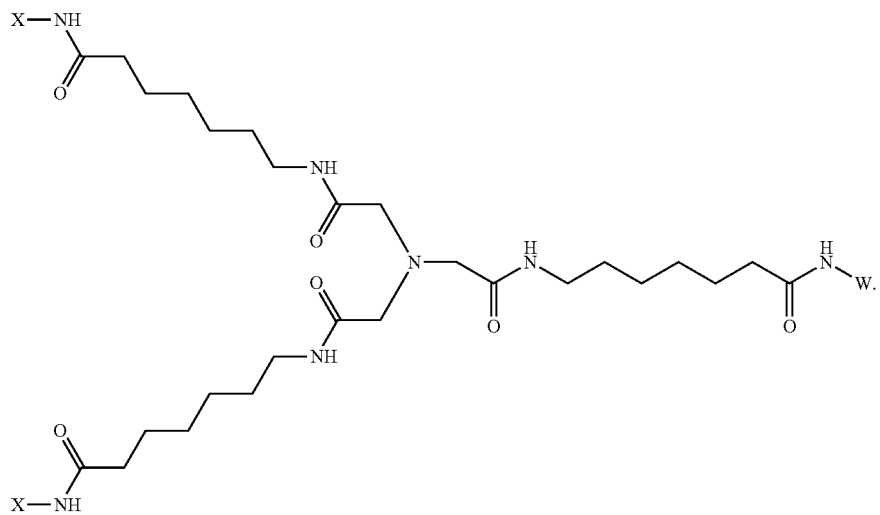

10. The material of claim 5, wherein the conjugate is of the formula (VIc):

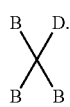

VIc

11. The material of claim 10, wherein the conjugate is of the formula (VIc-1):

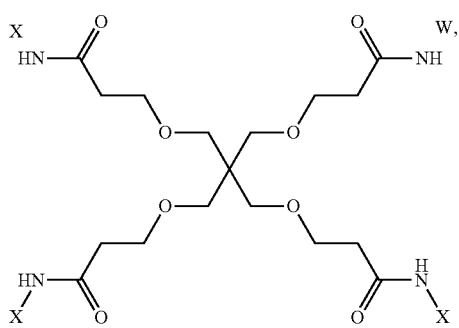

or the formula (VIc-2):

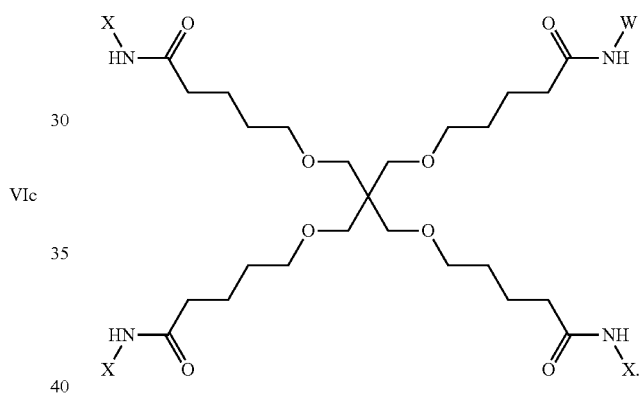

12. The material of claim 1, wherein the anti-diabetic drug is an insulin molecule.

13. The material of claim 12, wherein the insulin molecule is conjugated to the non-polymeric framework via the A1 amino acid residue of the insulin molecule.

14. The material of claim 12, wherein the insulin molecule is conjugated to the non-polymeric framework via the B1 amino acid residue of the insulin molecule.

15. The material of claim 12, wherein the insulin molecule is conjugated to the non-polymeric framework via the B29 amino acid residue of the insulin molecule.

16. The material of claim 1, wherein the multivalent cross-linking agent includes a lectin.

17. The material of claim 16, wherein the lectin is covalently bonded to a recognition element, wherein the recognition element competes with the target molecule and affinity ligands of the conjugate for binding to the lectin, and the lectin has a higher affinity for the affinity ligands of the conjugate than for the recognition element.

18. The material of claim 17, wherein the target molecule is glucose and both the affinity ligands of the conjugate and the recognition element include a saccharide.

* * * * *